United States Patent
Woo et al.

(10) Patent No.: US 7,763,642 B2
(45) Date of Patent: Jul. 27, 2010

(54) PHENYL-SULFAMATES AS AROMATASE INHIBITORS

(75) Inventors: Lok Wai Lawrence Woo, Slough (GB); Toby Jackson, Slough (GB); Christian Bubert, Slough (GB); Atul Purohit, Slough (GB); Michael John Reed, Slough (GB); Barry Victory Lloyd Potter, Slough (GB)

(73) Assignee: Sterix Ltd., Berkshire (GB)

( * ) Notice: Subject to any disclaimer, the term of this patent is extended or adjusted under 35 U.S.C. 154(b) by 0 days.

(21) Appl. No.: 11/633,572

(22) Filed: Dec. 4, 2006

(65) Prior Publication Data

US 2007/0117855 A1    May 24, 2007

Related U.S. Application Data

(63) Continuation-in-part of application No. PCT/GB2005/002194, filed on Jun. 3, 2005.

(30) Foreign Application Priority Data

Jun. 4, 2004    (GB) ................. 0412492.1

(51) Int. Cl.
  *A61K 31/4196* (2006.01)
  *C07D 249/08* (2006.01)
(52) U.S. Cl. .................... 514/383; 548/262.2
(58) Field of Classification Search .......... 514/383; 548/262.2
See application file for complete search history.

(56) References Cited

U.S. PATENT DOCUMENTS 6,821,980 B1*  11/2004  Guerry et al. ............ 514/275

2003/0220386 A1* 11/2003 Plant et al. ............... 514/408
2008/0319037 A1* 12/2008 Woo et al. ............... 514/383

FOREIGN PATENT DOCUMENTS

| WO | WO 01/32633 | 10/2000 |
| WO | WO 03/045925 | 11/2002 |
| WO | 03/045925 | 6/2003 |

OTHER PUBLICATIONS

Ex parte Esser, 2007.*
Okada, et al. "Development of Novel Steroid Sulfatase Inhibitors. I. Synthesis and Biological Evaluation of biphenyl-4-*O*-sulfamates." Journal of Steroid Biochemistry and Molecular Biology 2003; 87:141-148.

* cited by examiner

*Primary Examiner*—Yong Chu
(74) *Attorney, Agent, or Firm*—Frommer Lawrence & Haug LLP; Thomas J. Kowalski; Eugenia Kiselgof

(57) ABSTRACT

There is provided a compound of Formula I

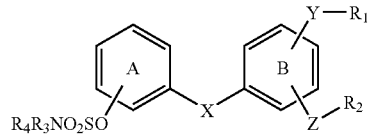

Formula I wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl, ring A and B are independently optionally further substituted.

46 Claims, 2 Drawing Sheets

ORIGIN OF OESTROGENIC STEROIDS IN POSTMENOPAUSAL WOMEN

ER=OESTROGEN RECEPTOR, DHA / -S=DEHYDROEPIANDROSTERONE / -SULPHATE, ADIOL=ANDROSTENEDIOL, E1-STS=OESTRONE SULPHATASE, DHA -STS= DHA-SULPHATASE, ADIOL-STS=ADIOL SULPHATASE, 17B-HSD=OESTRADIOL 17B-HYDROXYSTEROID DEHYDROGENASE

PHENYL-SULFAMATES AS AROMATASE INHIBITORS

REFERENCE TO RELATED APPLICATIONS

This application is a continuation-in-part of International Patent Application PCT/GB2005/002194 filed Jun. 3, 2005 and published as WO 2005/118560 on Dec. 15, 2005, which claims priority to Great Britain Patent Application No. 0412492.1 filed Jun. 4, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

Field of Invention

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHEA-S" denotes Dehydroepiandrosterone-Sulphate, "Adiol" denotes Androstenediol, "E1-STS" denotes Oestrone Sulphatase, "DHEA-STS" denotes DHEA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours. However, inhibition of both the aromatase and sulphatase pathways could offer considerable therapeutic benefit.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

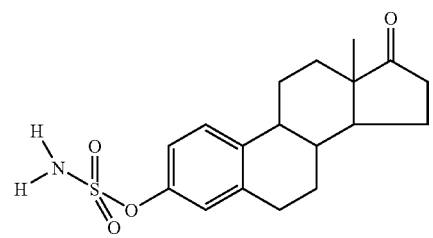

It is known that EMATE is a potent E1-STS inhibitor as it displays more than 99% inhibition of E1-STS activity in intact MCF-7 cells at 0.1 nM. EMATE also inhibits the E1-STS enzyme in a time—and concentration-dependent manner, indicating that it acts as an active site-directed inactivator. Although EMATE was originally designed for the inhibition of E1-STS, it also inhibits dehydroepiandrosterone sulphatase (DHEA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHEA-STS (99%) activities resulted when it is administered either orally or subcutaneously. In addition, EMATE has been shown to have a memory enhancing effect in rats. Studies in mice have suggested an association between DHEA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHEA-S) which is secreted in large amounts by the adrenal cortex. DHEA-S is converted to DHEA by DHEA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Our earlier application WO03/045925 teaches compounds which may act as inhibitors of both aromatase and sulphatase. Many of the compounds of the disclosure are found to be extremely potent inhibitors of both of these enzymes. However, there is a desire to provide alternative compounds or improved compounds.

The present invention seeks to provide novel compounds suitable for the inhibition of steroid sulphatase activity and aromatase activity.

SUMMARY ASPECTS OF THE PRESENT INVENTION

The present invention is based on the surprising finding that certain polycyclic compounds could be used as effective steroid sulphatase inhibitors and/or aromatase inhibitors and/or as agents that can influence cell cycling and/or as agents that can influence apoptosis.

DETAILED ASPECTS OF THE PRESENT INVENTION

According to one aspect of the present invention, there is provided a compound of Formula I

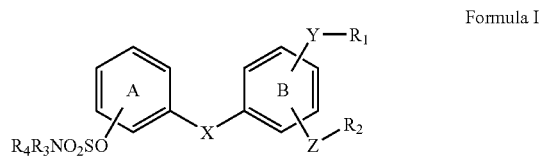

Formula I wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

According to one aspect of the present invention, there is provided a method comprising (a) performing a steroid sulphatase (STS) assay and/or aromatase assay with one or more candidate compounds defined herein; (b) determining whether one or more of said candidate compounds is/are capable of modulating STS activity and/or aromatase activity and/or cell cycling and/or cell growth and/or apoptosis; and (c) selecting one or more of said candidate compounds that is/are capable of modulating STS activity and/or aromatase activity and/or cell cycling and/or cell growth and/or apoptosis.

According to one aspect of the present invention, there is provided a method comprising (a) performing a steroid sulphatase assay and/or aromatase assay with one or more candidate compounds as defined herein; (b) determining whether one or more of said candidate compounds is/are capable of inhibiting STS and/or aromatase activity; and (c) selecting one or more of said candidate compounds that is/are capable of inhibiting STS activity and/or aromatase activity and/or cell cycling and/or cell growth and/or apoptosis.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different) and/or aromatase inhibition effects (which may be to see if the effect is greater or different). By way of further example, the method may also include the step of determining the structure (such as by use of crystallographic techniques) of the identified candidate compound and then performing computer modelling studies—such as to further increase its STS and/or aromatase inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or aromatase and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or adverse aromatase levels and/or cell cycling and/or apoptosis and/or cell growth.

According to one aspect of the present invention, there is provided the use of a compound according to the present invention in the manufacture of a medicament for inhibiting STS activity and/or inhibiting aromatase activity.

According to one aspect of the present invention, there is provided the use of a compound according to the present invention in the manufacture of a medicament for inhibiting STS activity and inhibiting aromatase activity.

The present invention also encompasses the novel compounds of the present invention (such as those presented herein), as well as processes for making same (such as the processes presented herein) as well as novel intermediates (such as those presented herein) for use in those processes.

The compounds of the present invention may comprise other substituents. These other substituents may, for example, further increase the activity of the compounds of the present invention and/or increase stability (ex vivo and/or in vivo).

For ease of reference, these and further aspects of the present invention are now discussed under appropriate section headings. However, the teachings under each section are not necessarily limited to each particular section.

Some Advantages

One key advantage of the present invention is that the compounds of the present invention can act as STS inhibitors.

One key advantage of the present invention is that the compounds of the present invention can act as aromatase inhibitors.

One key advantage of the present invention is that the compounds of the present invention can act as STS inhibitors and aromatase inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

Another advantage is that some of the compounds may not be capable of being metabolised to compounds which display or induce hormonal activity.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

Thus, some of the compounds of the present invention are also believed to have therapeutic uses other than for the treatment of endocrine-dependent cancers, such as the treatment of autoimmune diseases.

The compounds of the present invention may also be useful as an inducer of apoptosis.

The compounds of the present invention may also be useful as a cell growth inhibitors.

Preferable Aspects

Hydrocarbyl Group

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The hydrocarbyl/hydrocarbon/alkyl may be straight chain or branched and/or may be saturated or unsaturated.

In one preferred aspect the hydrocarbyl/hydrocarbon/alkyl may be selected from straight or branched hydrocarbon groups containing at least one hetero atom in the group.

In one preferred aspect the hydrocarbyl/hydrocarbon/alkyl may be a hydrocarbyl group comprising at least two carbons or wherein the total number of carbons and hetero atoms is at least two.

In one preferred aspect the hydrocarbyl/hydrocarbon/alkyl may be selected from hydrocarbyl groups containing at least one hetero atom in the group. Preferably the hetero atom is selected from sulphur, nitrogen and oxygen.

In one preferred aspect the hydrocarbyl/hydrocarbon/alkyl may be selected from straight or branched hydrocarbon groups containing at least one hetero atom in the group. Preferably the hetero atom is selected from sulphur, nitrogen and oxygen.

In one preferred aspect the hydrocarbyl/hydrocarbon/alkyl may be selected from straight or branched alkyl groups, preferably $C_{1-10}$ alkyl, more preferably $C_{1-5}$ alkyl, containing at least one hetero atom in the group. Preferably the hetero atom is selected from sulphur, nitrogen and oxygen.

In one preferred aspect the hydrocarbyl/hydrocarbon/alkyl may be selected from straight chain alkyl groups, preferably $C_{1-10}$ alkyl, more preferably $C_{1-5}$ alkyl, containing at least one hetero atom in the group. Preferably the hetero atom is selected from sulphur, nitrogen and oxygen.

The hydrocarbyl/hydrocarbon/alkyl may be selected from $C_1$-$C_{10}$ hydrocarbyl,
$C_1$-$C_5$ hydrocarbyl
$C_1$-$C_3$ hydrocarbyl.
hydrocarbon groups
$C_1$-$C_{10}$ hydrocarbon
$C_1$-$C_5$ hydrocarbon
$C_1$-$C_3$ hydrocarbon.
alkyl groups
$C_1$-$C_{10}$ alkyl
$C_1$-$C_5$ alkyl
$C_1$-$C_3$ alkyl.

The hydrocarbyl/hydrocarbon/alkyl may be straight chain or branched and/or may be saturated or unsaturated.

The hydrocarbyl/hydrocarbon/alkyl may be straight or branched hydrocarbon groups containing at least one hetero atom in the group.

Oxyhydrocarbyl Group

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Each of the above teachings in respect of hydrocarbyl groups equally applies to the analogous oxyhydrocarbyl groups, that is the corresponding oxyhydrocarbyl group which comprises an oxygen in addition to the hydrocarbyl.

Typically, the oxyhydrocarbyl group is of the formula $C_{1-6}O$ (such as a $C_{1-3}O$).

Compound

In one preferred aspect the compound is of Formula II

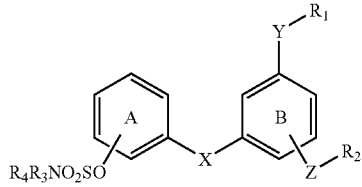

Formula II wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl; and ring A and B are independently optionally further substituted.

In one preferred aspect the compound is of Formula III

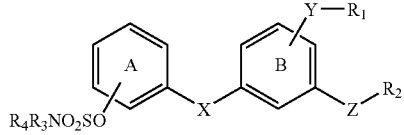

Formula III wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl; and ring A and B are independently optionally further substituted.

In one preferred aspect the compound is of Formula IIIa

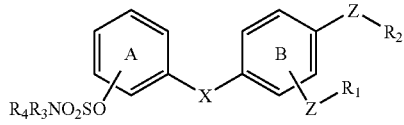

Formula IIIa wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl; and ring A and B are independently optionally further substituted.

In one preferred aspect the compound is of Formula IV

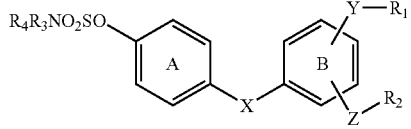

Formula IV wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl; and ring A and B are independently optionally further substituted.

In one preferred aspect the compound is of Formula V

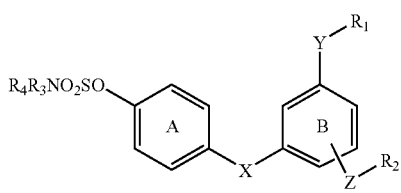

Formula V wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VI

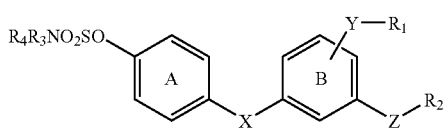

Formula VI wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VIa

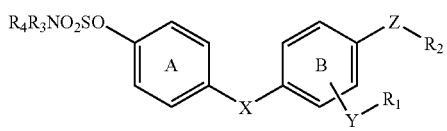

Formula VIa wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VII

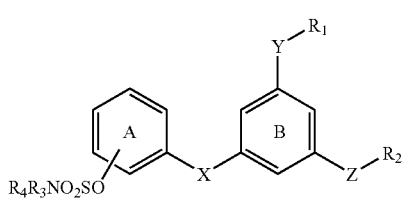

Formula VII wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VIIa

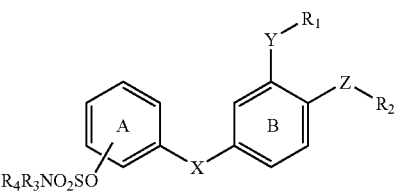

Formula VIIa wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VIII

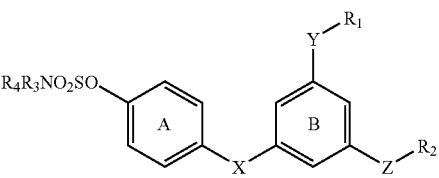

Formula VIII wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

In one preferred aspect the compound is of Formula VIIIa

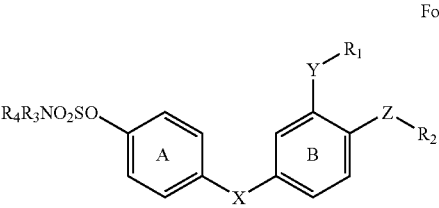

Formula VIIIa wherein X, Y and Z are each independently of each other an optional linker group; $R_1$ is a ring system; $R_2$ is selected from hydrocarbyl groups, oxyhydrocarbyl groups, cyano (—CN), nitro (—NO$_2$) and halogens; $R_3$ and $R_4$ are independently selected from H and hydrocarbyl; and ring A and B are independently optionally further substituted.

X, Y & Z

One of the more of the optional linker groups X, Y and Z may be present. In one aspect none of X, Y and Z are present.

In one preferred aspect at least one of the optional linker groups is present.

In one preferred aspect at least two of the optional linker groups are present.

In one preferred aspect each of X, Y and Z are present.

X

As discussed herein linker X is an optional group. In one aspect X is present. In one aspect X is not present. It will be appreciated by one skilled in the art that when X is not present rings A and B are linked via a bond. Thus when X is not present the present invention provides a compound of Formula Ia

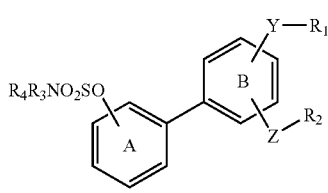

Formula Ia wherein X, Y and Z are each independently of each other an optional linker group; $R_1$ is a ring system; $R_2$ is selected from hydrocarbyl groups, oxyhydrocarbyl groups, cyano (—CN), nitro (—$NO_2$) and halogens; $R_3$ and $R_4$ are independently selected from H and hydrocarbyl; and ring A and B are independently optionally further substituted. The aspect wherein X is not present is applicable to each of the preferred aspects described herein for example the aspect shown in preferred Formulae II to VIII.

Preferably X is selected from hydrocarbyl, oxyhydrocarbyl, COO, CO, S, O, SO, $SO_2$, NR, and $SO_2NR$, wherein R is selected from H and hydrocarbyl groups.

When X is a hydrocarbyl group or in the option that X may be a hydrocarbyl group, preferably the hydrocarbyl group is a straight of branched alkyl group.

When X is a hydrocarbyl group or in the option that X may be a hydrocarbyl group, preferably the hydrocarbyl group is a straight chain alkyl group.

When X is a oxyhydrocarbyl group or in the option that X may be a oxyhydrocarbyl group, preferably the oxyhydrocarbyl group is —O-alkyl-, wherein alkyl is a straight of branched alkyl group.

When X is a oxyhydrocarbyl group or in the option that X may be a oxyhydrocarbyl group, preferably the oxyhydrocarbyl group is —O-alkyl-, wherein alkyl is a straight chain alkyl group In one preferred aspect X is selected from groups selected from $(CH_2)n$, CH=CH (preferably trans configuration), $O(CH_2)n$, $(CH_2)nO$, $S(CH_2)n$, $(CH_2)nS$, $CO(CH_2)n$, $(CH_2)nCO$, $CONH(CH_2)n$, $(CH_2)nCONH$, $COO(CH_2)n$, $(CH_2)nCOO$, $SO(CH_2)n$, $(CH_2)nSO$, $SO_2(CH_2)n$, $(CH_2)nSO_2$, $SO_2NC_{1-6}alkyl(CH_2)n$ (such as $SO_2NMe(CH_2)n$), $(CH_2)nSO_2NC_{1-6}alkyl$ (such as $(CH_2)nSO_2NMe$); $SO_2NH(CH_2)n$, and $(CH_2)nSO_2NH$; wherein n is independently an integer from 0 to 6. Preferably n is independently an integer from 1 to 6, more preferably from 1 to 3, such as 1, 2 or 3.

In one preferred aspect X is selected from groups selected from $(CH_2)n$, $O(CH_2)n$, $(CH_2)nO$, $S(CH_2)n$, $(CH_2)nS$, $CO(CH_2)n$, $(CH_2)nCO$, $CONH(CH_2)n$, $(CH_2)nCONH$, $COO(CH_2)n$, $(CH_2)nCOO$, $SO(CH_2)n$, $(CH_2)nSO$, $SO_2(CH_2)n$, $(CH_2)nSO_2$, $SO_2NH(CH_2)n$, and $(CH_2)nSO_2NH$; wherein n is independently an integer from 0 to 6. Preferably n is independently an integer from 1 to 6, more preferably from 1 to 3, such as 1, 2 or 3.

In one preferred aspect X is selected from groups selected from $SO_2NH$, $SO_2NMe$, $CONH$, $OCH_2$, $SCH_2$, and CH=CH (preferably trans configuration).

Y

In one preferred aspect Y is selected from hydrocarbyl, oxyhydrocarbyl, COO, CO, S, O, SO, $SO_2$, NR, and $SO_2NR$, wherein R is selected from H and hydrocarbyl groups.

In one preferred aspect Y is selected from hydrocarbyl, CO, and $SO_2$.

When Y is a hydrocarbyl group or in the option that Y may be a hydrocarbyl group, preferably the hydrocarbyl group is a straight of branched alkyl group.

When Y is a hydrocarbyl group or in the option that Y may be a hydrocarbyl group, preferably the hydrocarbyl group is a straight chain alkyl group.

In one preferred aspect Y is selected from groups selected from $(CH_2)m$, $CO(CH_2)m$, $(CH_2)mCO$, $SO_2(CH_2)m$ and wherein m is independently an integer from 0 to 6. Preferably m is independently an integer from 1 to 6, more preferably from 1 to 3, such as 1, 2 or 3.

In a highly preferred aspect Y is $(CH_2)m$, wherein m is an integer from 0 to 6, preferably an integer from 1 to 6, more preferably from 1 to 3, such as 1, 2 or 3. In a highly preferred aspect Y is —$CH_2$—.

Z

In one preferred aspect Z is selected from hydrocarbyl, oxyhydrocarbyl, COO, CO, S, O, SO, $SO_2$, NR, and $SO_2NR$, wherein R is selected from H and hydrocarbyl groups.

In one preferred aspect Z is a hydrocarbyl group.

When Z is a hydrocarbyl group or in the option that Z may be a hydrocarbyl group, preferably the hydrocarbyl group is a cycloalkyl group. Preferably the cycloalkyl group is a C 3 to 10 cycloalkyl, preferably a C 3 to 6 cycloalkyl, most preferably a C3 or C4 cycloalkyl.

When Z is a hydrocarbyl group or in the option that Z may be a hydrocarbyl group, preferably the hydrocarbyl group is a straight of branched alkyl group.

When Z is a hydrocarbyl group or in the option that Z may be a hydrocarbyl group, preferably the hydrocarbyl group is a branched alkyl group.

In one preferred aspect Z is $CpH_2p$, wherein p is an integer from 1 to 6. Preferably p is independently an integer from 1 to 3, such as 1, 2 or 3.

In one preferred aspect Z is a branched alkyl group of the formula $CpH_2p$ and comprising at least one —$C(CH_3)_2$— moiety, wherein p is an integer from 1 to 6, preferably from 1 to 3, such as 1, 2 or 3.

In one preferred aspect Z is a —$C(CH_3)_2$— group.

In one preferred aspect Z is selected from —$C(CH_3)_2$—, —C(O)O—,

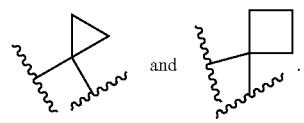

The ring system of R1 need not be a cyclic structure. In this regard, the ring system may be a linear structure that may have the ability to conform to a ring like structure when in in vivo. However in preferred aspects R1 is a cyclic structure.

R1 may be a heterocyclic group (a heterocycle) or a non-heterocyclic group. Suitable hetero atoms of a heterocyclic group include N, S and O.

When hetero atoms are present in a ring system to provide a heterocyclic group, the hetero atoms may be present in any amount. In one preferred aspect R1 is a ring system comprising carbon and one or more hetero atoms selected from N, S and O.

R1 may be is a saturated ring structure or an unsaturated ring structure (such as an aryl group).

Preferably, R1 is an aryl ring.

In one aspect of the invention R1 is selected from substituted or unsubstituted aromatic rings.

In one aspect R1 may be a polycyclic group, which need not be a fused polycycle. The term "polycyclic" includes fused and non-fused ring structures including combinations thereof. If the ring system of R1 is polycyclic some or all of the ring components of the ring system may be fused together or joined via one or more suitable spacer groups.

The ring size of R1 may be chosen by one skilled in the art to achieve compounds having desired activity. Typically R1 is a ring system comprising from 3 to 10 members, such as ring systems comprising from 5, 6 or 7 members.

Heterocyclic ring systems for use in the present invention include imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a highly preferred aspect R1 is selected from triazole, in particular 1H-1,2,3-triazole, 1H-1,2,4-triazole, 4H-1,2,4-triazole In a highly preferred aspect R1 is 1H-1,2,4-triazole.

In a highly preferred aspect $R_1$ is

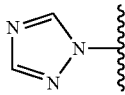

R1 may be substituted by one or more substituents. Typical substituents include hydrocarbyl, oxyhydrocarbyl, halo and cyano (—C≡N) groups. R1 may also be substituted by one or more substituents selected from phosphonate groups, thiophosphonate groups, sulphonate groups and sulphonamide groups.

In one preferred aspect R1 is unsubstituted.

—Y—R1

In a highly preferred Y is —CH$_2$— and R1 is

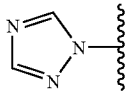

Thus in this aspect —Y—R1 together are the group

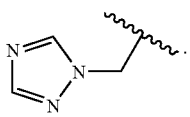

In one preferred aspect $R_2$ is selected from hydrocarbyl groups, oxyhydrocarbyl groups, cyano (—CN), nitro (—NO$_2$) and halogens, wherein the hydrocarbyl group is a straight of branched alkyl group.

When R2 is a hydrocarbyl group or in the option that R2 may be a hydrocarbyl group, preferably the hydrocarbyl group is a straight chain alkyl group.

When R2 is a hydrocarbyl group or in the option that R2 may be a hydrocarbyl group, preferably the hydrocarbyl group is (CH$_2$)qCH$_3$, wherein q is an integer from 0 to 6. Preferably q is an integer from 0 to 3, such as 0, 1, 2 or 3.

In one preferred aspect $R_2$ is selected from hydrocarbyl groups, oxyhydrocarbyl groups, cyano (—CN), nitro (—NO$_2$) and halogens, wherein the oxyhydrocarbyl group is —O-alkyl-, wherein alkyl is a straight or branched alkyl group.

When R2 is a oxyhydrocarbyl group or in the option that R2 may be a oxyhydrocarbyl group, preferably the oxyhydrocarbyl group is —O-alkyl-, wherein alkyl is a straight chain alkyl group When R2 is a oxyhydrocarbyl group or in the option that R2 may be a oxyhydrocarbyl group, preferably the oxyhydrocarbyl group is —O(CH$_2$)rCH$_3$, wherein r is an integer from 0 to 6. Preferably r is an integer from 0 to 3, such as 0, 1, 2 or 3.

In a highly preferred aspect $R_2$ is selected from —CH$_3$, —OCH$_3$, cyano (—CN), nitro (—NO$_2$) and halogens. The halogen may be selected from F, Cl, Br and I.

In a highly preferred aspect $R_2$ is selected from —CH$_3$, and —CN.

—Z—R2

In a highly preferred Z is selected from —C(CH$_3$)$_2$—, —C(O)O—,

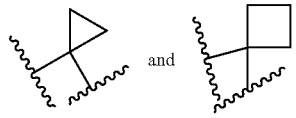

or may be absent and R$_2$ is selected from —CH$_3$, and —CN.

Thus in this aspect —Z—R2 together may be selected from —C(CH$_3$)$_2$—CN, —C(O)O—CN, —CN,

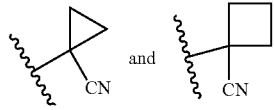

R3 & R4

In one preferred aspect $R_3$ and $R_4$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

In one preferred aspect at least one of $R_3$ and $R_4$ is H.

In one preferred aspect $R_3$ is H and $R_4$ is H.

Rings A & B

As noted herein the compounds of the present invention may comprise other substituents. These other substituents may, for example, further increase the activity of the compounds of the present invention and/or increase stability (ex vivo and/or in vivo). For example the ring denoted A and B in the general formulae may comprise other substituents. However in one preferred aspect rings A and B are independently not further substituted.

In one aspect neither ring A nor ring B is further substituted.

In one aspect ring A is further substituted.

In one aspect ring B is further substituted.

In one preferred aspect ring A is further substituted and ring B is not further substituted.

If ring A and/or ring B is further substituted, the further substitution may be by groups selected from hydrocarbyl groups, oxyhydrocarbyl groups, cyano (—CN), nitro (—NO$_2$) and halogens.

C1-6 alkyl groups, C1-6 alkoxy groups, cyano (—CN), nitro (—NO$_2$) and halogens.

—CH$_3$, —CH$_2$CH$_3$, —OCH$_3$, cyano (—CN), nitro (—NO$_2$) and halogens.

If ring A is further substituted, the further substitution is preferably a halogen and in particular, Cl, Br and/or F.

If ring A is further substituted, preferably ring A is substitution by only one further substituent, that is preferably a halogen and in particular, Cl, Br and/or F.

If ring A is further substituted, preferably the further substituent is at a position on the ring ortho to the sulphamate group.

Thus in one preferred aspect of the present invention, there is provided a compound of Formula Ib Formula Ib

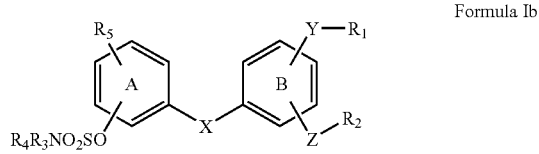

wherein X, Y and Z are each independently of each other an optional linker group; R$_1$ is a ring system; R$_2$ is selected from hydrocarbyl groups, oxyhydrocarbyl groups, cyano (—CN), nitro (—NO$_2$) and halogens; R$_3$ and R$_4$ are independently selected from H and hydrocarbyl; wherein R5 is selected from hydrocarbyl groups, oxyhydrocarbyl groups, cyano (—CN), nitro (—NO$_2$) and halogens, and ring A and B are not further substituted.

Preferably R5 is selected from C1-6 alkyl groups, C1-6 alkoxy groups, cyano (—CN), nitro (—NO$_2$) and halogens. More preferably R5 is selected from —CH$_3$, —CH$_2$CH$_3$, —OCH$_3$, cyano (—CN), nitro (—NO$_2$) and halogens. More preferably R5 is selected from Cl, Br and F.

Thus in one preferred aspect of the present invention, there is provided a compound of Formula Ic Formula Ic

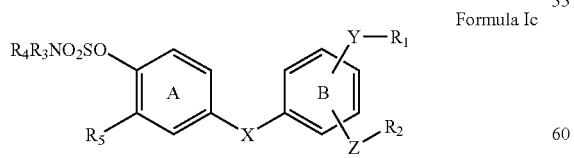

wherein R$_5$ is as described herein.

Further Preferred Compounds

In one preferred aspect the compound of the present invention may be selected from compounds of one of the formulae below. In the formulae below each ring may be substituted or unsubstituted or may contain one or more additional bonds in the ring.

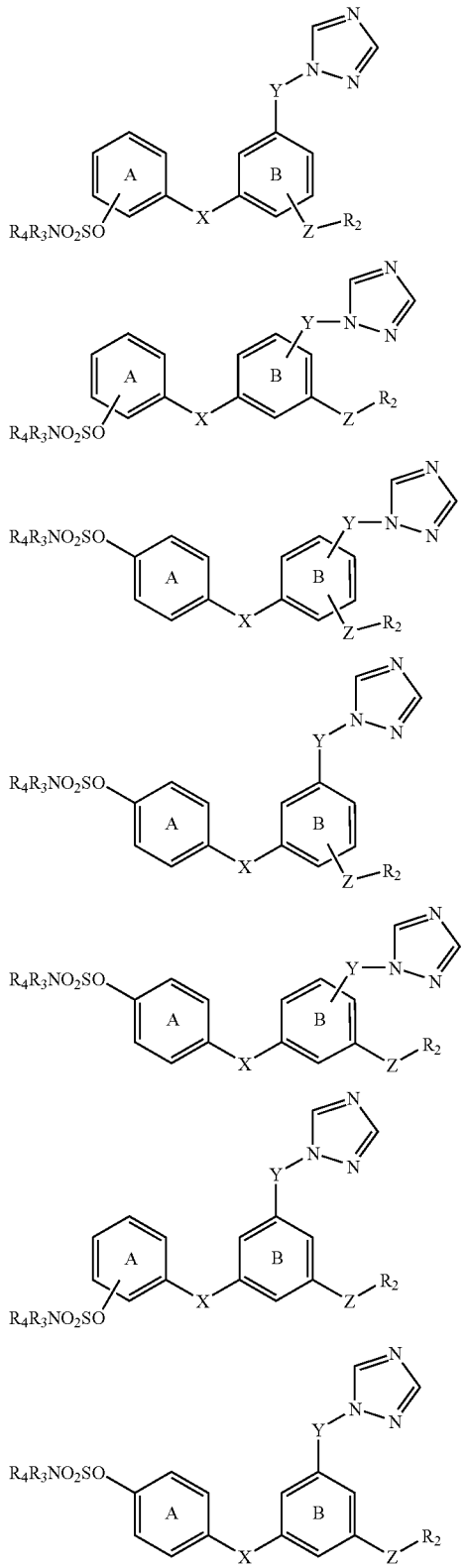

In one preferred aspect the compound of the present invention may be selected from compounds of the formula

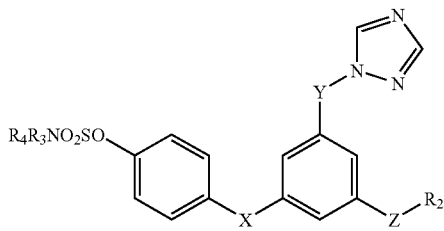

wherein X is selected from groups selected from (CH₂)n, CH=CH (preferably trans configuration), O(CH₂)n, (CH₂)nO, S(CH₂)n, (CH₂)nS, CO(CH₂)n, (CH₂)nCO, CONH(CH₂)n, (CH₂)nCONH, COO(CH₂)n, (CH₂)nCOO, SO(CH₂)n, (CH₂)nSO, SO₂(CH₂)n, (CH₂)nSO₂, SO₂NC₁₋₆ alkyl(CH₂)n (such as SO₂NMe(CH₂)n), (CH₂)nSO₂NC₁₋₆ alkyl (such as (CH₂)nSO₂NMe); SO₂NH(CH₂)n, and (CH₂)nSO₂NH;; wherein n is independently an integer from 0 to 6, wherein Y is selected from groups selected from (CH₂)m, CO(CH₂)m, (CH₂)mCO, SO₂(CH₂)m and wherein m is independently an integer from 0 to 6;

wherein Z is selected from CpH₂p, C(O)O and C3 to 6 cycloalkyl groups, wherein p is an integer from 1 to 6; and wherein R₂ is selected from —CH₃, —OCH₃, cyano (—CN), nitro (—NO₂) and halogens.

In one preferred aspect the compound of the present invention may be selected from compounds of the formula

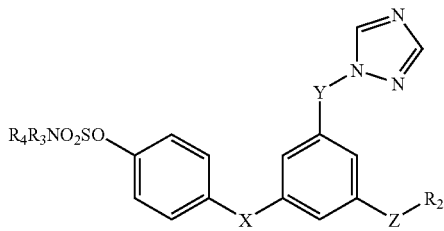

wherein X is selected from groups selected from (CH₂)n, O(CH₂)n, (CH₂)nO, S(CH₂)n, (CH₂)nS, CO(CH₂)n, (CH₂)nCO, CONH(CH₂)n, (CH₂)nCONH, COO(CH₂)n, (CH₂)nCOO, SO(CH₂)n, (CH₂)nSO, SO₂(CH₂)n, (CH₂)nSO₂, SO₂NH(CH₂)n, and (CH₂)nSO₂NH; wherein n is independently an integer from 0 to 6, wherein Y is selected from groups selected from (CH₂)m, CO(CH₂)m, (CH₂)mCO, SO₂(CH₂)m and wherein m is independently an integer from 0 to 6;

wherein Z is CpH₂p, wherein p is an integer from 1 to 6; and wherein R₂ is selected from —CH₃, —OCH₃, cyano (—CN), nitro (—NO₂) and halogens.

A preferred compound of the present invention is a compound selected from compounds of the formulae

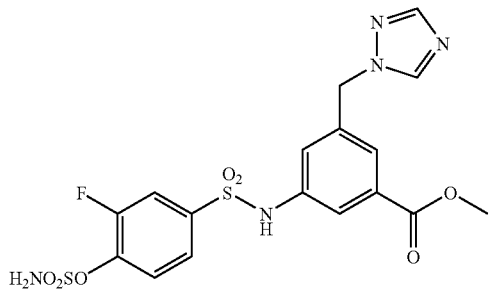

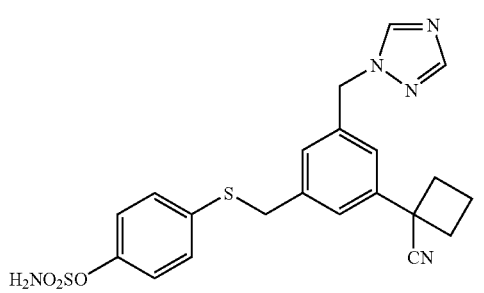

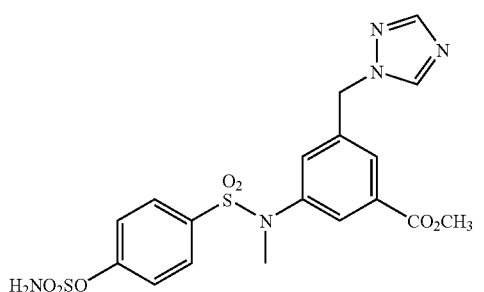

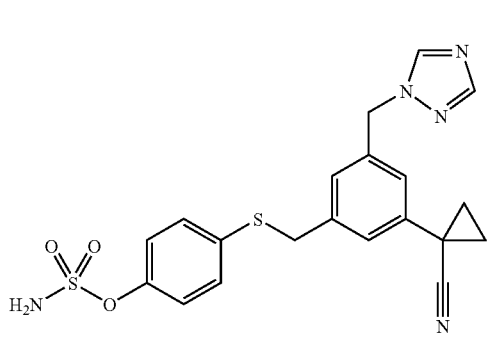

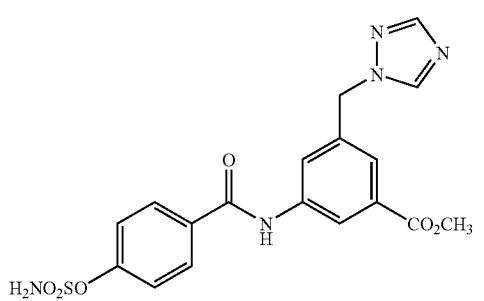

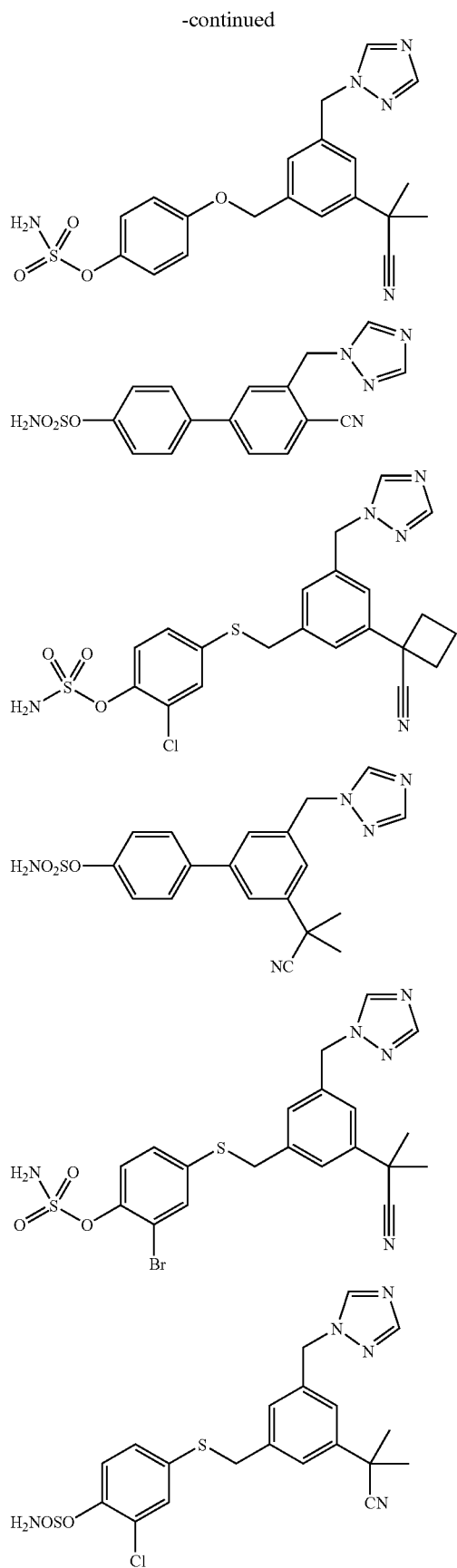

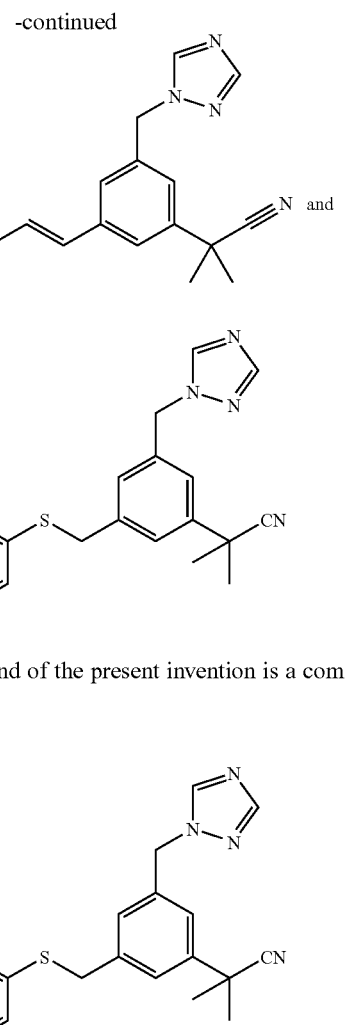

A preferred compound of the present invention is a compound of the formula

Other Aspects

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention and metabolites of the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Sulphatase

Steroid sulphatase—which is sometimes referred to as steroid sulphatase or steryl sulphatase or "STS" for short— hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis— may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity.

Sulphamate Group

The term "sulphamate" as used herein includes an ester of sulphamic acid, or an ester of an N-substituted derivative of sulphamic acid, or a salt thereof.

If $R^3$ is a sulphamate group then the compound of the present invention is referred to as a sulphamate compound.

Typically, the sulphamate group has the formula:

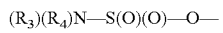

wherein preferably $R_3$ and $R_4$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms.

When $R_3$ and/or $R_4$ is hydrocarbyl, the preferred values are those where $R_3$ and $R_4$ are each independently selected $C_1$-$C_{10}$ hydrocarbyl, $C_1$-$C_5$ hydrocarbyl, $C_1$-$C_3$ hydrocarbyl, $C_1$-$C_{10}$ hydrocarbon, $C_1$-$C_5$ hydrocarbon, $C_1$-$C_3$ hydrocarbon, $C_1$-$C_{10}$ alkyl, $C_1$-$C_5$ alkyl and $C_1$-$C_3$ alkyl.

When $R_3$ and/or $R_4$ is alkyl, the preferred values are those where $R_3$ and $R_4$ are each independently selected from lower alkyl groups containing from 1 to 6 carbon atoms, that is to say methyl, ethyl, propyl etc. $R_3$ and $R_4$ may both be methyl.

When $R_3$ and/or $R_4$ is aryl, typical values are phenyl and tolyl (PhCH$_3$; o).

Where $R_3$ and/or $R_4$ represent cycloalkyl, typical values are cyclopropyl, cyclopentyl, cyclohexyl etc.

When joined together $R_3$ and $R_4$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on ring A.

In some embodiments, there may be more than one sulphamate group. By way of example, there may be two sulphamates (i.e. bis-sulphamate compounds).

In some preferred embodiments, at least one of $R_3$ and $R_4$ is H.

In some further preferred embodiments, each of $R_3$ and $R_4$ is H.

Other Substituents

The compound of the present invention may have substituents other than those of formula I. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

Assay for Determining STS Activity Using Cancer Cells

Protocol 1

Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465-4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1\times10^5$ cells/flask using the above medium. Cells are grown to 80% confluency and the medium is changed every third day.

Intact monolayers of JEG3 cells in triplicate 25 cm$^2$ tissue culture flasks are washed with Earle's Balanced Salt Solution (EBSS from ICN Flow, High Wycombe, U.K.) and incubated for 3-4 hours at 37° C. with 5 pmol ($7\times10^5$ dpm) [6,7-3H] oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7\times103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 2

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C]oestrone ($7\times103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3

Inhibition of Oestrone Sulphatase Activity in vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity Protocol 5

The ability of compounds to inhibit oestrone sulphatase activity can also be assessed using amino acid sequences or nucleotide sequences encoding STS, or active fragments, derivatives, homologues or variants thereof in, for example, high-through put screens. Such assays and methods for their pratice are taught in WO 03/045925 which is incorporated herein by reference.

In one preferred aspect, the present invention relates to a method of identifying agents that selectively modulate STS, which compounds have the formula (I).

Assay for Determining Aromatase Activity Using JEG3 Cells

Protocol 6

Aromatase activity is measured in JEG3 choriocarcinoma cells, obtained from the ATCC. This cell line possesses significant aromatase activity and is widely used to study the control of human aromatase activity (Bhatnager et al., J. Steroid Biochem. Molec. Biol. 2001, 76: 199-202). Cells are maintained in Minimal Essential Medium (MEM, Flow Laboratories, Irvine, Scotland) containing 20 mM HEPES, 10% foetal bovine serum, 2 mM glutamine, non-essential amino acids and 0.075% sodium bicarbonate. Intact monolayers of JEG3 cells ($2.5 \times 10^6$ cells) in triplicate 25 $cm^2$ tissue culture flasks are washed with Earle's Balanced salt solution (EBSS, from ICN Flow, High Wycombe, UK) and incubated with [1β-$^3$H] androstenedione (2-5 nM, 26 Ci/mmol, New England Nuclear, Boston, Mass., USA) for 30 min with inhibitors over the range of 10 pm-10 µM. During the aromatase reaction, $^3H_2O$ is liberated which can he quantified using a liquid scintillation spectrometer (Beckman-Coulter, High Wycombe, Bucks. UK). This $^3H_2O$-release method has been widely used to measure aromatase activity (Newton et al., J.Steroid Biochem. 1986,24: 1033-1039). The number of cell nuclei per flask is determined using a Coulter Counter after treating the cell monolayers with Z aponin.

Results for aromatase activity are expressed as the mean±1 S.D. of the product formed during the incubation period (30 min) calculated for $10^6$ cells and, for values showing a statistical significance, as a percentage reduction (inhibition) over incubations containing no aromatase inhibitor. Unpaired Student's t test was used to test the statistical significance of results. $IC_{50}$ values were calculated as the concentration of inhibitor required to obtain a 50% inhibition of aromatase activity.

Animal Assays for Determining Aromatase Activity

Protocol 7

(i) Inhibition of PMSG-induced Oestrogen Synthesis

The ability of compounds to inhibit aromatase activity in vivo was tested using a pregnant mare serum gonadotrophin (PMSG)-induced oestrogen synthesis assay. For this, female rats (250 g) were injected with PMSG (200 IU, s.c.). After 72 h rats were administered vehicle (propylene glycol) or various doses of test compounds orally. At 2 h after dosing blood samples were obtained by cardiac puncture (under anaesthesia). Plasma oestradiol levels were measured in control groups and groups receiving drugs. The efficacy of aromatase inhibition was determined by measurement of plasma oestradiol concentrations by radioimmunoassay. This method has been widely used to determine the effectiveness of aromatase inhibitors in vivo (Wouters et al., J.Steroid Biochem., 1989, 32: 781-788).

(ii) Inhibition of Androstenedione Stimulated Uterine Growth in Ovariectomised Rats Female rats (250 g) were ovariectomised and used to determine the effectiveness of aromatase inhibition on androstenedione stimulated uterine growth. Administration of androstenedione (30 mg/kg/d) for a 2-week period results in a significant increase in uterine growth in ovariectomised animals. This increase in uterine growth is stimulated by oestrogen which is derived from the administered androstenedione as a result of the action of the aromatase enzyme. By co-administration of compounds with androstenedione the extent of aromatase inhibition can be determined by measurements of uterine weights in treated and untreated animals.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling;

and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 7

Procedure

Stage 1

MCF-7 breast cancer cells are seeded into multi-well culture plates at a density of 105 cells/well. Cells were allowed to attach and grown until about 30% confluent when they are treated as follows:

Control—No Treatment

Compound of Interest (COI) 20 μM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER-) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodegenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent antithrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other otorhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R_3R_4NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

SUMMARY

In summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

EXAMPLES

The present invention will now be described in further detail by way of example only with reference to the accompanying figure in which.

Figure 1:
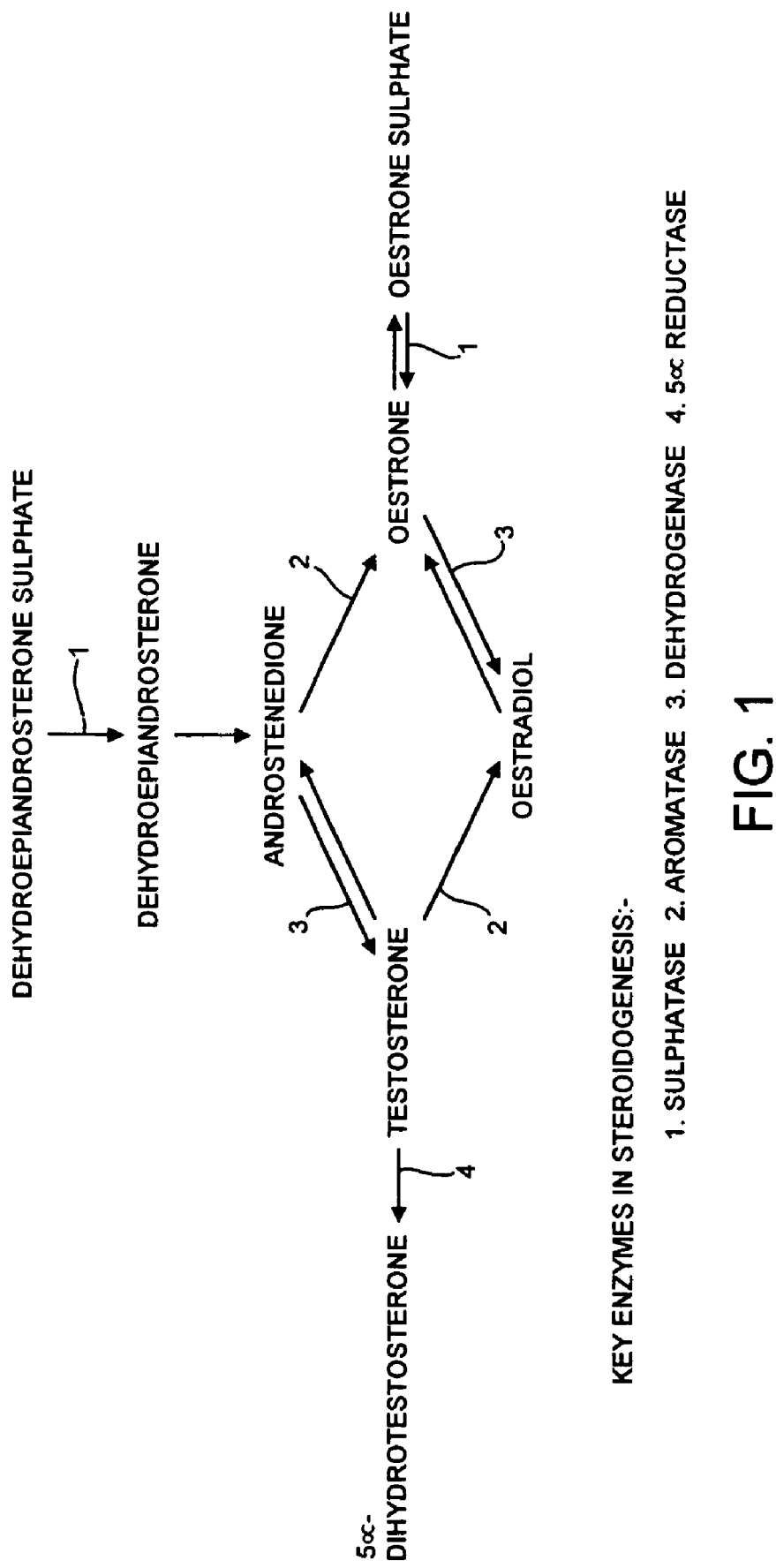
FIG. 1 shows a summary scheme.
Figure 2:
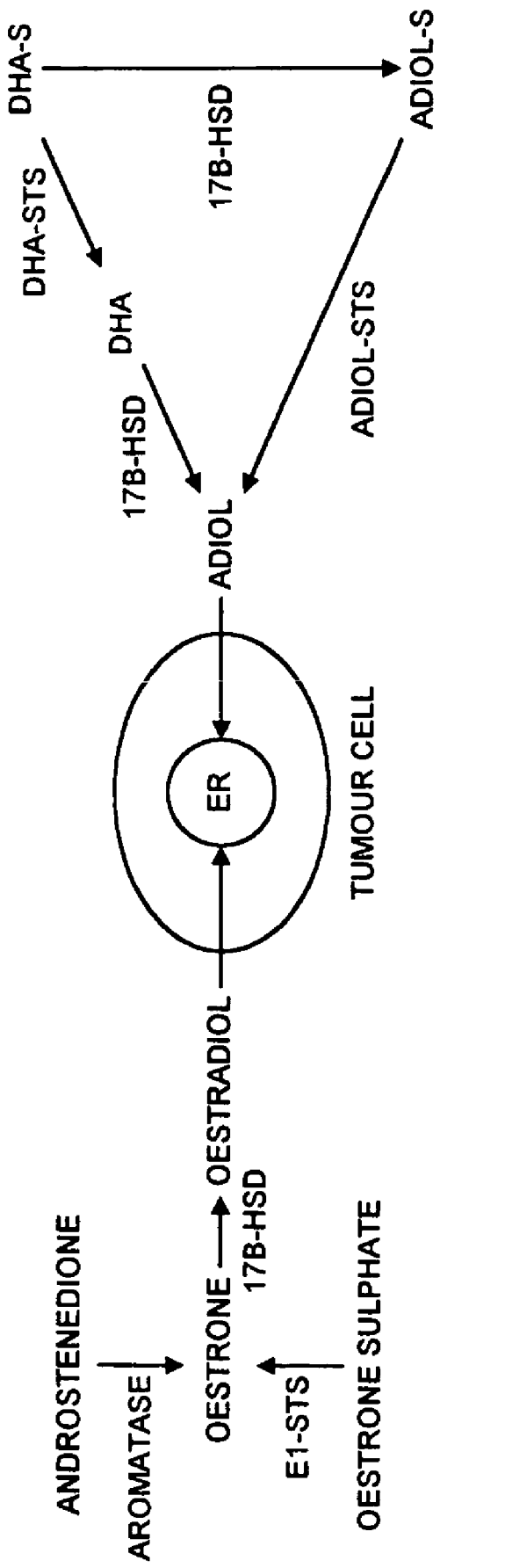
FIG. 2 shows a summary scheme.

The present invention will now be described only by way of example. However, it is to be understood that the examples also present preferred compounds of the present invention, as well as preferred routes for making same and useful intermediates in the preparation of same.

Synthetic Routes

Compounds in accordance with the present invention were synthesised in accordance with the synthetic routes and schemes.

The present invention will now be described only by way of example. However, it is to be understood that the examples also present preferred compounds of the present invention, as well as preferred routes for making same and useful intermediates in the preparation of same.

Synthetic Routes

Compounds in accordance with the present invention were synthesised in accordance with the synthetic routes and schemes.

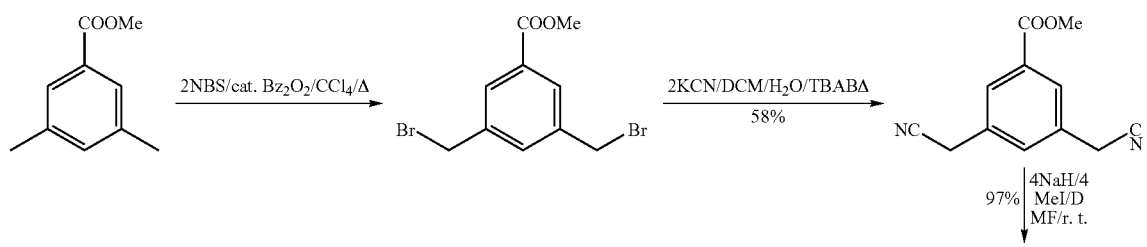

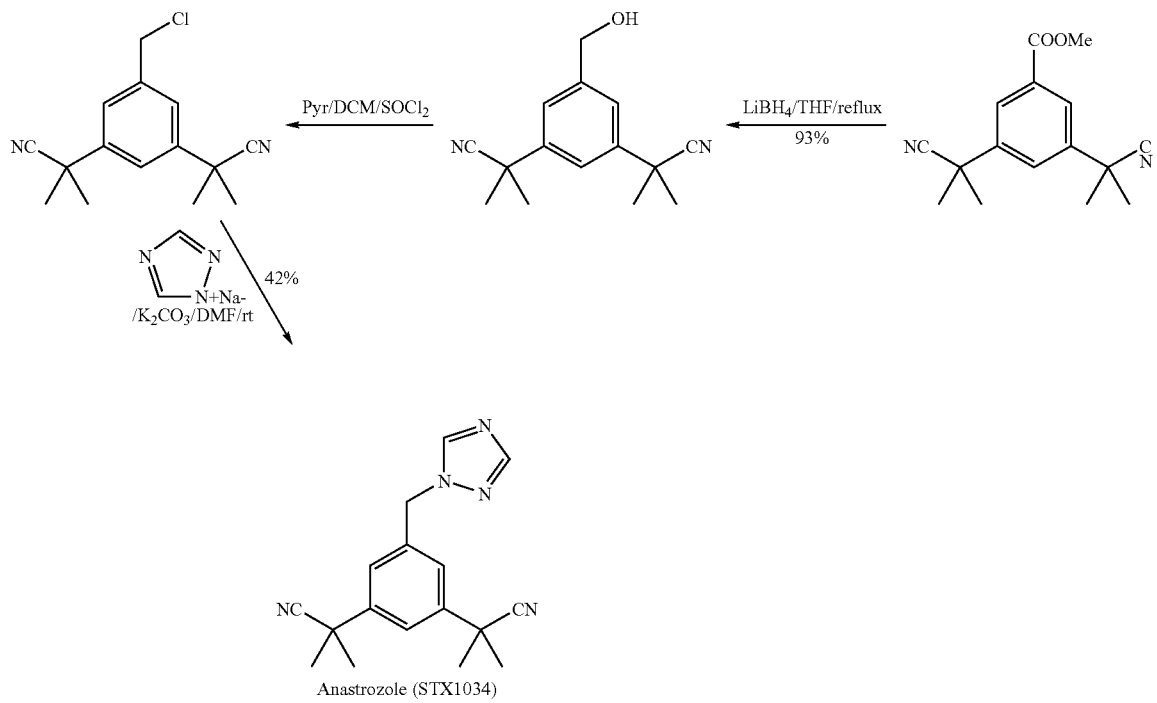

Anastrozole (STX1034)

Scheme. Synthesis of Anastrozole

3-Bromomethyl-5-methyl-benzoic acid methyl ester (LWO03036B) and 3,5-Bis-bromomethyl-benzoic acid methyl ester (LWO03036C)

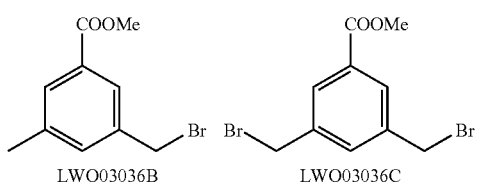

To a solution of methyl 3,5-dimethylbenzoate (15.0 g, 89.52 mmol) in carbon tetrachloride (molecular sieves 4 Å dried, 150 mL) was added finely powdered N-bromosuccinimide (16.1 g, 89.52 mmol) and benzoyl peroxide (≧97%, 200 mg). The light yellow suspension was then refluxed which turned into a light orange suspension after about 10 min. When the colour of the suspension returned to light yellow again about 45 min later, the reflux was terminated. After cooling to room temperature, the suspension was filtered and the filter cake collected was washed with ether (5×30 mL). The combined filtrates were evaporated to give a clear bright yellow liquid (22.9 g) which was fractionated by flash chromatography (silica: 700 g; eluent: ethyl acetate/hexane, 1:10 to 1:1). The second fraction that collected upon evaporation gave LWO03036B as a translucent pale yellow oil (13.32 g, 54.79 mmol, 61%) whereas the third fraction gave LWO03036C as white fluffy needle-shaped crystals (1.99 g, 3.08 mmol, 7%).

LWO03036B:

$R_f$: 0.27 (ethyl acetate/hexane, 1:8), c.f. 0.39 (S.M.)

$\delta_H$ (270 MHz, CDCl$_3$) 2.39 (3H, s, Ar—CH$_3$), 3.90 (3H, s, COOMe), 4.47 (2H, s, CH$_2$Br), 7.39 (1H, slightly broad s, Ar), 7.78 (1H, slightly broad s, Ar) and 7.85 (1H, s, Ar).

LRMS (FAB+): 443.3 (17), 398.3 [25, (M$^{81}$Br+H+NBA)+], 243.1 [100, (M$^{79}$Br+H)$^+$], 163.1 [83, (M$^{79}$Br−$^{79}$Br)$^+$], 85.1 (54).

HRMS (FAB+): 243.00124 C$_{10}$H$_{12}$O$_2$Br requires 243.00207

LWO03036C:

$R_f$: 0.20 (ethyl acetate/hexane, 1:8), c.f. 0.39 (S.M.) m.p. 100-103° C. [Lit.[1] (from column), 95-97° C.] [1] Liu P, Chen Y, Deng J, Tu Y. An efficient method for the preparation of benzylic bromides. Synthesis 2001, 14: 2078-2080.

$\delta_H$ (400 MHz, CDCl$_3$) 3.93 (3H, s, OCH$_3$), 4.49 (4H, s, 2×CH$_2$), 7.60 (1H, t, J~1.7 Hz, C4-H) and 7.97 (2H, d, J~2.0 Hz, C2-H and C6-H).

3,5-Bis-cyanomethyl-benzoic acid methyl ester (LWO03041A)

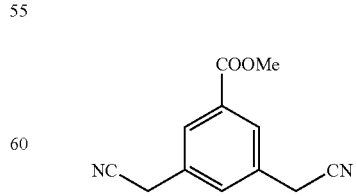

A mixture of LWO03036C (1.96 g, 6.081 mmol), LWO03015C (913 mg, 2.835 mmol), potassium cyanide (1.45 g, 21.40 mmol), tetrabutylammonium bromide (100 mg) in dichloromethane (15 mL) and water (5 mL) was refluxed with vigorous stirring for 4 h. After removal of volatile solvent, the concentrated mixture was diluted with ethyl acetate (50 mL). The organic layer was washed with brine (100 mL, 4×50 mL), dried (MgSO$_4$), filtered and evaporated to give a golden yellow syrup which on standing at room temperature solidified to a yellow mass. This crude product was fractionated by flash chromatography (silica: 80 g; eluent: ethyl acetate/hexane, 1:1) and the fourth fraction that isolated upon evaporation gave LWO03041A as white residue (1.11 g, 5.182 mmol, 58%);

$R_f$: 0.41 (ethyl acetate/hexane, 1:1), c.f. 0.78 (S.M.)

m.p. 91-93° C. [Lit. (Patent: EP0296749A1, 90-92° C. (CCl$_4$)];

$\delta_H$ (270 MHz, CDCl$_3$) 3.82 (4H, s, 2×CH$_2$), 3.95 (3H, s, COOMe), 7.53 (1H, s, ArH) and 7.99 (2H, s, 2×ArH).

Found: C 67.1, H 4.74, N 13.0%. C$_{12}$H$_{10}$N$_2$O$_2$ requires C 67.28, H 4.71, N 13.08%.

3,5-Bis-(cyano-dimethyl-methyl)-benzoic acid methyl ester (LWO03043)

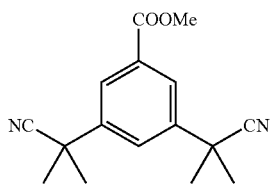

To a solution of LWO03041A (1.09 g, 5.088 mmol) in anhydrous DMF (20 mL) at ice/water temperature was added cautiously sodium hydride (60% in mineral oil, 896 mg, 22.39 mmol) in four portions. After stirring at this temperature under an atmosphere of nitrogen for 15 min, methyl iodide (1.39 mL, 22.39 mmol) was introduced and the resulting suspension was stirred at room temperature overnight. The light orange suspension obtained was diluted with ethyl acetate (50 mL) and the organic layer washed with brine (200 mL, 5×50 mL), dried (MgSO$_4$), filtered and evaporated to give a yellow/brown syrup. This crude product was fractionated by flash chromatography (silica: 90 g; eluent: ethyl acetate/hexane, 1:1) and the main fraction that isolated upon evaporation gave a bright yellow syrup which on standing at room temperature solidified to give LWO03043 as creamy wax (1.33 g, 4.920 mmol, 97%). A small amount of this wax (535 mg) was dissolved in hot cyclohexane (~3 mL). Upon cooling of the mixture a light yellow oil was initially separated which solidified to a creamy mass at room temperature.

$R_f$: 0.65 (ethyl acetate/hexane, 1:1), c.f. 0.46 (S.M.)

m.p. 85-87° C. [Lit. (Patent: EP0296749A1, 83-85° C. (CCl$_4$)];

$\delta_H$ (270 MHz, CDCl$_3$) 1.77 (12H, s, 4×Me), 3.95 (3H, s, COOMe), 7.80 (1H, t, J~1.8 Hz, C4-H) and 8.08 (2H, d, J 2 Hz, C2-H and C6-H).

Found: C 71.1, H 6.78, N 10.3%. C$_{16}$H$_{18}$N$_2$O$_2$ requires C 71.09, H 6.71, N 10.36%.

2-[3-(Cyano-dimethyl-methyl)-5-hydroxymethyl-phenyl]-2-methyl-propionitrile (LWO03044, LWO03049A)

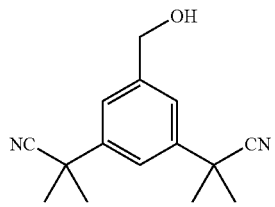

To a mixture of LWO03043 (516 mg, 1.909 mmol) and lithium borohydride (88 mg, 3.817 mmol) at room temperature was added anhydrous THF (10 mL). The resulting clear pale yellow solution was refluxed under an atmosphere of nitrogen for 3 h, then cooled to ice/water temperature and treated dropwise (cautiously) with 1 M hydrochloric acid until the mixture remained acidic. Ethyl acetate (100 mL) was added and the organic layer was washed with brine (100 mL, 4×50 mL), dried (MgSO$_4$), filtered and evaporated to give LWO03049 as a white residue (460 mg, 1.898 mmol, 99.5%).

$R_f$: 0.23 (ethyl acetate/hexane, 1:1), c.f. 0.48 (S.M.)

m.p. 150-160° C. [Lit. (Patent: EP0296749A1, 151-153° C.];

$\delta_H$ (270 MHz, CDCl$_3$) 1.75 (12H, s, 4×Me), 4.76 (2H, s, CH$_2$O), 7.44 (2H, br s, ArH) and 7.46 (1H, d, J 1.7 Hz, ArH).

LHMS (FAB+): 501.3 (5), 485.3 [24, (2M+H)$^+$], 467.3 [35, (2M+H−H$_2$O)$^+$], 396.2 [24, (M+H+NBA)$^+$], 378.2 [22, (M+H+NBA−H$_2$O)$^+$], 272.1 (8), 247.2 (43), 225.1 [100, (M+H−H$_2$O)$^+$].

LHMS (FAB−): 708.5 (20), 619.4 (30), 571.4 (18), 556.5 (25), 495.3 (31), 482.3 (35), 467.3 (27), 420.4 (26), 395.4 [100, M+NBA)$^−$], 331.2 (43).

HRMS (FAB+): 396.19317, C$_{22}$H$_{26}$N$_3$O$_4$ (M+H+NBA) requires 396.19233.

HRMS (FAB+): 225.14394, C$_{15}$H$_{17}$N$_2$ (M+H−H$_2$O) requires 225.13917.

LWO03049 contained about 3-5% w/w of starting material (the ester) and was used without further purification.

2-[3-(Cyano-dimethyl-methyl)-5-[1,2,4]triazol-1-ylmethyl-phenyl]-2-methyl-propionitrile (LWO03051A, Anastrozole, STX1034)(c.f. LWO03045)

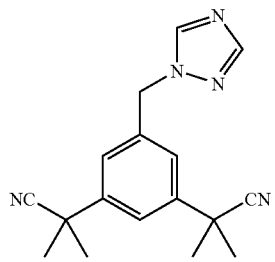

To a solution of LWO03049 (418 mg, 1.725 mmol) in anhydrous dichloromethane (15 mL) at ice/water temperature under an atmosphere of nitrogen was added anhydrous pyridine (0.15 mL, 1.897 mmol) followed by thionyl chloride (0.19 mL, 2.588 mmol). The reaction mixture was stirred at ice/water temperature for 15 min and then at room temperature for 2 h before subjecting to reflux for 1 h. After cooling, the reaction mixture was evaporated and the white residue obtained in ethyl acetate (30 mL) was washed with brine (3×30 mL). The organic layer was dried (MgSO$_4$), filtered and evaporated to give a pale yellow residue (473 mg, LWO03050). To a solution of this residue in anhydrous DMF (4 mL) at ice/water temperature was added 1,2,4-triazole, sodium derivative (367 mg, 3.628 mmol). The resulting light brown suspension was stirred at room temperature under an atmosphere of nitrogen for 18 h. Ethyl acetate (30 mL) was added to dilute the reaction mixture and the organic layer was washed with brine (50 mL, 3×30 mL), dried (MgSO$_4$), filtered and evaporated to give a light yellow brown syrup (438 mg). This crude product was fractioned by flash chromatography (silica: 15 g; eluent: ethyl acetate) and the second fraction that isolated upon evaporation gave a light yellow glue which upon standing for weeks at room temperature solidified to give LWO03051 as creamy pale yellow wax (279 mg, 951 μmol, 52%).

$R_f$: 0.33 (ethyl acetate), c.f. 0.62 (LWO03049).

m.p. 59-62° C. [Lit. (Patent: EP0296749A1, 81-82° C. (ethyl acetate/cyclohexane)];

$δ_H$ (270 MHz, CDCl$_3$) 1.71 (12H, s, 4×Me), 5.39 (2H, s, CH$_2$), 7.32 (2H, two s, C4-H and C6-H), 7.53 (1H, t, J 1.7 Hz, C2-H), 7.80 (1H, s, C3'-H) and 8.14 (1H, s, C5'-H).

Found: C 69.6, H 6.38, N 23.9%. C$_{17}$H$_{19}$N$_5$ requires C 69.60, H 6.53, N 23.87%.

Scheme. Synthesis of Anastrozole-based DASI (STX1023)

3-Bromomethyl-5-methyl-benzoic acid methyl ester (LWO03015B) and 3,5-Bis-bromomethyl-benzoic acid methyl ester (LWO03015C)

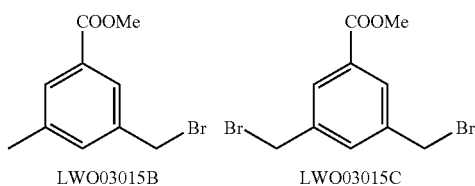

To a solution of methyl 3,5-dimethylbenzoate (5.57 g, 33.24 mmol) in carbon tetrachloride (molecular sieves 4 Å dried, 50 mL) was added finely powdered N-bromosuccinimide (5.98 g, 33.24 mmol) and benzoyl peroxide (≧97%, 100 mg). The light yellow suspension was then refluxed which turned into a light orange suspension after about one hour. When the colour of the suspension returned to light yellow again about 30 min later, the reflux was terminated. After cooling to room temperature, the suspension was filtered and the filter cake collected was washed with ether (5×30 mL). The combined filtrates were evaporated to give a clear bright

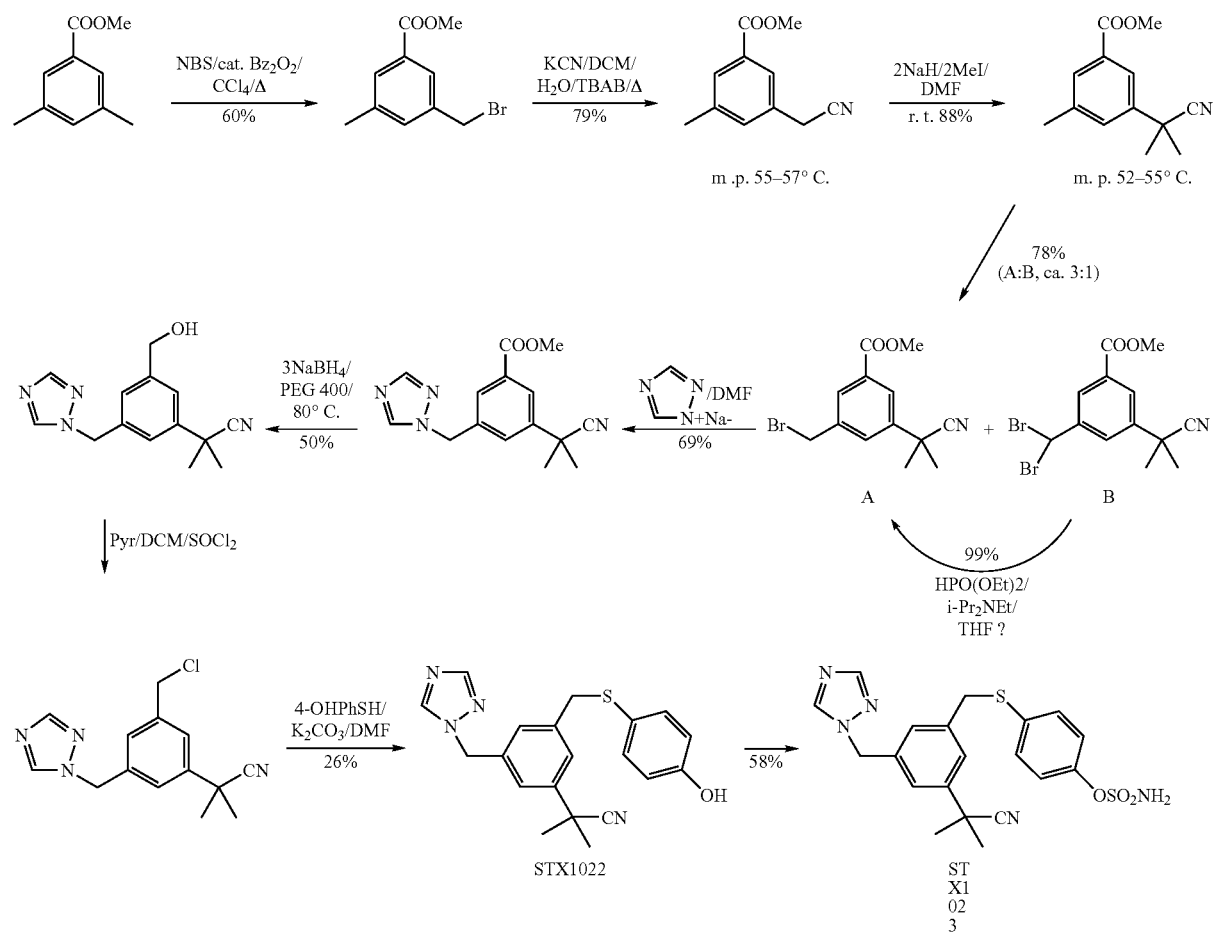

yellow liquid (8.15 g) which was fractionated by flash chromatography (silica: 300 g; eluent: ethyl acetate/hexane, 1:10; flow rate: ca. 30 mL/min). The first fraction collected was the starting material (998 mg). The second and third fractions collected were respectively LWO03015B as a translucent pale yellow oil (4.90 g, 20.16 mmol, 61%) and LWO03015C as white fluffy needle-shaped crystals (990 mg, 3.08 mmol, 9%).

LWO03015B $R_f$: 0.27 (ethyl acetate/hexane, 1:8), c.f. 0.39 (S.M.)

$\delta_H$ (270 MHz, CDCl$_3$) 2.39 (3H, s, Ar—CH$_3$), 3.90 (3H, s, COOMe), 4.47 (2H, s, CH$_2$Br), 7.39 (1H, slightly broad s, Ar), 7.78 (1H, slightly broad s, Ar) and 7.85 (1H, s, Ar).

LRMS (FAB+): 443.3 (17), 398.3 [25, (M$^{81}$Br+H+NBA)$^+$], 243.1 [100, (M$^{79}$Br+H)$^+$], 163.1 [83, (M$^{79}$Br−$^{79}$Br)$^+$], 85.1 (54).

HRMS (FAB+): 243.00124 C$_{10}$H$_{12}$O$_2$Br requires 243.00207.

LWO03015C $R_f$: 0.20 (ethyl acetate/hexane, 1:8), c.f. 0.39 (S.M.)

m.p. 100-103° C. [Lit.[1] (from column), 95-97° C.] [1] Liu P, Chen Y, Deng J, Tu Y. An efficient method for the preparation of benzylic bromides. Synthesis 2001, 14: 2078-2080.

$\delta_H$ (400 MHz, CDCl$_3$) 3.93 (3H, s, OCH$_3$), 4.49 (4H, s, 2×CH$_2$), 7.60 (1H, t, J∼1.7 Hz, C4-H) and 7.97 (2H, d, J∼2.0 Hz, C2-H and C6-H).

3-Cyanomethyl-5-methyl-benzoic acid methyl ester (LWO03016B)

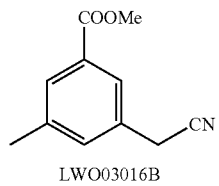

LWO03016B

A mixture of LWO03015B (3.0 g, 12.34 mmol), potassium cyanide (1.0 g, 14.81 mmol), tetrabutylammonium bromide (100 mg) in dichloromethane (15 mL) and water (5 mL) was refluxed with vigorous stirring for 4 h. After removal of volatile solvent, the concentrated mixture was diluted with ethyl acetate (100 mL). The organic layer was washed with brine (100 mL, 4×50 mL), dried (MgSO$_4$), filtered and evaporated to give a light yellow/brown syrup which upon standing at room temperature solidified to a yellow mass (2.48 g). This crude product was fractionated by flash chromatography (silica: 100 g; eluent: ethyl acetate/hexane, 1:4, then 1:2 after collection of the first fraction). The second fraction that isolated upon evaporation gave LWO03016B as an almost colourless syrup which upon standing at room temperature solidified into a mass of white wax (1.84 g, 9.725 mmol, 79%);

$R_f$: 0.20 (ethyl acetate/hexane, 1:4), c.f. 0.44 (S.M.);

m.p. 55-57° C.;

$\delta_H$ (270 MHz, CDCl$_3$) 2.41 (3H, s, CH$_3$), 3.75 (2H, s, CH$_2$), 3.93 (3H, s, OCH$_3$), 7.35 (1H, s, ArH), 7.78 (1H, s, ArH) and 7.82 (1H, s, ArH).

LRMS (FAB+): 496.1 [6, (M+H+2NBA)$^+$], 343.1 [32, (M+H+NBA)$^+$], 190.1 [100, (M+H)$^+$], 158.1 [22, (M−OMe)$^+$].

HRMS (FAB+): 190.08651 C$_{11}$H$_{12}$NO$_2$ requires 190.08680.

Found: C 69.4, H 5.87, N 7.19%. C$_{11}$H$_{11}$NO$_2$ requires C 69.83, H 5.86, N 7.40%.

3-(Cyano-dimethyl-methyl)-5-methyl-benzoic acid methyl ester (LWO03017A)

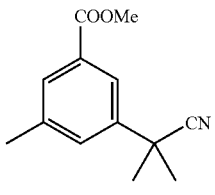

LWO03017A

To a solution of LWO03016B (1.72 g, 9.075 mmol) in anhydrous DMF (20 mL) at ice/water temperature was added cautiously sodium hydride (60% in mineral oil, 800 mg, 19.96 mmol) in four portions. After stirring at this temperature under an atmosphere of nitrogen for 15 min, methyl iodide (2.83 g, 19.96 mmol) was introduced and the resulting suspension was stirred at room temperature overnight. The light orange suspension obtained was diluted with ethyl acetate (100 mL) and the organic layer washed with brine (200 mL, 4×50 mL), dried (MgSO$_4$), filtered and evaporated to give a light orange/brown syrup (2.30 g). This crude product was fractionated by flash chromatography (silica: 90 g; eluent: ethyl acetate/hexane, 1:4) and the first fraction that isolated upon evaporation gave a pale yellow syrup which upon standing at room temperature solidified to give LWO03017A as a mass of white wax (1.74 g, 8.009 mmol, 88%).

$R_f$: 0.32 (ethyl acetate/hexane, 1:4), c.f. 0.21 (S.M.)

m.p. 51.5-55° C.;

$\delta_H$ (270 MHz, CDCl$_3$) 1.73 (6H, s, 2×Me), 2.42 (3H, s, Ar—CH$_3$), 3.91 (3H, s, COOMe), 7.52 (1H, s, ArH), 7.80 (1H, s, ArH) and 7.88 (1H, s, ArH).

Found: C 72.1, H 6.98, N 6.48%. C$_{13}$H$_{15}$NO$_2$ requires C 71.87, H 6.96, N 6.45%.

3-Bromomethyl-5-(cyano-dimethyl-methyl)-benzoic acid methyl ester (LWO03023C and LWO03025)

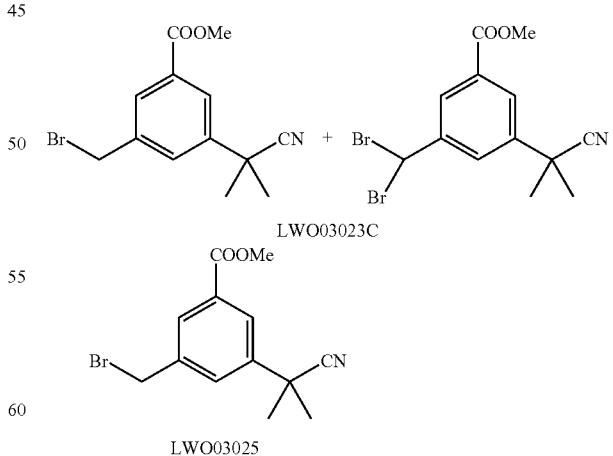

To a solution of LWO03017A (1.68 g, 7.733 mmol) in carbon tetrachloride (molecular sieves 4 Å dried, 20 mL) was added finely powdered N-bromosuccinimide (1.39 g, 7.733 mmol) and benzoyl peroxide (≧97%, 30 mg). The light yellow suspension was then refluxed which turned into a light orange suspension after about one hour. When the colour of the suspension returned to light yellow again about 1 h later, the reaction mixture was cooled to room temperature, filtered and the filter cake collected washed with ether (5×30 mL). The combined filtrates were evaporated to give a clear bright yellow syrup which was fractionated by flash chromatography (silica: 250 g; eluent: ethyl acetate/hexane, 1:6 to 1:4). The third collected upon evaporation gave a pale yellow syrup (LWO03023C, 1.79 g) which, according to $^1$H NMR, contained about 33% of 3-dibromomethyl-5-(cyano-dimethyl-methyl)-benzoic acid methyl ester in addition to the product.

$\delta_H$ (270 MHz, CDCl$_3$) 1.75 (6H, s, 2×Me), 1.77 (equiv of 2H, s), 3.93 (3H, s, COOMe), 3.95 (equiv of 1H), 4.51 (2H, s, CH$_2$Br), 6.67 (equiv of 0.5H, CHBr$_2$), 7.72 (1H, t, J<2 Hz, ArH), 7.87 (equiv of 0.5H), 8.02 (2H, broad s, 2×ArH), 8.07 (equiv of 0.5H, t, J<2 Hz) and 8.20 (equiv of 0.5H, vague t).

To a solution of LWO03023C (261 mg) in anhydrous THF (5 mL) at ice/water temperature under an atmosphere of nitrogen was added diethyl phosphite (243 mg, 1.762 mmol) and N-ethyl diisopropylamine (228 mg, 1.762 mmol). After stirring at room temperature for 14 h, the reaction mixture was poured onto ice and extracted with ethyl acetate (30 mL). The organic extract was further washed with 1M hydrochloric acid (50 mL) and then brine (3×50 mL), dried (MgSO$_4$) and evaporated to give LWO03025 as a pale yellow translucent syrup (285 mg, 962 µmol, 85%);

R$_f$: 0.21 (ethyl acetate/hexane, 1:4), c.f. 0.28 (S.M.)

$\delta_H$ (270 MHz, CDCl$_3$) 1.75 (6H, s, 2×Me), 3.93 (3H, s, COOMe), 4.51 (2H, s, CH$_2$Br), 7.72 (1H, t, J<2 Hz, ArH) and 8.02 (2H, broad s, 2×ArH).

LWO03025 still contained trace amount of the dibromide impurity but it was used without further purification.

3-Bromomethyl-5-(cyano-dimethyl-methyl)-benzoic acid methyl ester (LWO03028, c.f. LWO03025)

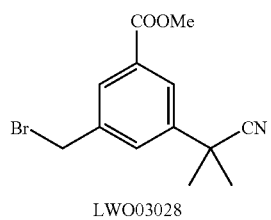

LWO03028

To a solution of LWO03023C (1.52 g) in anhydrous THF (30 mL) at ice/water temperature under an atmosphere of nitrogen was added diethyl phosphite (2.9 g, 20.57 mmol) and N-ethyl diisopropylamine (2.69 g, 20.57 mmol). After stirring at room temperature for 24 h, the reaction mixture was poured onto ice and extracted with ethyl acetate (50 mL). The organic extract was further washed with 1M hydrochloric acid (100 mL) and then brine (4×50 mL), dried (MgSO$_4$) and evaporated to give LWO03028 as a pale yellow translucent syrup (1.52 g, 5.132 mmol, 78%);

R$_f$: 0.21 (ethyl acetate/hexane, 1:4), c.f. 0.28 (S.M.)

$\delta_H$ (270 MHz, CDCl$_3$) 1.77 (6H, s, 2×Me), 3.94 (3H, s, COOMe), 4.52 (2H, s, CH$_2$Br), 7.71 (1H, t, J~1.7 Hz, ArH) and 8.02 (2H, m, 2×ArH).

3-(Cyano-dimethyl-methyl)-5-[1,2,4]triazol-1-ylm-ethyl-benzoic acid methyl ester (LWO03035)

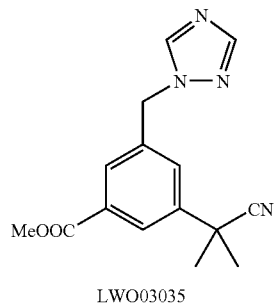

LWO03035

To a solution of LWO03028 (986 mg, 3.329 mmol) in anhydrous DMF (5 mL) at ice/water temperature was added 1,2,4-triazole, sodium derivative (1.35 g, 13.32 mmol). Under an atmosphere of nitrogen, the resulting suspension was stirred at room temperature for 18 h before it was diluted with ethyl acetate (30 mL). The organic layer was washed with brine (70 mL, 4×30 mL), dried (MgSO$_4$), filtered and evaporated to give a light yellow syrup (860 mg). This crude product was then purified by flash chromatography (silica: 50 g, eluent: ethyl acetate). The second fraction that collected gave a clear pale yellow glue (LWO03035, 667 mg, 2.346 mmol, 70%) which upon standing at room temperature for 15 min turned into a mass of white wax;

$\delta_H$ (270 MHz, CDCl$_3$) 1.73(6H, s, 2×Me), 3.92 (3H, s, COOMe), 5.41 (2H, s, CH$_2$N), 7.61 (1H, t, ArH), 7.86 (1H, s, ArH), 7.99 (1H, s, C3'-H), 8.08 (1H, t, J 1.5 Hz, ArH) and 8.14 (1H, s, C5'-H).

2-(3-Hydroxymethyl-5-[1,2,4]triazol-1-ylmethyl-phenyl)-2-methyl-propionitrile (LWO03037)

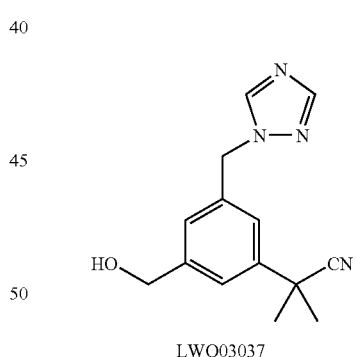

LWO03037

A mixture of LWO03035 (668 mg, 2.350 mmol), sodium borohydride powder (272 mg, 7.049 mmol) and PEG 400 (~8 g) was heated at 80° C. with stirring and swirling of flask for 18 h. After cooling, the syrup/glue was diluted and sonicated with ethyl acetate (30 mL). The organic layer was washed with 1M HCl (50 mL), basified with saturated sodium bicarbonate solution and then washed with brine (4×30 mL), dried (MgSO$_4$), filtered and evaporated to give LWO03037 as a light yellow residue (335 mg, 1.307 mmol, 56%).

R$_f$: 0.14 (ethyl acetate), c.f. 0.21 (S.M.);

$\delta_H$ (270 MHz, CDCl$_3$) 1.70 (6H, s, 2×Me), 1.97 (1H, t, J 5.5 Hz, OH), 4.71 (2H, d, J 5.4 Hz, CH$_2$O), 5.36 (2H, s, CH$_2$N), 7.19 (1H, s, ArH), 7.30 (1H, s, ArH), 7.45 (1H, s, ArH), 7.96 (1H, s, C3'-H) and 8.09 (1H, s, C5'-H).

2-[3-(4-Hydroxy-phenylsulfanylmethyl)-5-[1,2,4]triazol-1-ylmethyl-phenyl]-propionitrile [LWO03038→LWO03039 (STX1022)]

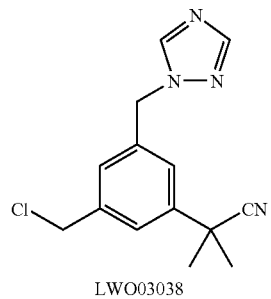

LWO03038

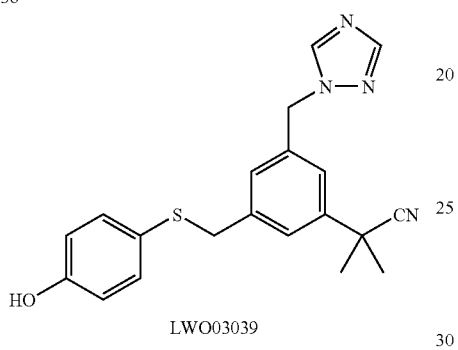

LWO03039

To a solution of LWO03037 (322 mg, 1.256 mmol) in anhydrous dichloromethane (15 mL) at ice/water temperature under an atmosphere of nitrogen was added anhydrous pyridine (0.15 mL, 1.884 mmol) followed by thionyl chloride (0.14 mL, 1.884 mmol). The reaction mixture was stirred at room temperature for 2 h and then refluxed for 1 h. After cooling and removal of volatile solvent, the brown oil that obtained in anhydrous DMF (5 mL) at room temperature and under an atmosphere of nitrogen was treated with finely-powdered potassium carbonate (1.74 g, 12.56 mmol) followed by a solution of 4-hydroxythiophenol (196 mg, 1.507 mmol) in anhydrous DMF (0.5 mL). The resulting yellow brown suspension was heated at 50° C. for 18 h and then diluted with ethyl acetate (40 mL). The organic layer was washed with brine (100 mL, 4×30 mL), dried (MgSO$_4$), filtered and evaporated to give a dark brown syrup (LWO03038, 635 mg). This crude product was fractionated by flash chromatography (silica: 70 g; eluent: ethyl acetate). The fourth fraction that isolated gave LWO03039 as a light yellow brown syrup (120 mg) which was further purified by eluting through an Isolute column (5 g) with ethyl acetate to give LWO03039B (90 mg, 247 µmol, 20%);

$R_f$: 0.38 (ethyl acetate), c.f. 0.38 (LWO03038);

$\delta_H$ (400 MHz, CDCl$_3$) 1.66 (6H, s, 2×Me), 3.87 (2H, s, CH$_2$S), 5.25 (2H, s, CH$_2$N), 6.68 (2H, AA'BB'), 6.74 (1H, s, ArH), 7.04 (2H, AA'BB'), 7.19 (1H, t, ArH), 7.24 (1H, t, ArH), 7.95 (1H, s, C3'-H) and 7.99 (1H, s, C5'-H) and 8.70 (1H, br s, OH).

LCMS (ES+): 365.1 [100, (M+H)$^+$], 296.0 [7, (M-triazole)$^+$], 269 (8); $t_R$=2.34 min.

HRMS (FAB+): 365.14410 C$_{20}$H$_{21}$N$_4$OS requires 365.14361.

2-[3-(4-Hydroxy-phenylsulfanylmethyl)-5-[1,2,4]triazol-1-ylmethyl-phenyl]-2-methyl-propionitrile (LWO03042, STX1023)

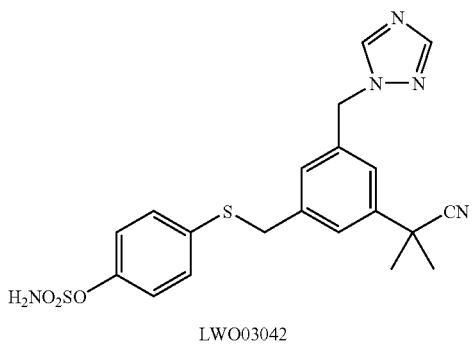

LWO03042

To a solution of LWO03039B (85 mg, 233.2 µmol) in anhydrous DMA (2 mL) at ice/water temperature was added a concentrated solution of sulphamoyl chloride in toluene (2 equiv). The resulting mixture was stirred under an atmosphere of nitrogen at room temperature for 18 h. After diluting with ethyl acetate (30 mL), the organic layer was washed with brine (70 mL, 5×25 mL), dried (MgSO$_4$), filtered and evaporated to give a light yellow brown glue (109 mg). This crude product was fractionated by flash chromatography (silica: 35 g, eluent: ethyl acetate) and the third fraction that isolated gave LWO03042 as a pale yellow glue (60 mg, 135.3 µmol, 58%).

$R_f$: 0.45 (ethyl acetate), c.f. 0.35(S.M.);

$\delta_H$ (400 MHz, CDCl$_3$) 1.73 (6H, s, 2×Me), 4.04 (2H, s, CH$_2$S), 5.25 (2H, s, CH$_2$N), 6.58 (1H, s, ArH), 6.87 (2H, s, OSO$_2$NH$_2$), 7.15 (4H, s, ArH×4), 7.23 (1H, s, ArH), 7.34 (1H, t, ArH), 7.57 (1H, s, C3'-H) and 7.85 (1H, s, C5'-H).

LCMS (ES+): 444.26 [100, (M+H)$^+$]; $t_R$=2.35 min.

HRMS (FAB+): 444.11707. C$_{20}$H$_{22}$N$_5$O$_3$S$_2$ requires 444.11641.

Synthesis of STX1528

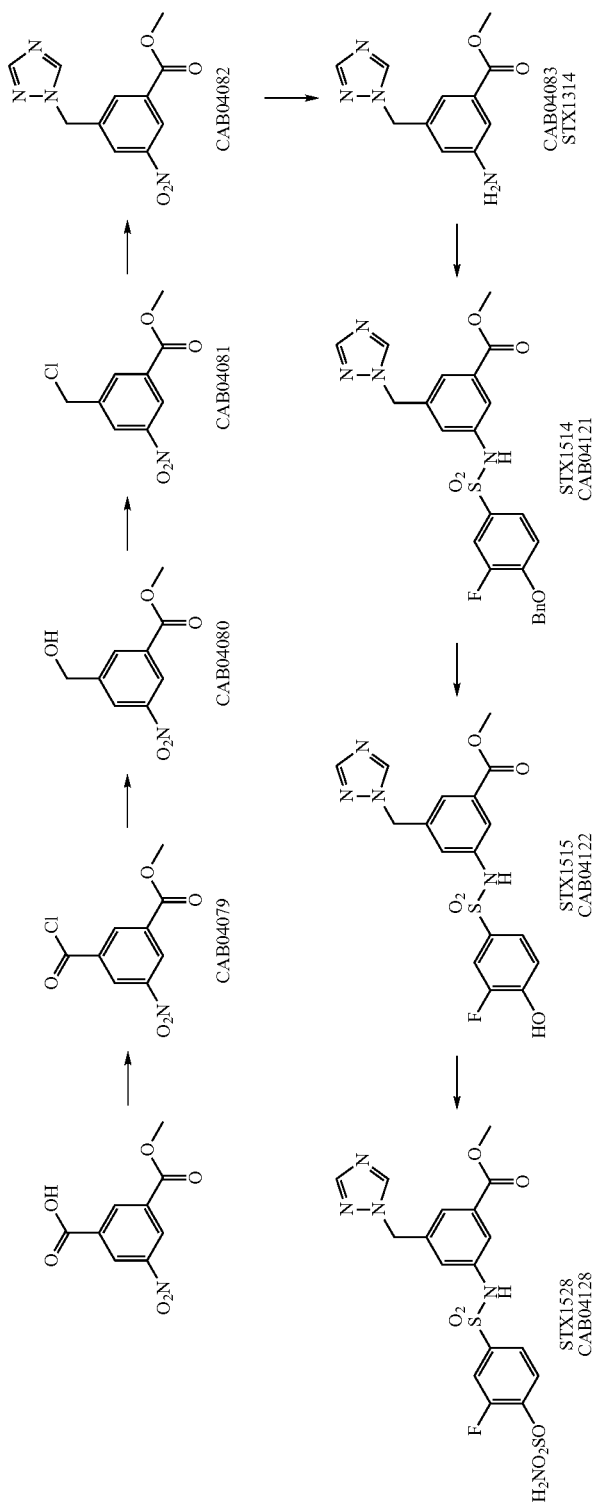

CAB04079

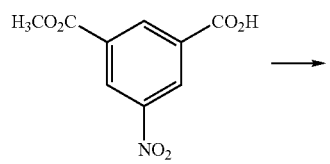

3-Chlorocarbonyl-5-nitro-benzoic acid methyl ester (CAB04079): A suspension of 5-nitro-isophtalic acid mono methyl ester (22.52 g, 100.0 mmol) in thionyl chloride (50 ml) was heated to reflux for 6 hours (until the production of SO$_2$ and HCl-gas ceased). The excess of thionyl chloride was removed under reduced pressure, the residue was dissolved in DCM and the product was precipitated by addition of hexane to give a white solid. Yield: 24.10 g (99%).

$^1$H-NMR (400 MHz, CDCl$_3$) δ 4.08 (3H, s, —OCH$_3$), 9.07 (1H, dd, J=1.7, 1.7 Hz), 9.12 (1H, dd, J=2.2, 1.7 Hz), 9.16 (1H, dd, 2.2, 1.7 Hz);

$^{13}$C-NMR (100.5 MHz, CDCl$_3$) δ 53.4 (OCH$_3$), 129.2, 130.0, 133.2, 135.4, 136.8, 148.7, 163.5, 166.1;

MS (FAB+): m/z 242.9 (100%, [C$_9$H$_6$ClNO$_5$]$^+$)

CAB04080

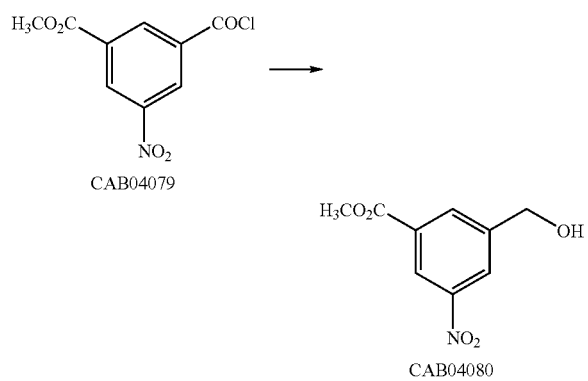

3-Hydroxymethyl-5-nitro-benzoic acid methyl ester (CAB04080): Sodium borohydride (1.892 g, 50.0 mmol) was added in small portions to EtOH (150 ml) at 0° C. (ice bath), then CAB04079 (12.18 g, 50.0 mmol) was added in small portions to the mixture. The solution turned dark red immediately and was stirred for 1 hour after the addition was complete. The reaction mixture was poured into crushed ice (ca. 300 g) and the crude product was extracted with EtOAc (3×100 ml). The organic layer was washed with water (100 ml) and brine (50 ml), dried over Na$_2$SO$_4$ and concentrated under reduced pressure. The residue was purified by column chromatography (EtOAc/hexane 1:3, R$_f$: 0.31) to give the title compound as a white solid.

Yield: 4.57 g (43%).

$^1$H-NMR (400 MHz, CDCl$_3$) δ 2.17 (1H, br s, —OH), 4.02 (3H, s, —OCH$_3$), 4.92 (2H, s, —CH$_2$OH), 8.39 (1H, m), 8.47 (1H, m), 8.79 (1H, m);

$^{13}$C-NMR (100.5 MHz, CDCl$_3$) δ 52.9 (OCH$_3$), 63.6, 123.5, 125.3, 132.0, 133.1 143.6, 165.0 (one carbon not resolved);

MS (FAB+): m/z 211.9 (100%, [C$_9$H$_9$NO$_5$]$^+$);

HPLC (ACS80) t$_r$=1.921 min (>99%).

CAB04081

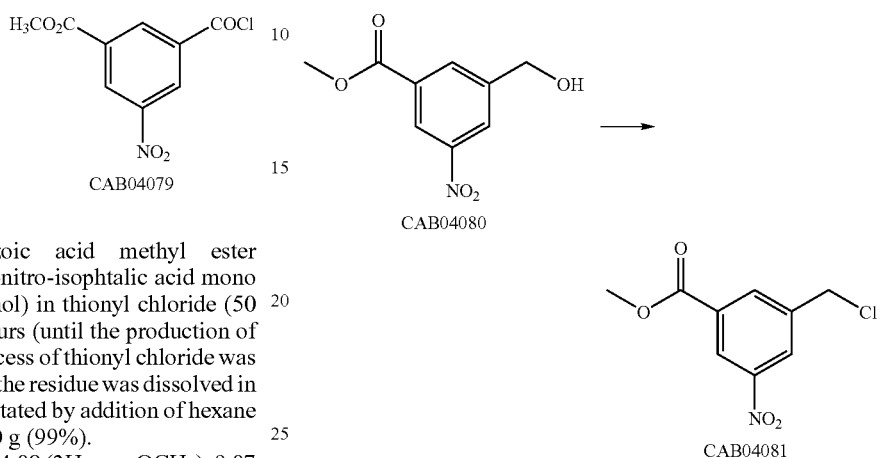

3-Chloromethyl-5-nitro-benzoic acid methyl ester (CAB04081): Thionyl chloride (5 ml) was added to a solution of CAB04080 (4.223, 20.0 mmol) in DCM. The dark solution was heated to reflux until the production gas ceased (ca. 30 min) and concentrated under reduced pressure. The residue was purified by column chromatography (EtOAc/hexane 1:5, R$_f$: 0.45) to give the title compound as a light yellow solid. Yield: 4.225 g (92%).

$^1$H-NMR (400 MHz, CDCl$_3$) δ 4.03 (3H, s, —OCH$_3$), 4.73 (2H, s, —CH$_2$Cl), 8.43 (1H, m), 8.49 (1H, dd, J=2.0, 2.0 Hz), 8.85 (1H, dd, J=2.0, 2.0 Hz);

$^{13}$C-NMR (100.5 MHz, CDCl$_3$) δ 44.1, 53.0 (OCH$_3$), 124.4, 127.3, 132.4, 135.1 140.6, 164.5 (one carbon not resolved);

MS (FAB+): m/z 229.9 (100%, [C$_9$H8ClNO$_4$]$^+$);

HPLC (ACS80) t$_r$=2.199 min (>99%).

STX1313 (CAB04082)

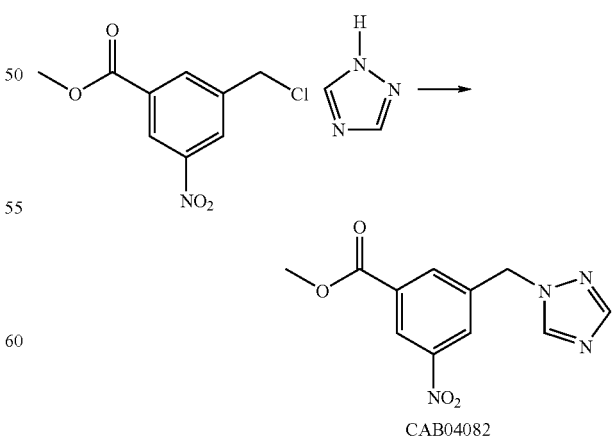

3-Nitro-5-[1,2,4]triazol-1-ylmethyl-benzoic acid methyl ester (CAB04082, STX1313): A mixture of CAB04081 (4.00 g, 17.4 mmol), 1,2,4-triazole (2.40 g, 34.8 mmol), K$_2$CO$_3$ (6.91 g, and sodium iodide (0.20 g, 1.33 mmol) in acetone (30 ml) was stirred vigorously for 24 hours at room temperature. EtOAc (100 ml) and water (50 ml) were added, the organic was separated, washed with water (50 ml) and brine (30 ml), dried over Na$_2$SO$_4$ and concentrated pressure. The residue was purified by column chromatography (EtOAc, R$_f$: 0.36) to give the title compound as a light yellow solid. Yield: 3.878 g (85%).

$^1$H-NMR (400 MHz, CDCl$_3$) δ 4.01 (3H, s, —OCH$_3$), 5.54 (2H, s, —CH$_2$—), 8.05 (1H, s), 8.27 (1H, s), 8.29 (1H, m), 8.35 (1H, dd, J=2.3, 1.8 Hz), 8.85 (1H, dd, J=2.0, 1.8 Hz);

$^{13}$C-NMR (100.5 MHz, CDCl$_3$) δ 52.1, 53.1, 124.7, 126.7, 132.7, 134.4, 137.5, 143.5, 148.7, 153.0, 164.4;

MS (FAB+): m/z 263.0 (100%, [C$_{11}$H$_{11}$N$_4$O$_4$]$^+$);

HRMS (FAB+) calcd for C$_{11}$H$_{11}$N$_4$O$_4$: 263.07803; found, 263.07846.

HPLC (ACS90) t$_r$=1.843 min (>99%).

STX1314 (CAB04083)

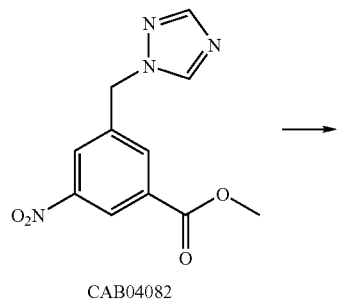

CAB04082

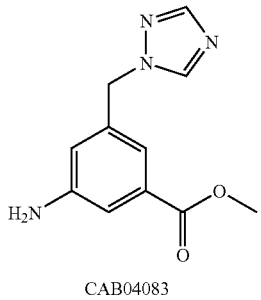

CAB04083

3-Amino-5-[1,2,4]triazol-1-ylmethyl-benzoic acid methyl ester (CAB04083, STX1314): Pd/C (100 mg, 5% Pd) was added to a solution of CAB04082 (1.311 g, 5.0 mmol) in EtOH (20 ml) and THF (20 ml). The resulting mixture was stirred under H$_2$-atmosphere for 24 hours. The Pd/C was removed by filtration through celite and the resulting clear solution was concentrated under reduced pressure. The residue was purified by column chromatography (EtOAc, R$_f$: 0.23) to give the title compound as a light yellow solid. Yield: 0.372 g (32%).

$^1$H-NMR (400 MHz, DMSO-d$_6$) δ 3.80 (3H, s, —OCH$_3$), 5.34 (2H, s, —CH$_2$—), 5.52 (2H, s, —NH$_2$), 6.66 (1 h, dd, J=2.0, 2.0 Hz), 7.01 (1H, dd, J=2.0, 2.0 Hz), 7.13 (1H, dd, J=2.0, 2.0 Hz), 8.01 (1H, s), 8.67 (1H,s);

$^{13}$C-NMR (100.5 MHz, DMSO-d$_6$) δ 52.3, 52.4, 114.2, 115.9, 117.6, 131.0, 138.0, 144.8, 149.8, 152.2, 166.9;

MS (FAB+): m/z 233.0 (100%, [C$_{11}$H$_{13}$N$_4$O$_2$]$^+$);

HRMS (FAB+) calcd for C$_{11}$H$_{13}$N$_4$O$_2$: 233.10385; found, 233.10318.

HPLC (ACS90) t$_r$=1.771 min (>99%).

STX1514 (CAB04121)

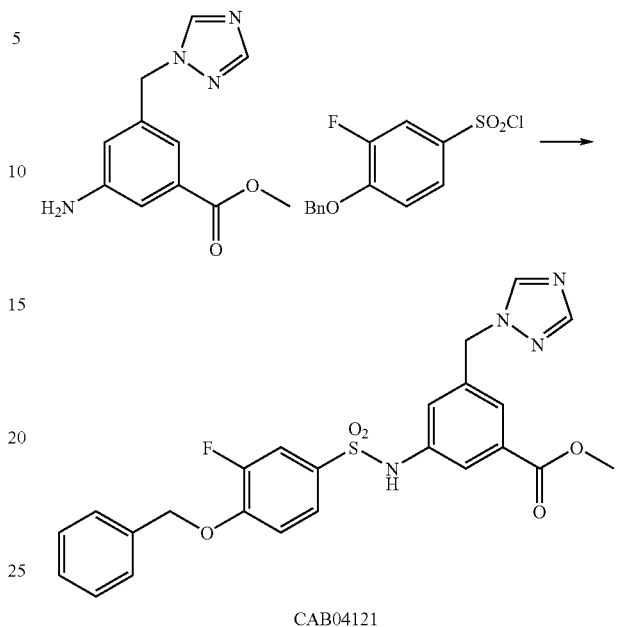

CAB04121

3-(4-Benzyloxy-3-fluoro-benzenesulfonylamino)-5-[1,2,4]triazol-1-ylmethyl-benzoic acid methyl ester (CAB04121): 4-Benzyloxy-3-fluoro-benzenesulfonyl chloride (301 mg, 1.0 mmol) was added to a solution of CAB04083 (232 mg, 1.0 mmol) in pyridine (5 ml). The mixture was stirred for 5 hours at room temperature, and then EtOAc (50 ml) and water (30 ml) were added. The organic layer was separated, washed with 2M KHSO$_4$ (2×30 ml) and brine (20 ml), dried over Na$_2$SO$_4$ and concentrated under reduced pressure. The residue was crystallized from EtOAc/hexane to give fine colorless needles. Yield: 457 mg (92%).

$^1$H-NMR (400 MHz, DMSO-d$_6$) δ 3.83 (3H, s, —OCH$_3$), 5.24 (2H, s), 5.47 (2H, s), 7.29-7.64 (11H, m), 8.02 (1H, s), 8.67 (1H, s), 10.62 (1H, s);

$^{13}$C-NMR (100.5 MHz, DMSO-d$_6$) δ 52.2, 52.8, 69.9, 115.0, 120.7, 123.8, 124.2, 127.0, 128.3, 128.5, 130.0, 130.7, 137.1, 138.0, 140.6, 144.9, 152.5, 161.7, 165.5, 166.3;

MS (AP+): m/z 497.3 (100%, [C$_{24}$H$_{22}$FN$_4$O$_3$S]$^+$);

HPLC (ACS80) t$_r$=1.893 min (97.8%).

STX1515 (CAB04122)

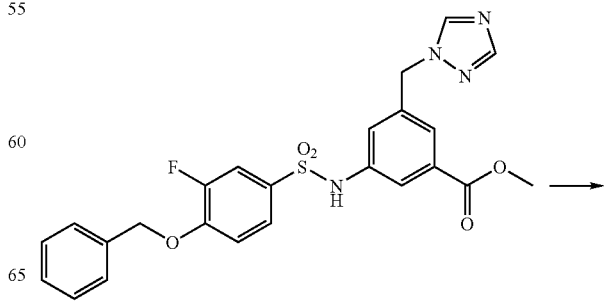

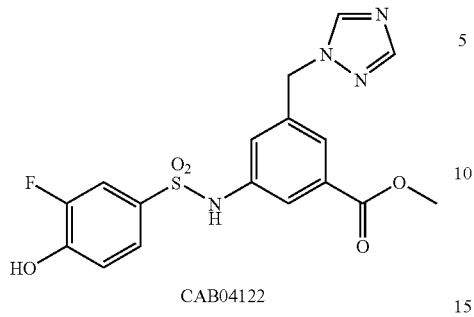

CAB04122

3-(3-Fluoro-4-hydroxy-benzenesulfonylamino)-5-[1,2,4]triazol-1-ylmethyl-benzoic acid methyl ester (CAB04122, STX1515): Pd/C (50 mg, 5%) was added to a solution of CAB04121 (298 mg, 0.60 mmol) in MeOH (10 ml) and THF (10 ml). The mixture was stirred under $H_2$-atmosphere at room temperature for 18 hours. The catalyst filtered off and the solution was concentrated under reduced pressure to give the title compound as white solid. Yield: 241 mg (99%).

$^1$H-NMR (270 MHz, DMSO-$d_6$) δ 3.79 (3H, s, —OCH$_3$), 5.47 (2H, s), 6.95-7.05 (1H, m), 7.27-7.58 (5H, m), 7.98 (1H, s), 8.63 (1H, s), 10.48 (1H, br s), 11.05 (1H, br s);

MS (AP−): m/z 405.2 (100%, [C$_{17}$H$_{14}$FN$_4$O$_5$S]$^−$);

HRMS (FAB+) calcd for C$_{17}$H$_{16}$FN$_4$O$_5$S: 407.08255; found, 407.08227.

HPLC (ACS80) $t_r$=1.793 min (92.1%).

STX1528 (CAB04128)

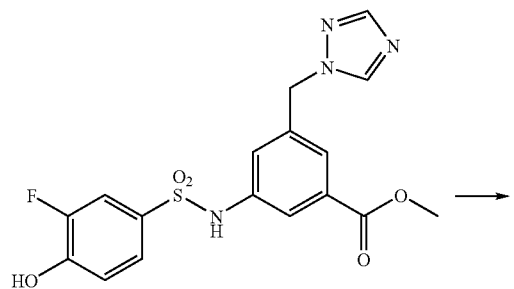

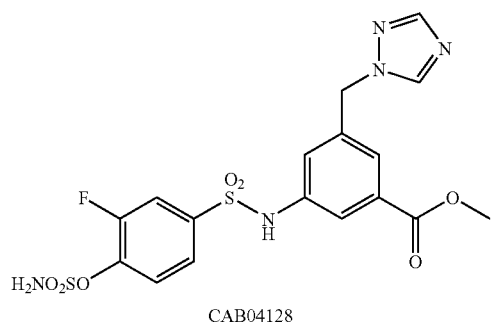

CAB04128

3-(3-Fluoro-4-sulfamoyloxy-benzenesulfonylamino)-5-[1,2,4]triazol-1-ylmethyl-benzoic acid methyl ester (CAB04128, STX1528): Sulphamoyl chloride solution in toluene (3 ml, 0.7 M, 2.1 mmol) was concentrated under reduced pressure. The residue was dissolved In DMA (5 ml) at 0° C. and CAB04122 (120 mg, 0.295 mmol) was added to the solution. Stirring was continued for 18 hours, EtOAc (50 ml) and water 30 ml were added, the organic layer was separated, washed with water (3×30 ml) and brine (20 ml), dried (Na$_2$SO$_4$) and concentrated under reduced pressure. The residue was purified by flash chromatography on silica (chloroform/acetone 1:1) to give the title compound as a light yellow solid. Yield 86 mg (60%).

$^1$H-NMR (270 MHz, DMSO-$d_6$) δ 3.86 (3H, s, —OCH$_3$), 5.52 (2H, s), 7.20-7.25 (1H, m), 7.58-7.69 (3H, m), 7.74-7.76 (1H, m), 7.80-7.83 (1H, m), 7.93 (3H, br s), 8.40 (1H, s), 9.57 (1H, br s);

MS (FAB+): m/z 485.9 (100%, [M+H]$^+$);

HRMS (FAB+) calcd for C$_{17}$H$_{17}$FN$_5$O$_7$S: 486.05535; found, 486.05566.

HPLC (ACS80) $t_r$=1.740 min (95.1%).

Synthesis of STX1829

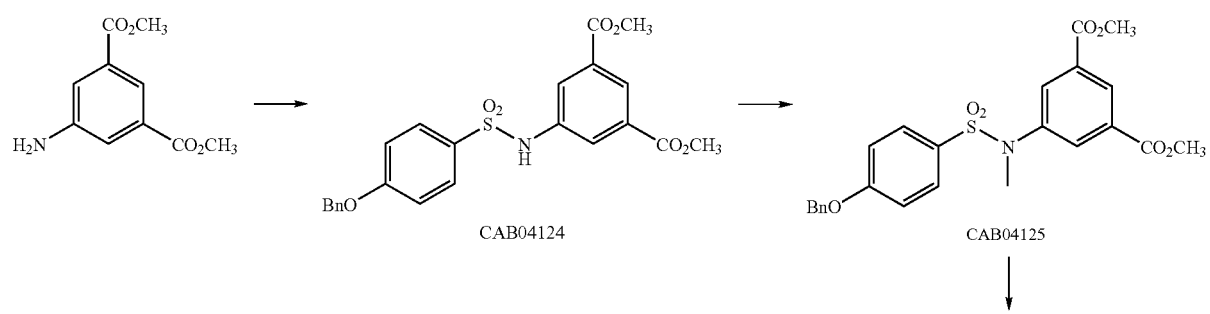

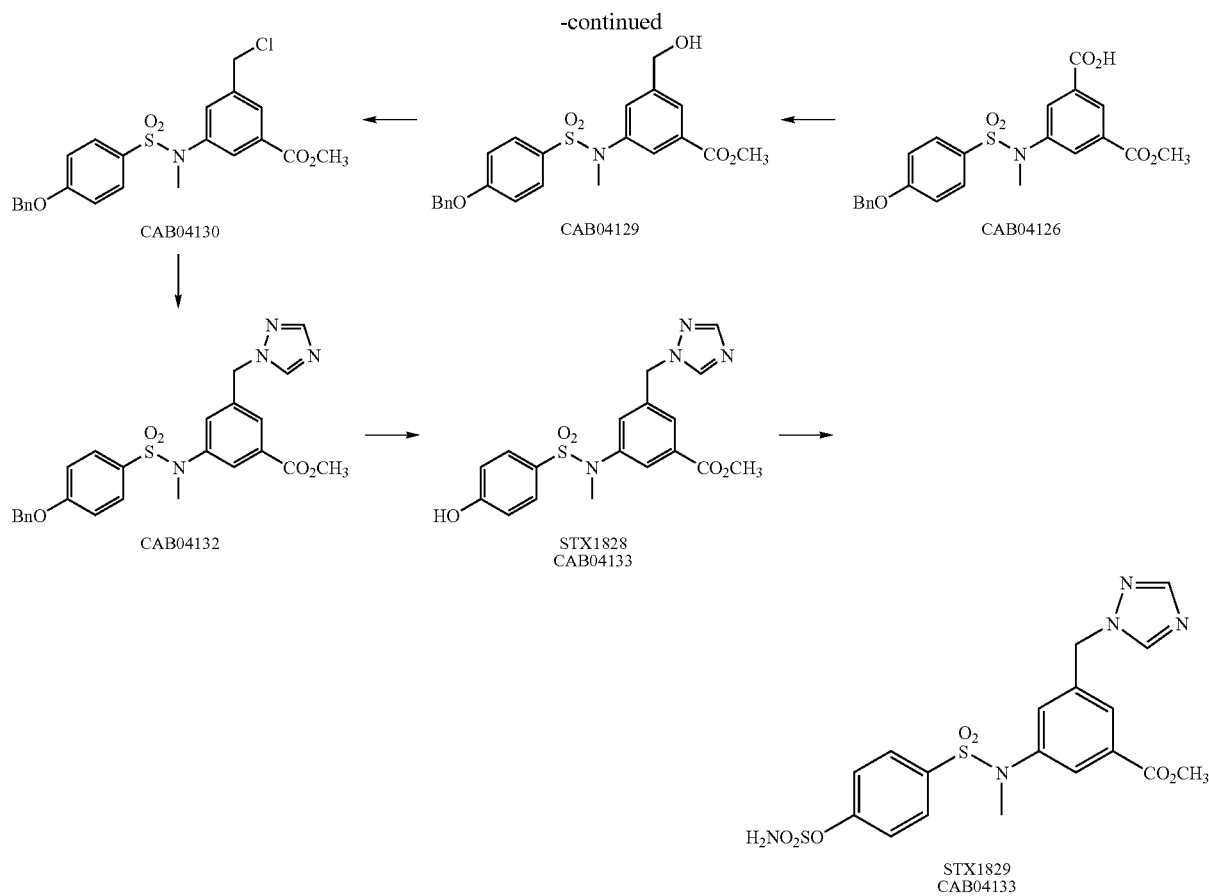

CAB04124

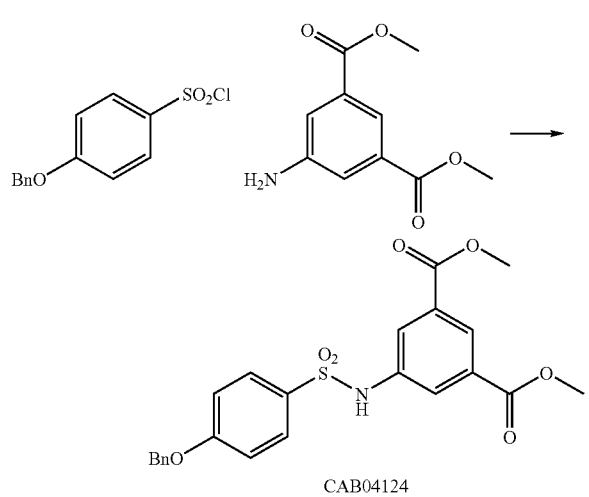

5-(4-Benzyloxy-benzenesulfonylamino)-isophthalic acid dimethyl ester (CAB04124): 4-Benzyloxy-benzenesulfonyl chloride (7.35 g, 26.0 mmol) was added in small portions to a suspension of 5-amino isophtalic acid dimethyl ester (5.23 g, 25.0 mmol) in DCM (100 ml) and pyridine (10 ml). The resulting clear yellow solution was stirred for 2 hours at room temperature, the volatile solvents were removed under reduced pressure, the solid residue was suspended in MeOH (125 ml) and the mixture was heated to reflux for 10 minutes. The off white solid was filtered off, washed with water and cold MeOH and dried under high vacuum. Yield 10.93 g (96%).

$^1$H-NMR (400 MHz, DMSO-$d_6$) δ 3.87 (6H, s, 2×—OCH$_3$), 5.13 (2H, s), 7.17 (2H, d, J=9.0 Hz), 10.77 (1H, br s);

$^{13}$C-NMR (100.5 MHz, DMSO-$d_6$) δ 53.1, 70.2, 115.8, 124.2, 125.0, 128.4, 128.6, 128.9, 129.3, 131.1, 131.6, 136.6, 139.6, 162.3, 165.3;

MS (FAB+): m/z 456.2 (30%, [$C_{23}H_{22}NO_7S$]$^+$), 71.0 (100%);

HRMS (FAB+) calcd for $C_{23}H_{21}NO_7$: 455.09940; found, 455.10091.

HPLC (ACS80) $t_r$=2.059 min (99.8%).

CAB04125

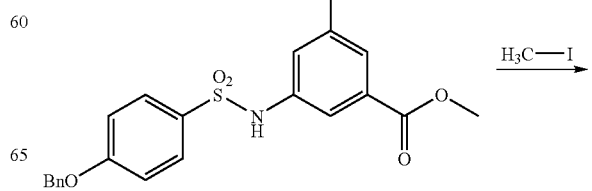

-continued

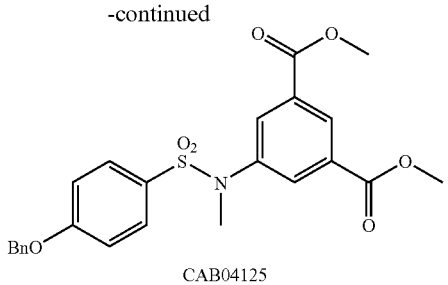
CAB04125

5-[(4-Benzyloxy-benzenesulfonyl)-methyl-amino]-isophthalic acid dimethyl ester (CAB04125): A mixture of CAB04124 (10.476 g, 23.0 mmol), $K_2CO_3$ (6.90 g, 50 mmol), methyl iodide (3.55 g, 25 mmol) and DMF (100 ml) was stirred vigorously for 16 hours. The reaction mixture was poured into crushed ice; the white precipitate was collected, washed with water and methanol and dried under high vacuum. Yield 10.58 g (98%).

$^1$H-NMR (400 MHz, DMSO-$d_6$) δ 3.20 (3H, s, NCH$_3$), 3.90 (6H, s, 2×OCH$_3$), 5.20 (2H, s), 7.19 (2H, d, J=9.0 Hz), 7.34-7.50 (7H, m), 7.92 (2H, d, J=1.6 Hz), 837 (1H, t, J=1.6 Hz);

$^{13}$C-NMR (100.5 MHz, DMSO-$d_6$) δ 37.8, 53.2, 70.3, 115.8, 127.5, 128.1, 128.4, 128.6, 129.0, 130.2, 130.8, 131.4, 136.6, 142.8, 162.7, 165.2;

MS (FAB+): m/z 470.2 (100%, [M+H]$^+$);

HRMS (FAB+) calcd for $C_{24}H_{23}NO_7S$: 469.11952; found, 469.11952.

HPLC (ACS80) $t_r$=2.350 min (99.9%).

CAB04126

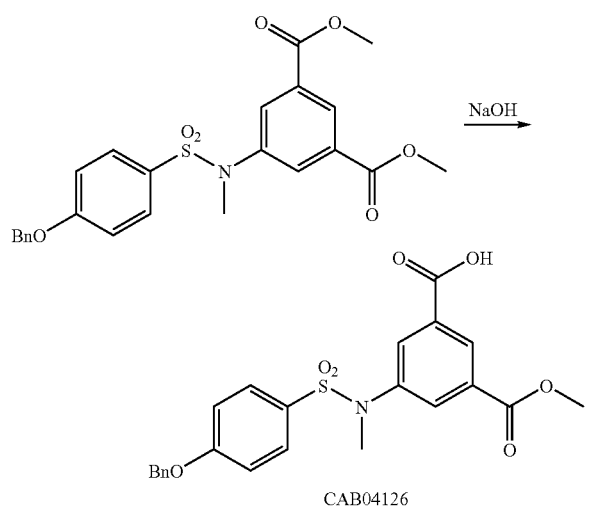
CAB04126

5-[(4-Benzyloxy-benzenesulfonyl)-methyl-amino]-isophthalic acid monomethyl ester (CAB04126): 2 M NaOH (10 ml) was added to a solution of CAB04125 (9.57 g, 20.0 mmol) in THF (75 ml) and MeOH (75 ml). The mixture was stirred for 48 hours at room temperature and poured into a mixture of water (500 ml) and conc. HCl (100 ml) with intensive stirring. After a short period of time a white, crystalline preciptate formed, which was filtered off, washed with water and dried under high vacuum. The solid was recrystallised from EtOAc/hexane. Yield: 8.29 g (91%).

$^1$H-NMR (400 MHz, DMSO-$d_6$) δ 3.19 (3H, s, NCH$_3$), 3.89 (3H, s, —OCH$_3$), 5.19 (2H, s), 7.20 (2H, d, J=8.9 Hz), 7.34-7.49 (7H, m), 7.86-7.88 (1H, m), 7.90-7.92 (1H, m), 8.37 (1H, m) (acid proton not resolved);

$^{13}$C-NMR (100.5 MHz, DMSO-$d_6$) δ 37.9, 53.1, 53.2, 70.3, 115.8, 127.5, 128.4, 128.6, 130.0, 130.2, 130.7, 130.9, 131.2, 132.7, 136.6, 142.6, 162.6, 165.3, 166.2;

MS (FAB+): m/z 456.1 (100%, [M+H]$^+$);

MS (APCI−): m/z 454.2 (100%, [M−H]$^−$);

HRMS (FAB+) calcd for $C_{23}H_{21}NO_7S$: 455.10387; found, 455.10266.

HPLC (ACS80) $t_r$=2.285 min (>99%).

CAB04129

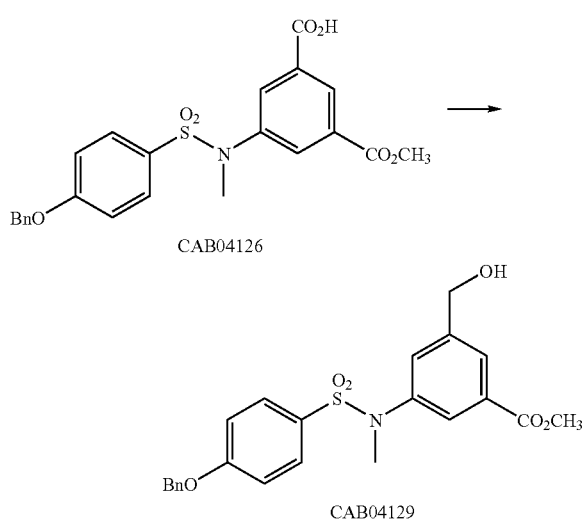
CAB04129

3-[(4-Benzyloxy-benzenesulfonyl)-methyl-amino]-5-hydroxymethyl-benzoic acid methyl ester (CAB04129): Borane in THF (10 ml, 1M solution) was added slowly to a solution of CAB04126 (2.28 g, 5.0 mmol) in THF (50 ml) at 0° C. The mixture was stirred overnight, AcOH (5 ml) was added carefully to destroy the excess borane. The solvent was removed under reduced pressure, the residue was dissolved in EtOAc (EtOAc (50 ml) and washed with water (30 ml) and conc. NaHCO$_3$-solution (2×30 ml), dried (Na$_2$SO$_4$), concentrated under reduced pressure and purified by flash chromatography on silica (EtOAc/hexane 1:1), R$_f$: 0.31) to give a white solid. Yield: 839 mg (38%).

$^1$H-NMR (270 MHz, CDCl$_3$) δ 1.90 (1H, t, J=5.9 Hz, —OH), 3.15 (3H, s, NCH$_3$), 3.88 (3H, s, OCH$_3$), 4.70 (2H, d, J=5.9 Hz), 5.09 (2H, s), 6.96 (2H, d, J=8.9 Hz), 7.30-7.50 (8H, m), 7.68 (1H, s), 7.92 (1H, s);

MS (FAB+): m/z 442.1 (100%, [M+H]$^+$);

CAB04130

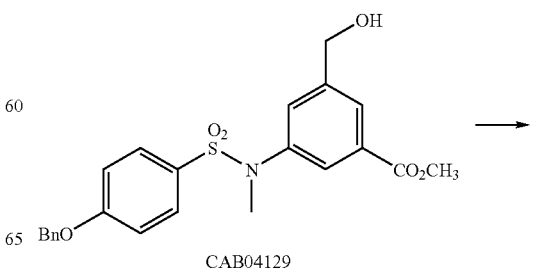
CAB04129

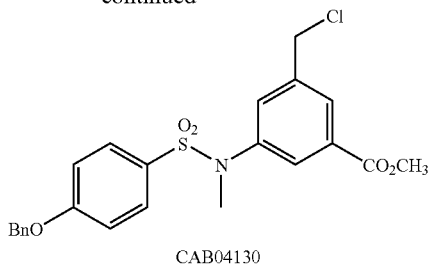
CAB04130

3-[(4-Benzyloxy-benzenesulfonyl)-methyl-amino]-5-chloromethyl-benzoic acid methyl ester (CAB04130): A mixture of CAB04129 (442 mg, 1.0 mmol) and thionyl chloride was heated to reflux for 2 hours. The excess thionyl chloride was removed under reduced pressure, the residue was purified by flash chromatography on silica (EtOAc/hexane 1:3, $R_f$: 0.35) to give the title compound as a colorless oil, which was crystallized from DCM/hexane. Yield: 308 mg (67%) fine colorless needles.

$^1$H-NMR (270 MHz, CDCl$_3$) δ 3.17 (3H, s, NCH$_3$), 3.89 (3H, s, OCH$_3$), 4.55 (2H, s, CH$_2$Cl), 5.12 (2H, s), 6.99 (2H, d, J=8.6 Hz), 7.30-8.00 (10H, m);

MS (APCI−): m/z 458.1 (100%, [M−H]$^-$);

CAB04132

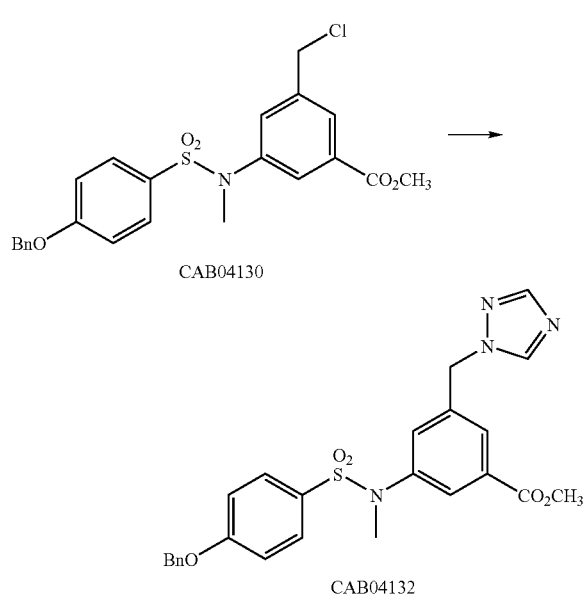

3-[(4-Benzyloxy-benzenesulfonyl)-methyl-amino]-5-[1,2,4]triazol-1-ylmethyl-benzoic acid methyl ester (CAB04132): A mixture of CAB04130 (230 mg, 0.5 mmol), 1,2,4-triazole (67 mg, 1.0 mmol), K$_2$CO$_3$ (690 mg, 5.0 mmol) and NaI (75 mg, 0.5 mmol) an acetone (20 ml) was stirred vigorously for 16 hours. The mixture was diluted with EtOAc (100 ml) and water (50 ml), the organic layer was separated, washed with brine (20 ml), dried (Na$_2$SO$_4$) and concentrated under reduced pressure. The residue was purified by flash chromatography (EtOAc, $R_f$: 0.39) to give the title compound as a colorless oil. Yield: 222 mg (90%).

$^1$H-NMR (400 MHz, CDCl$_3$) δ 3.15 (3H, s, —NCH$_3$), 3.88 (3H, s, —OCH$_3$), 5.12 (2H, s), 5.36 (2H, s), 6.98 (2H, d, J=9.0 Hz), 7.32-7.46 (9H, m), 7.68-7.71 (1H, m), 7.84 (1H, m), 7.84 (1H, s), 7.97 (1H, s), 8.15 (1H, s);

$^{13}$C-NMR (100.5 MHz, DMSO-d$_6$) δ 37.3, 52.1, 52.3, 70.0, 114.6, 126.3, 127.1, 127.2, 127.3, 128.0, 128.4, 129.5, 130.4, 1313, 135.4, 135.7, 142.4, 142.9, 152.0, 162.0, 165.2;

STX1828 (CAB04133)

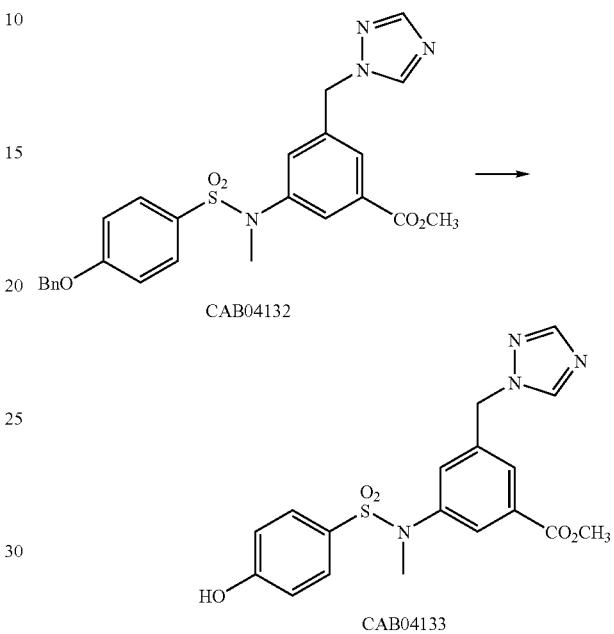

3-[(4-Hydroxy-benzenesulfonyl)-methyl-amino]-5-[1,2,4]triazol-1-ylmethyl-benzoic acid methyl ester (CAB04133, STX1828): Pd/C (50 mg, 5%) was added to a solution of CAB04132 (166 mg, 0.34 mmol) in MeOH (30 ml). The mixture was stirred under H$_2$-atmosphere at room temperature for 24 hours. The catalyst filtered off and the solution was concentrated under reduced pressure to give the title compound as white solid. Yield: 136 mg (100%).

$^1$H-NMR (300 MHz, DMSO-d$_6$) δ 3.07 (3H, s, —NCH$_3$), 3.83 (3H, s, —OCH$_3$), 5.47 (2H, s), 6.85 (2H, d, J=8.8 Hz), 7.28 (2H, d, J=8.8 Hz) 7.36-7.37 (1H, m), 7.57-7.58 (1H, m), 7.76 (1H, s), 8.00 (1H, s), 8.63 (1H, s), 10.58 (1H, br s, —OH);

MS (APCI−): m/z 401.2 (100%, [M−H]$^-$);

HPLC (ACS90) $t_r$=2.698 min (92.8%).

STX1829 (CAB04143)

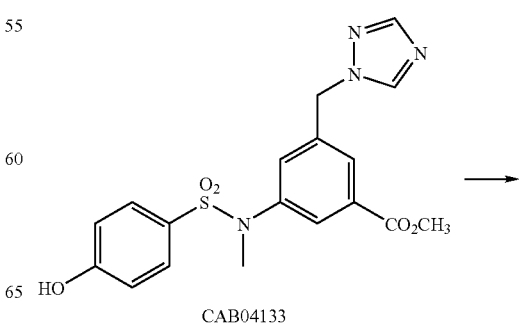
CAB04133

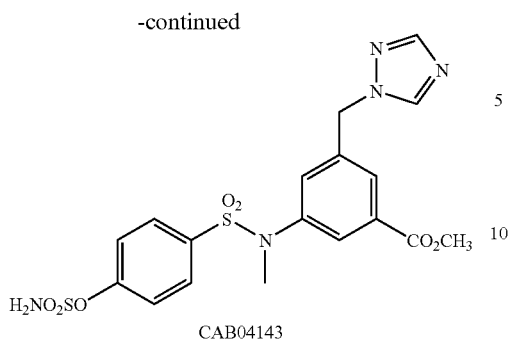

3-[Methyl-(4-sulfamoyloxy-benzenesulfonyl)-amino]-5-[1,2,4]triazol-1-ylmethyl-benzoic acid methyl ester (CAB04143, STX1829): Sulphamoyl chloride solution in toluene (3 ml, 0.7 M, 2.1 mmol) was concentrated under reduced pressure. The residue was dissolved In DMA (5 ml) at 0° C. and CAB04133 (95 mg, 0.236 mmol) was added to the solution. Stirring was continued for 18 hours, EtOAc (50 ml) and water 30 ml were added, the organic layer was separated, washed with water (3×30 ml) and brine (20 ml), dried (Na2SO$_4$) and concentrated under reduced pressure. The residue was purified by flash chromatography on silica (chloroform/acetone 1:1) to give the title compound as a light as colorless foam. Yield 91 mg (80%).

$^1$H-NMR (400 MHz, CDCl$_3$) δ 3.15 (3H, s, NCH$_3$), 3.90 (3H, s, OCH$_3$), 5.34 (2H, s, CH$_2$), 6.48 (1H, s), 7.20 (2H, brs, —NH$_2$), 7.32 (2H, d, J=8.9 Hz), 7.41 (2H, d, J=8.9 Hz), 7.84-7.87 (3H, m), 7.99 (1H, s);

$^{13}$C-NMR (100.5 MHz, CDCl$_3$) δ 38.3, 52.4, 52.7, 123.1, 127.8, 129.4, 129.5, 131.9, 134.2, 136.6, 142.6, 143.5, 151.3, 153.5, 165.6.

MS (APCI−): m/z 480.2 (100%, [M−H]$^-$);
HPLC (ACS0) t$_r$=1.828 min (>99%).

Synthesis of STX1830

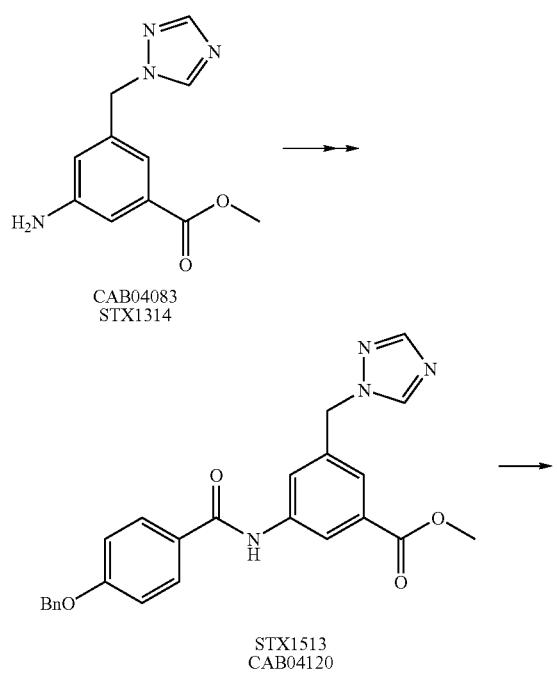

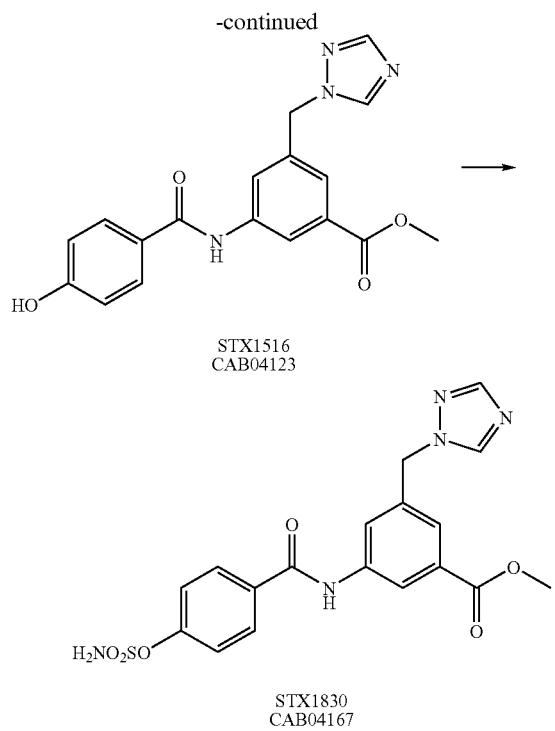

STX1513 (CAB04120)

3-(4-Benzyloxy-benzoylamino)-5-[1,2,4]triazol-1-ylmethyl-benzoic acid methyl ester (CAB04120, STX1513): 4-Benzyloxy-benzoyl chloride (247 mg, 1.0 mmol) was added to a solution of CAB04038 (232 mg, 1.0 mmol) in pyridine (5 ml). The mixture was stirred for 5 hours at room temperature, and then EtOAc (50 ml) and water (30 ml) were added. The organic layer was separated, washed with 2M KHSO$_4$ (2×30 ml) and brine (20 ml), dried over Na$_2$SO$_4$ and concentrated under reduced pressure. The residue was crystallized from EtOAc/hexane to give a white powder. Yield: 425 mg (96%).

$^1$H-NMR (400 MHz, DMSO-$d_6$) δ 3.88 (3H, s, —OCH$_3$), 5.23 (2H, s), 5.53 (2H, s), 7.17 (2H, d, J=8.6 Hz), 7.34-7.51 (5H, m), 7.62-7.64 (1H, m), 7.98 (2H, d, J=8.6 Hz), 8.00-8.02 (1H, m), 8.04 (1H, s), 8.41-8.42 (1H, m), 8.74 (1H, s), 10.37 (1H, s, NH);

$^{13}$C-NMR (100.5 MHz, DMSO-$d_6$) δ 52.2, 52.8, 69.9, 115.0, 120.7, 123.8, 124.2, 127.0, 128.3, 128.5, 130.0, 130.7, 137.1, 138.0, 140.6, 144.9, 152.5, 161.7, 165.5, 166.3;

MS (FAB+): m/z 443.1 (100%, [C$_{25}$H$_{23}$N$_4$O$_4$]$^+$);

HRMS (FAB+) calcd for C$_{17}$H$_{16}$ClN$_4$O$_5$S: 443.17193; found, 443.17252.

HPLC (ACS80) $t_r$=2.038 min (98.8%).

STX1516 (CAB04123)

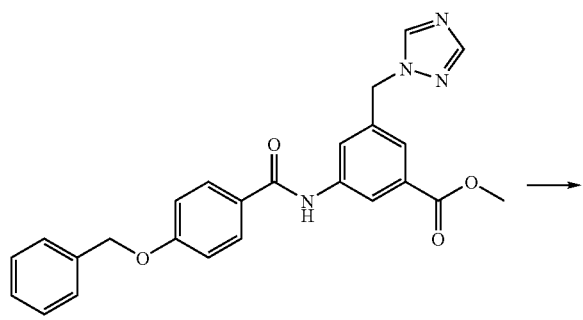

CAB04123

3-(4-Hydroxy-benzoylamino)-5-[1,2,4]triazol-1-ylmethyl-benzoic acid methyl ester (CAB04123, STX1516): Pd/C (50 mg, 5%) was added to a solution of CAB04120 (265 mg, 0.60 mmol) in MeOH (10 ml) and THF (10 ml). The mixture was stirred under H$_2$-atmosphere at room temperature for 18 hours. The catalyst filtered off and the solution was concentrated under reduced pressure to give the title compound as white solid. Yield: 207 mg (98%).

$^1$H-NMR (270 MHz, DMSO-$d_6$) δ 3.85 (3H, s, —OCH$_3$), 5.50 (2H, s), 6.86 (2H, d, J=8.4 Hz), 7.59 (1H, s), 7.86 (2H, d, J=8.4 Hz), 7.97 (1H, s), 8.02 (1H, s), 8.39 (1H, s), 8.71 (1H, s), 10.15 (1H, s), 10.24 (1H, s);

MS (FAB+): m/z 353.2 (100%, [C$_{18}$H$_{17}$N$_4$O$_4$]$^+$);

MS (AP−): m/z 351.2 (100%, [C$_{18}$H$_{15}$N$_4$O$_4$]$^−$);

HPLC (ACS80) $t_r$=1.851 min (>99%).

STX1830 (CAB04167)

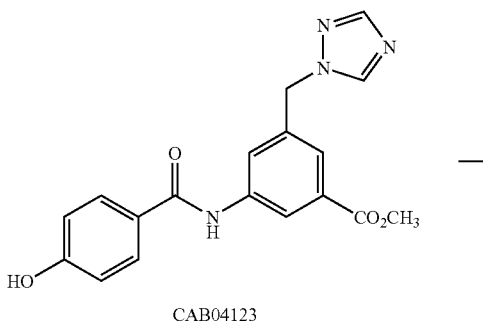

CAB04123

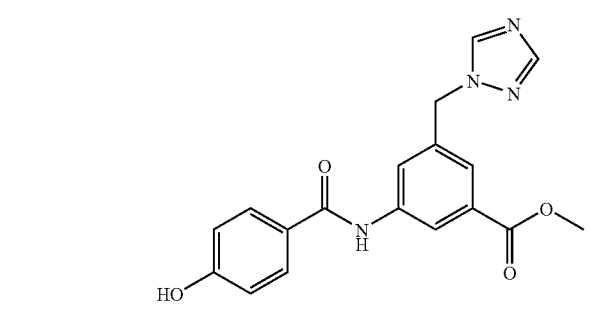

CAB04167

3-(4-Sulfamoyloxy-benzoylamino)-5-[1,2,4]triazol-1-yl-methyl-benzoic acid methyl ester (CAB04167, STX1830): Sulphamoyl chloride solution in toluene (3 ml, 0.7 M, 2.1 mmol) was concentrated under reduced pressure. The residue was dissolved In DMA (5 ml) at 0° C. and CAB04123 (80 mg, 0.227 mmol) was added to the solution. Stirring was continued for 18 hours, EtOAc (50 ml) and water 30 ml were added, the organic layer was separated, washed with water (3×30 ml) and brine (20 ml), dried (Na$_2$SO$_4$) and concentrated under reduced pressure. The residue was dissolved in a small amount of EtOAc and precipitated by addition of Et$_2$O and hexane to give the title compound as a white solid. Yield 81 mg (82%).

$^1$H-NMR (270 MHz, DMSO-$d_6$) δ 3.87 (3H, s, —OCH$_3$), 5.53 (2H, s), 7.42 (2H, d, J=8.6 Hz), 7.65 (1H, s), 7.99 (1H, s), 8.03 (1H, s), 8.06 (2H, d, J=8.6 Hz), 8.19 (2H, s, —NH$_2$), 8.42 (1H, s), 8.72 (1H, s), 10.57 (1H, s, —NH);

MS (APCI+): m/z 432.3 (100%, [M+H]$^+$);

HPLC (ACS90) $t_r$=1.739 min (99.7%).

Synthesis of STX1522

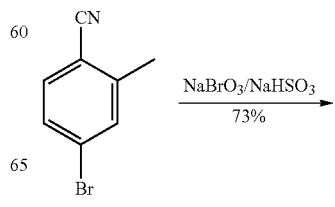

-continued

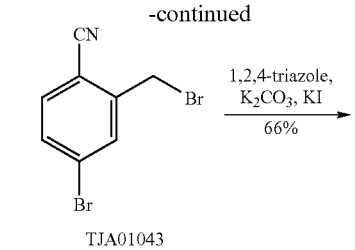
TJA01043

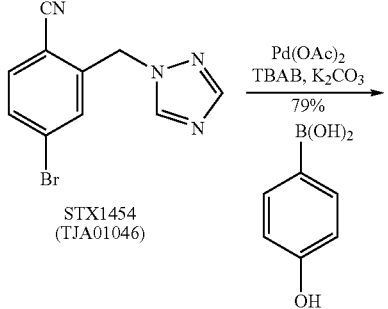
STX1454
(TJA01046)

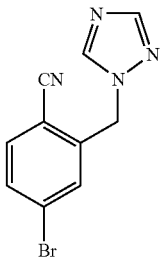

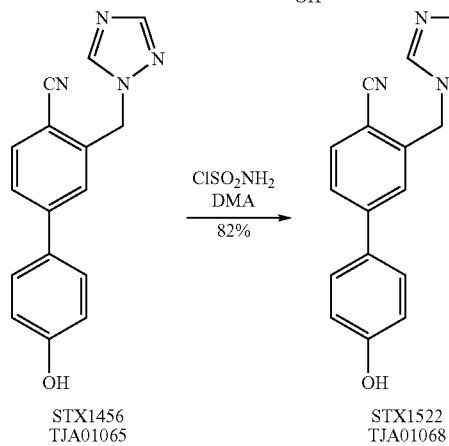
STX1456      STX1522
TJA01065     TJA01068

4-Bromo-2-bromomethylbenzonitrile (TJA01043)

C₈H₅Br₂N MW 274.94

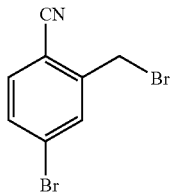

4-Bromo-2-methylbenzonitrile (5.00 g, 25.5 mmol), N-bromosuccinimide (4.99 g, 28.1 mmol), benzyl peroxide (0.198 g, 0.816 mmol) and carbon tetrachloride (100 mL) were loaded to a r.b. flask and set to reflux (79° C.) for 6 h. Once cooled the succinimide was filtered off and carbon tetrachloride removed via a dry ice-acetone cooled rotary evaporator. The residues were dissolved in dichloromethane (100 mL) and washed with distilled H₂O (50 mL×3) and brine (50 mL×2). Dried over Na₂SO₄ and solvent removed in vacuo to leave yellow residues. Column chromatography (hexane/dichloromethane 60:40) eluted the title compound as a yellow solid. Recrystallisation (cyclohexane) gave a white crystalline solid (5.07 g, 73%), mp 61.7-77.2° C. which was then used without further purification; R$_f$ 0.30 (hexane/dichloromethane 60:40), c.f. 0.36 (dibromobenzylbromide), 0.36 (4-bromo-2-methylbenzonitrile).

HPLC (60% CH₃CN in H₂O) R$_t$3.130 (50.62%), 2.701 (42.38%, dibromobenzylbromide); MS (EI), m/z 274.0 (M⁺, 34%).

4-Bromo-2-(1,2,4)triazol-1-ylmethyl-benzonitrile (TJA01046, STX1454)

C₁₀H₇BrN₄ MW 263.10

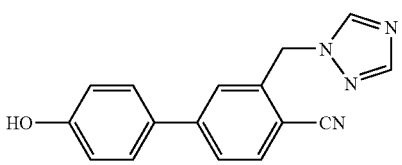

TJA01043 (5.00 g, 18.2 mmol), 1,2,4-triazole (1.89 g, 27.3 mmol), potassium carbonate (2.52 g, 18.2 mmol), potassium iodide (0.178 g, 1.07 mmol) and acetone (150 mL) were loaded to an r.b. flask. With vigorous stirring this mixture was set to reflux (60° C.) for 4 h. The reaction mixture was allowed to cool and acetone was removed in vacuo. The residues were taken up in ethyl acetate (50 mL) and washed with distilled water (50 mL×2), 1M NaOH (50 mL×1) and brine (50 mL×2). Dried over Na₂SO₄ and solvent removed in vacuo to leave orange/yellow residues. Flash chromatography (50 g column, Flashmaster II, method TJA01046) eluted dibromobenzylbromide and the title compound as a yellow solid. Recrystallisation (ethyl acetate/hexane 1:6) gave a yellow crystalline solid (1.58 g, 66%), mp 106.8-107.6° C.; R$_f$ 0.55 (ethyl acetate).

¹H NMR (270 MHz, CDCl₃) δ 5.51 (2H, s, ArCH₂N), 7.50 (1H, s, ArH), 7.53-7.56 (1H, d, J=8.8 Hz, ArH), 7.59-7.62 (1H, dd, J=1.7 & 8.5 Hz, ArH), 7.99 (1H, s, C₂H₂N₃) and 8.27 (1H, s, C₂H₂N₃);

¹³C NMR (100.5 MHz, CDCl₃) δ 50.7 (CH₂), 110.6, 116.3, 128.8, 132.8, 132.9, 134.2, 139.8, 143.9 and 153.0;

HPLC (80% CH₃CN in H₂O) t$_r$=1.947 min (100%);

MS (EI), m/z 264.71 (⁸¹BrM⁺, 100%), 262.71. (⁷⁹BrM⁺, 99), 195.56 ((⁸¹BrM⁺ −(C₂H₂N₃), 81), 193.56 ((⁷⁹BrM−(C₂H₂N₃)⁺, 80); Anal. Calc. for C₁₀H₇BrN₄: C 45.65, H 2.68, N 21.30. Found: C 45.60, H 2.70, N 20.9%.

4'-Hydroxy-3-[1,2,4]triazol-1-ylmethyl-biphenyl-4-carbonitrile (TJA01065, STX1520)

C₁₆H₁₂N₄O MW 276.30

A 10 mL microwave vial was loaded with TJA01046 (0.100 g, 0.380 mmol), 4-hydroxyphenylboronic acid (0.079 g, 0.570 mmol), potassium carbonate (0.131 g, 0.950 mmol), tetrabutylammonium bromide (0.126 g, 0.380 mmol), Pd(OAc)₂ (0.001-0.002 g, 2-3 mol %), ethanol (1.5 mL) and distilled water (3.5 mL). The vial was sealed and loaded (with no prior degassing) into a CEM Discover Microwave. After a run time of 3 min at 120° C. complete conversion was evident by tlc (ethyl acetate). The reaction mixture was allowed to cool and ethyl acetate (50 mL) added. This was then washed with distilled water (3×25 mL) and brine (2×25 mL). The organic layer was dried over $Na_2SO_4$, filtered and solvent removed in vacuo to leave a yellow/brown residue. The crude product was purified by flash chromatography (20 g column, Flashmaster II, method insol3) eluting the title compound as a white solid (0.082 g, 79%), mp 203.4-203.6° C. $R_f$: 0.43 (ethyl acetate).

$^1$H NMR (270 MHz, DMSO-$d_6$) δ 5.62 (2H, s, ArCH$_2$N), 6.85-6.88 (2H, d, J=8.7 Hz, ArH), 7.51-7.55 (2H, d, J=8.7 Hz, ArH), 7.67-7.89 (3H, m, ArH), 7.99 (1H, s, NCHN), 8.71 (1H, s, NCHN) and 9.83 (1H, s, ArOH);

$^{13}$C NMR (100.5 MHz, DMSO-$d_6$) δ 51.0, 109.2, 116.5, 117.8, 126.5, 127.5, 128.8, 134.3, 139.9, 145.4, 152.6 and 159.0;

HPLC (80% CH$_3$CN in H$_2$O) $t_r$=1.783 (97.91%);
LCMS (APCI), m/z 275.22 (M$^+$+H, 100%);

Sulfamic acid 4'-cyano-3'-[1,2,4]triazol-1-ylmethyl-biphenyl-4-yl ester (TJA01068, STX1522)

$C_{16}H_{13}N_5O_3S$ MW 355.37

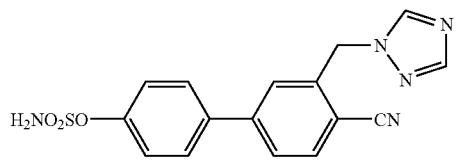

Sulfamoyl chloride in toluene (0.35 M, 5.17 mL) was transferred to an r.b. flask and the solvent removed under vacuum at 30° C. On cooling a white solid formed to which was added N,N-dimethylacetamide (1.5 mL) to form a colourless solution. TJA01065 (0.100 g, 0.361 mmol) was added and the solution left to stir at room temperature under $N_{2 (g)}$ for 18 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over Na$_2$SO$_4$ and solvent removed in vacuo to leave off white residues. Column chromatography (dichloromethane/acetone 80:20) eluted the title compound as a white solid (0.106 g, 82%);

mp 179.2-179.3° C.

$R_f$: 0.25 (dichloromethane/acetone 80:20).

$^1$H NMR (270 MHz, DMSO-$d_6$) δ 5.67 (2H, s, ArCH$_2$N), 7.38-7.41 (2H, d, J=8.7 Hz, ArH), 7.76-7.79 (2H, d, J=8.7 Hz, ArH), 7.82-7.86 (2H, s, ArH), 7.96-7.99 (1H, d, J=8.2 Hz, ArH), 8.01 (1H, s, C$_2$H$_2$N$_3$), 8.08 (2H, s, ArOSO$_2$NH$_2$) and 8.72 (1H, s, C$_2$H$_2$N$_3$);

$^{13}$C NMR (100.5 MHz, DMSO-$d_6$) δ 50.9 (CH$_2$), 110.7, 117.5, 123.4, 127.6, 128.5, 129.1, 134.5, 136.7, 140.2, 144.4, 145.4, 151.2 and 152.6; HPLC (80% CH$_3$CN in H$_2$O) $t_r$=1.725 (100%);

LCMS (APCI), m/z 356.27 (M$^+$+H, 100%), 277.24 ((M$^+$+H,)—OSO$_2$NH$_2$, 29).

Synthesis of STX1523

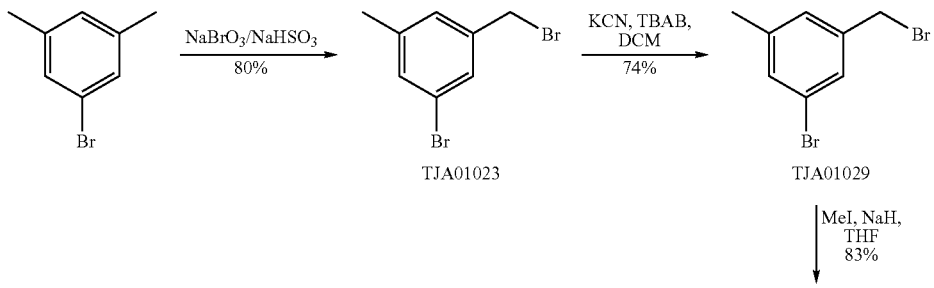

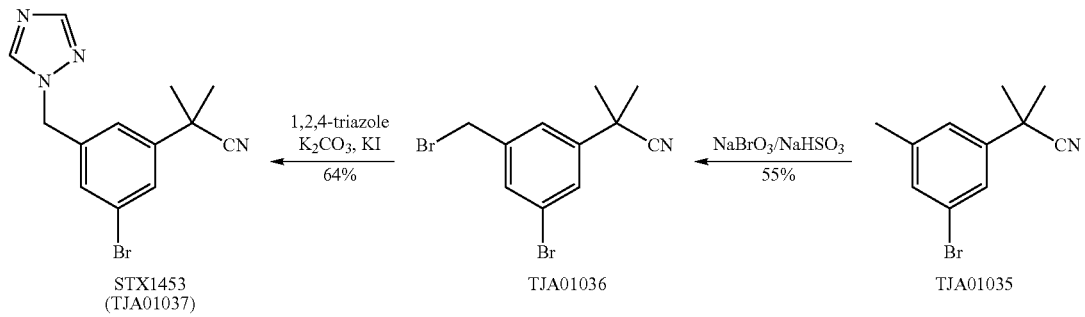

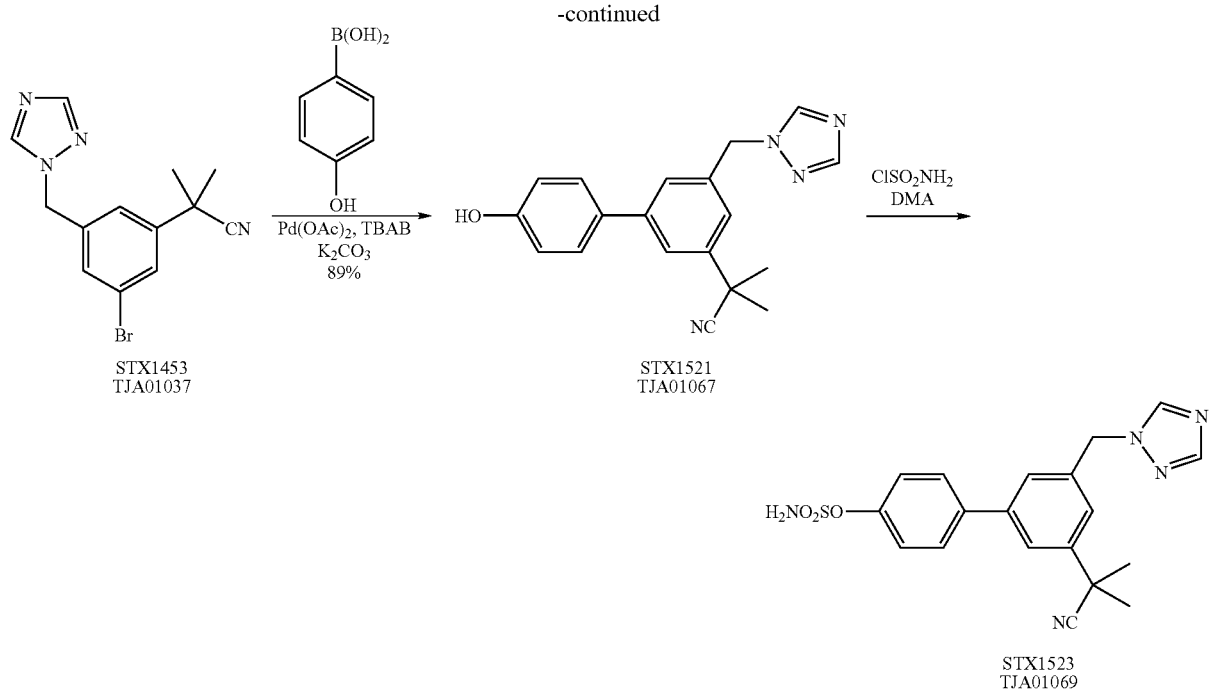

1-Bromo-3-bromomethyl-5-methylbenzene (TJA01023)

$C_8H_8Br_2$ MW 263.96

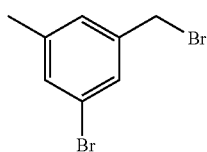

To a solution of sodium bromate (24.4 g, 162 mmol) in distilled $H_2O$ (40 mL) was added 5-bromo-m-xylene (10.0 g, 54.0 mmol) in cyclohexane (108 mL). To this clear mixture a solution of sodium hydrogen sulphate (30.8 g, 162 mmol) in distilled $H_2O$ (81 mL) was added drop wise with vigorous stirring over 60 min. The reaction mixture was stirred for a further 3 h at room temperature. The ethyl acetate was separated and diethyl ether (100 mL) added. This was then washed with saturated $Na2SO_{3(aq)}$ (1×100 mL), distilled water (2×100 ml) and brine (2×100 mL). Dried over $Na_2SO_4$ and solvent removed in vacuo to leave a clear syrup. Column chromatography (hexane) eluted the title compound as a clear oil that crystallised on standing to give a white crystalline solid that was used without further purification (8.45 g, 60%);

$R_f$ 0.52 (hexane), c.f 0.52 (dibromobenzylbromide), 0.45 (1,5-dibenzylbromide), 0.6 (5-bromo-m-xylene).

$^1H$ NMR (270 MHz, $CDCl_3$) δ 2.31 (3H, s, $ArCH_3$), 4.38 (2H, s, $ArCH_2Br$), 7.11 (1H, s, ArH), 7.25 (1H, s, ArH) and 7.32 (1H, s, ArH);

HPLC (60% $CH_3CN$ in $H_2O$) $t_r$=3.877 (67%), 4.644 (31%, dibromobenzylbromide).

(3-Bromo-5-methyl-phenyl)acetonitrile (TJA01029)

$C_9H8BrN$ MW 210.07

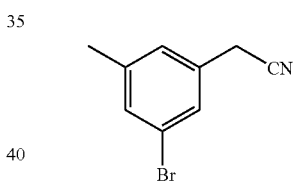

TJA01023 (11.3 g, 42.7 mmol), potassium cyanide (3.34 g, 51.2 mmol) and tetrabutylammonium bromide (0.700 g, 2.10 mmol) were loaded to an r.b. flask together with dichloromethane (60 mL) and distilled water (15 mL). With vigorous stirring the reaction mixture was set to reflux (45° C.) for 24 h. On cooling the organic fraction was separated and washed with distilled water (50 mL×2) and brine (50 mL×2) then dried over $Na_2SO_4$ and solvent removed in vacuo to leave a red/orange oil. Column chromatography initially eluting with hexane separated the dibromobenzylbromide impurity. Further elution with hexane/dichloromethane (50:50) gave the title compound as a clear yellow oil (6.63 g, 74%).

$R_f$: 0.54 (hexane/dichloromethane 50:50)

$^1H$ NMR (270 MHz, $CDCl_3$) δ 2.31 (3H, s, $ArCH_3$), 3.66 (2H, s, $ArCH_2CN$), 7.06 (1H, s, ArH), 7.25 (1H, s, ArH) and 7.27 (1H, s, ArH);

$^{13}C$ NMR (100.5 MHz, $CDCl_3$) δ 21.1, 23.2, 117.4, 122.8, 127.4, 128.1, 131.7, 131.9 and 141.1; HPLC (80% $CH_3CN$ in $H_2O$) $t_r$=2.278 (72.5%);

LCMS (APCI), m/z 211.78 ($^{81}BrM^+$, 53%), 209.78 ($^{79}BrM^+$, 55), 184.83 ($^{81}BrM^+$–CN, 80), 182.83 ($^{79}BrM^+$–CN, 76).

2-(3-Bromo-5-methylphenyl)-2-methyl-propionitrile (TJA01035)

$C_{11}H_{12}BrN$ MW 238.13

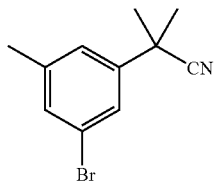

To a dry r.b. flask purged with $N_{2\,(g)}$ was added TJA01029 (6.00 g, 28.6 mmol) and dry THF (20 mL). With stirring this was cooled via an ice-water bath and NaH (1.71 g, 71.4 mmol) was added gradually and then left to stir at 0° C. under $N_{2\,(g)}$ for 15 min. Iodomethane (3.91 mL, 62.8 mmol) was then added dropwise. The resulting suspension was left to stir at room temperature for 16 h. Propan-2-ol (5 mL) was carefully added to the reaction mixture followed by dichloromethane (50 mL) and washed with distilled $H_2O$ (50 mL×2) and brine (50 mL×2). Dried over $Na_2SO_4$ and solvent removed in vacuo to leave a red/orange oil. Column chromatography (hexane/dichloromethane 50:50) eluted the title compound as a light yellow oil (5.65 g, 83%);

$R_f$: 0.38 (hexane/dichloromethane 50:50), c.f. 0.26 (3-Bromo-5-methyl-phenyl)acetonitrile;

$^1H$ NMR (270 MHz, $CDCl_3$) δ 1.68 (6H, s, $ArC(CH_3)_2$CN), 2.33 (3H, s, $ArCH_3$), 7.20 (1H, s, ArH), 7.26 (1H, s, ArH) and 7.34 (1H, s, ArH);

$^{13}C$ NMR (100.5 MHz, $CDCl_3$) δ 21.3 ($CH_3$), 29.0 ($CH_3$), 36.9 (C), 122.8, 124.1, 124.9, 125.2, 131.6, 140.9 and 143.4;

HPLC (80% $CH_3CN$ in $H_2O$) $t_r$=2.600 (89.65%);

LCMS (APCI), m/z 239.93 ($^{81}BrM^+$, 3%), 237.93 ($^{79}BrM^+$, 4), 212.92 ($^{81}BrM^+$–CN, 100), 210.92 ($^{79}BrM^+$–CN, 96), 157.89 ($M^+$–Br, 18).

2-(3-Bromo-5-bromomethyl-phenyl)-2-methylpropionitrile (TJA01036)

$C_{11}H_{11}Br_2N$ MW 317.03

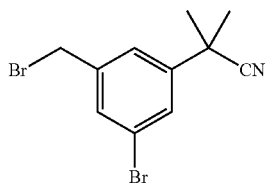

To a solution of sodium bromate (9.51 g, 63.0 mmol) in distilled $H_2O$ (32 mL) was added TJA01035 (5.00 g, 21.0 mmol) in cyclohexane (42 mL). To this clear mixture a solution of sodium hydrogen sulphate (7.56 g, 63.0 mmol) in distilled $H_2O$ (63 mL) was added drop wise with vigorous stirring over 1 h. The reaction mixture was stirred for a further 4 h at room temperature. The cyclohexane was separated and diethyl ether (100 mL) added. This was then washed with distilled water (50 ml×2) and brine (50 mL×2). Dried over $Na_2SO_4$ and solvent removed in vacuo to leave viscous orange oil. Column chromatography (hexane/dichloromethane 50:50) eluted starting material and the title compound as a clear viscous oil (3.64 g, 54%), $R_f$ 0.55 (hexane/dichloromethane 50:50), c.f. 0.38 (2-(3-bromo-5-methylphenyl)-2-methyl-propionitrile);

$^1H$ NMR (270 MHz, $CDCl_3$) δ 1.71 (6H, s, $ArC(CH_3)_2$CN), 4.41 (2H, s, $ArCH_2Br$), 7.40-7.41 (1H, t, J=1.7, ArH) and 7.48-7.51 (2H, m, ArH);

HPLC (80% $CH_3CN$ in $H_2O$) $t_r$=2.508 (83.05%);

LRMS (FAB$^+$), m/z 319.1 ($^{81}BrM^+$, 100%), 317.1 ($^{79}BrM^+$, 100).

2-(3-Bromo-5-[1,2,4-triazole-1-yl-methylphenyl)-2-methylpropionitrile (TJA01037, STX1453)

$C_{13}H_{13}BrN_4$ MW 305.18

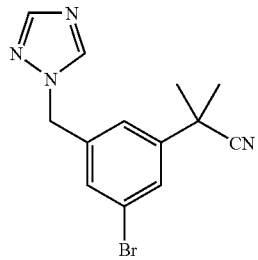

TJA01036 (3.20 g, 10.1 mmol), 1,2,4-triazole (1.05 g, 15.2 mmol), potassium carbonate (1.40 g, 10.1 mmol), potassium iodide (0.10 g, 0.600 mmol) and acetone (150 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2), 1M NaOH (50 mL×1) and brine (50 mL×2). Dried over $Na_2SO_4$ and solvent removed in vacuo to leave a yellow oil. Column chromatography (ethyl acetate) eluted the title compound as a clear viscous oil that crystallised on standing to give a colourless crystalline solid (1.97 g, 64%), mp 70.9-71.8° C.;

$R_f$ 0.24 (ethyl acetate).

$^1H$ NMR (270 MHz, $CDCl_3$) δ 1.68 (6H, s, $ArC(CH_3)_2$CN), 5.33 (2H, s, $ArCH_2N$), 7.40-7.41 (2H, t, J=1.7, ArH), 7.54-7.55 (1H, t, J=1.7, ArH), 7.99 (1H, s, $C_2H_2N_3$) and 8.12 (1H, s, $C_2H_2N_3$);

$^{13}C$ NMR (100.5 MHz, $CDCl_3$) δ 29.0 ($CH_3$), 37.0 (C), 52.6 ($CH_2$), 123.5, 123.7, 128.6, 130.4, 137.7, 143.4, 144.5 and 152.6 (one overlapping peak);

HPLC (60% $CH_3CN$ in $H_2O$ increasing to 95% over 10 min) $t_r$=2.293 (98.87%); MS (EI), m/z 307.09 ($^{81}BrM^+$, 100%), 305.09 ($^{79}BrM^+$, 99), 238.01 (($^{81}BrM-(C_2H_2N_3))^+$, 22), 236.01 (($^{79}BrM-(C_2H_2N_3))^+$, 24).

2-(4'-Hydroxy-5-[1,2,4]triazol-1-ylmethyl-biphenyl-3-yl)-2-methyl-propionitrile (TJA01067, STX1521)

$C_{19}H_{18}N_4O$ MW 318.37

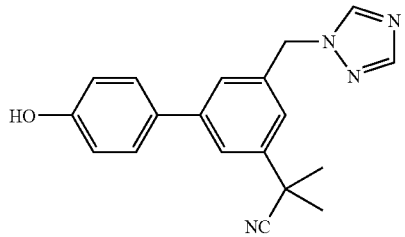

A 10 mL microwave vial was loaded with TJA01037 (0.200 g, 0.656 mmol), 4-hydroxyphenylboronic acid (0.136 g, 0.984 mmol), potassium carbonate (0.227 g, 1.64 mmol), tetrabutylammonium bromide (0.218 g, 0.656 mmol), $Pd(OAc)_2$ (0.004-0.005 g, 2-3 mol %), ethanol (1.5 mL) and distilled water (3.5 mL). The vial was sealed and loaded (with no prior degassing) into a CEM Discover Microwave. After a run time of 3 min at 120° C. complete conversion was evident by tlc (ethyl acetate). The reaction mixture was allowed to cool and ethyl acetate (50 mL) added. This was then washed with distilled water (25×3 mL) and brine (25 mL). The organic layer was dried over $Na_2SO_4$, filtered and solvent removed in vacuo to leave a yellow/brown residue. The crude product was purified by flash chromatography (20 g column, Flashmaster II, method insol3) eluting the title compound as a pale yellow (0.216 g, 89%), mp 65.8-68.1° C.

$R_f$: 0.28 (ethyl acetate).

$^1$H NMR (270 MHz, DMSO-$d_6$) δ 1.71 (6H, s, ArC(CH$_3$)$_2$CN), 5.49 (2H, s, ArCH$_2$N), 6.84-6.87 (2H, d, J=8.7 Hz, ArH), 7.38 (1H, s, ArH), 7.42 (1H, s, ArH), 7.44-7.48 (2H, d, J=8.7 Hz, ArH), 7.59 (1H, s, ArH), 8.00 (1H, s, C$_2$H$_2$N$_3$), 8.72 (1H, s, C$_2$H$_2$N$_3$) and 9.64 (1H, s, ArOH);

$^{13}$C NMR (100.5 MHz, DMSO-$d_6$) δ 28.8 (CH$_3$), 37.3 (C), 52.5 (CH$_2$), 116.3, 122.9, 123.3, 125.0, 125.5, 128.5, 130.5, 138.0, 141.8, 143.0, 144.9, 152.3 and 158.0;

HPLC (80% CH$_3$CN in H$_2$O) $t_r$=1.787 (99.55%);

LCMS (APCI), m/z 317.29 (M$^+$–H, 100%).

Sulfamic acid 3'-(cyano-dimethyl-methyl)-5'-[1,2,4]triazol-1-ylmethyl-biphenyl-4-yl ester (TJA01069, STX1523)

$C_{19}H_{19}N_5O_3S$ MW 397.45

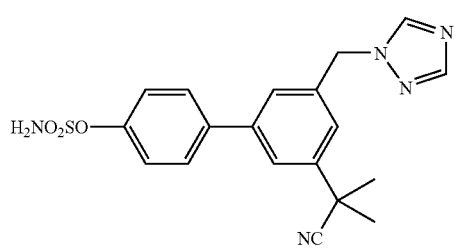

Sulfamoyl chloride in toluene (0.35 M, 4.49 mL) was transferred to an r.b. flask and the solvent removed under vacuum at 30° C. On cooling a white solid formed to which was added N,N-dimethylacetamide (4.0 mL) to form a colourless solution. TJA01067 (0.100 g, 0.314 mmol) was added and the solution left to stir at room temperature under N$_2$ $_{(g)}$ for 20 h. The reaction mixture was then poured into distilled H$_2$O (50 mL) and extracted with ethyl acetate (50 mL×2). The organic layers were combined and washed with distilled H$_2$O (50 mL×4) and brine (25 mL). Dried over Na$_2$SO$_4$ and solvent removed in vacuo to leave off white residues. Column chromatography (dichloromethane/acetone 80:20) eluted the title compound as a white waxy solid (0.111 g, 86%);

mp 74.3-76.1° C.

$R_f$: 0.21 (dichloromethane/acetone 75:25).

$^1$H NMR (270 MHz, DMSO-$d_6$) δ 1.72 (6H, s, ArC(CH$_3$)$_2$)CN), 5.52 (2H, s, ArCH$_2$N), 7.35-7.38 (2H, d, J=8.7 Hz, ArH), 7.49 (2H, s, ArH), 7.67 (1H, s, ArH), 7.69-7.72 (2H, d, J=8.7 Hz, ArH), 7.99 (1H, s, C$_2$H$_2$N$_3$), 8.04 (2H, s, ArOSO$_2$NH$_2$) and 8.71 (1H, s, C$_2$H$_2$N$_3$);

$^{13}$C NMR (100.5 MHz, DMSO-$d_6$) δ 28.7 (CH$_3$), 37.3 (C), 52.3 (CH$_2$), 123.3, 123.8, 124.6, 124.9, 126.3, 128.8, 138.3, 140.9, 143.3, 144.9, 150.5 and 152.4 (one overlapping signal);

HPLC (80% CH$_3$CN in H$_2$O) $t_r$=1.747 (98.58%);

LCMS (APCI), m/z 398.22 (M$^+$+H, 100%), 319.24 ((M$^+$+H,)—OSO$_2$NH$_2$, 15).

Synthesis of STX1729

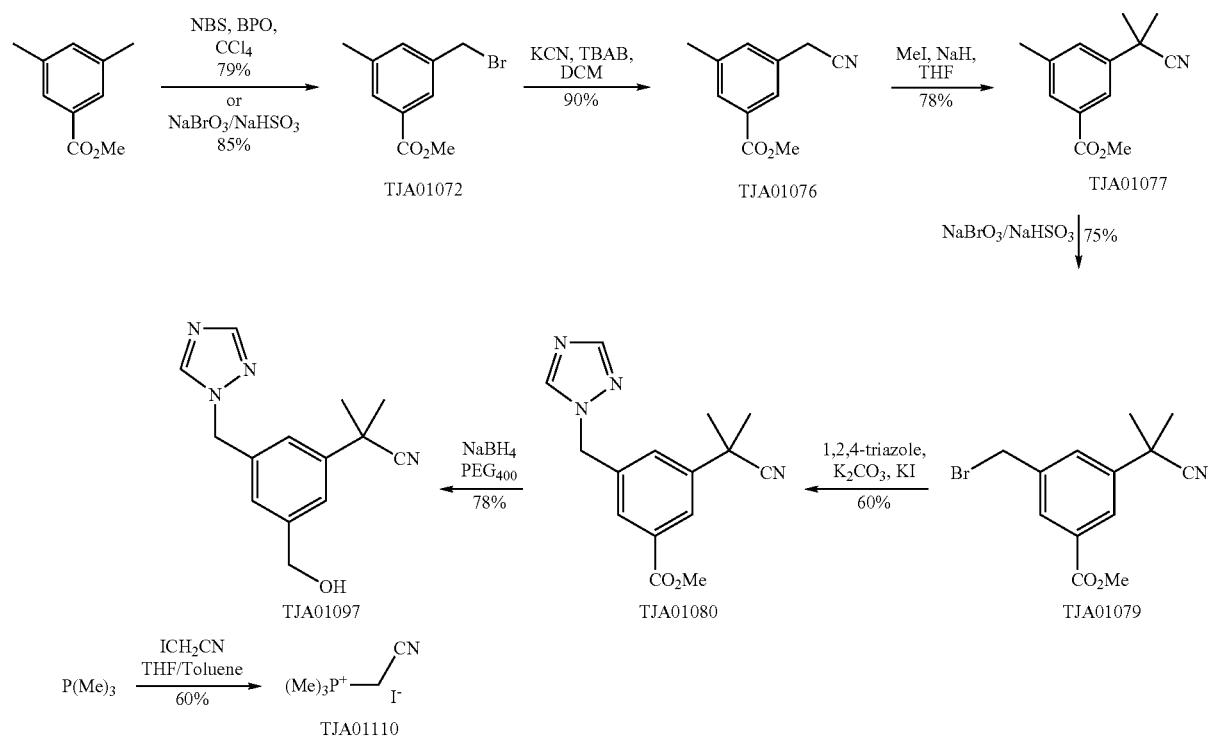

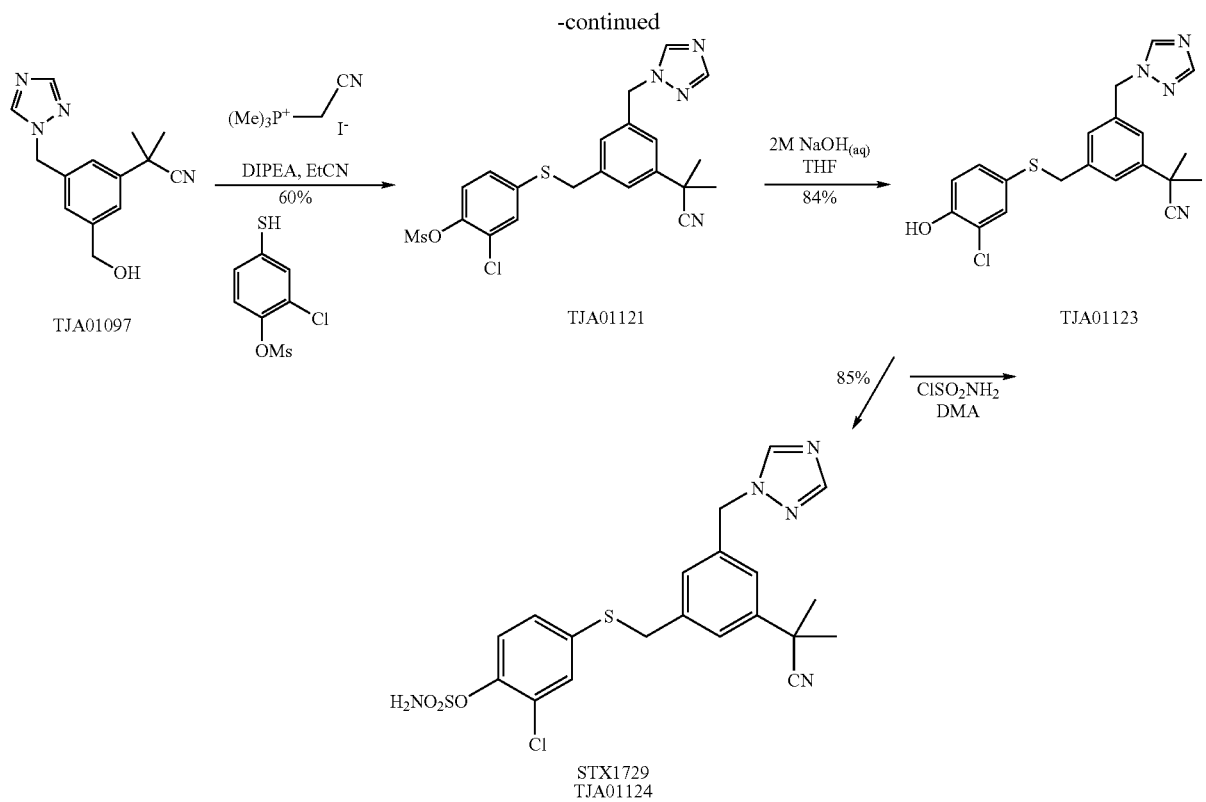

3-Bromomethyl-5-methyl-benzoic acid methyl ester (TJA01072)

$C_{10}H_{11}BrO_2$ MW 243.10

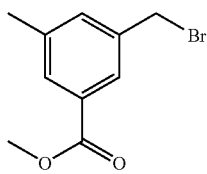

To a solution of sodium bromate (13.80 g, 91.5 mmol) in distilled $H_2O$ (45.8 mL) was added methyl 3,5-dimethylbenzoate (5.00 g, 30.5 mmol) in ethyl acetate (15.3 mL). To this mixture a solution of sodium hydrogen sulphate (10.99 g, 91.5 mmol) in distilled $H_2O$ (91.5 mL) was added drop wise with vigorous stirring over 1 h. The reaction mixture was stirred for a further 4 h at room temperature. The ethyl acetate was separated and diethyl ether (50 mL) added. This was then washed with saturated $Na_2SO_{3(aq)}$ (1×50 mL), distilled water (50 ml×2), and brine (50 mL×2). Dried over $Na_2SO_4$ and solvent removed in vacuo to leave a clear syrup. The syrup was dissolved with gentle heating in hexane (50 mL) and the resulting clear solution allowed to cool and then stand at 0° C. for 30 min. A white ppt (3,5-bis-bromomethyl-benzoic acid methyl ester) was removed via filtration. The filtrate was reduced to a clear syrup. Column chromatography (hexane/ethyl acetate 10:1) eluted the title compound as a clear oil (6.3 g, 85%—of which 14% is methyl 3,5-dimethylbenzoate); $R_f$ 0.45 (hexane), c.f 0.3 (3,5-bis-bromomethyl-benzoic acid methyl ester), 0.56 (methyl 3,5-dimethylbenzoate).

$^1$H NMR (270 MHz, CDCl$_3$) δ 2.37 (3H, s, ArCH$_3$, 3.89 (3H, s, ArCO$_2$CH$_3$), 4.47 (2H, s, ArCH$_2$Br), 7.38 (1H, s, ArH), 7.77 (1H, s, ArH) and 7.84 (1H, s, ArH);

$^{13}$C NMR (100.5 MHz, CDCl$_3$) δ 21.2 (CH$_3$), 32.7 (CH$_3$), 52.3 (CH$_2$), 127.3, 130.3, 130.7, 134.2, 138.1, 139.0 and 166.7 (C=O);

3-Cyanomethyl-5-methyl-benzoic acid methyl ester (TJA01076)

$C_{11}H_{11}NO_2$ MW 189.21

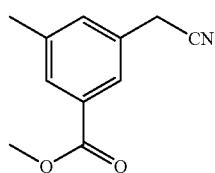

TJA01072 (19.5 g, 80.1 mmol), potassium cyanide (6.26 g, 96.1 mmol) and tetrabutylammonium bromide (1.33 g, 4.00 mmol) were loaded to an r.b. flask together with dichloromethane (100 mL) and distilled water (40 mL). With vigorous stirring the reaction mixture was set to reflux (45° C.) for 24 h. On cooling the organic fraction was separated and washed with distilled water (100 mL×2) and brine (100 mL) then dried over MgSO$_4$ and solvent removed in vacuo to leave a red/orange oil. Column chromatography initially eluting with hexane separated the dibromobenzylbromide impurity. Further elution with hexane/ethyl acetate (50:50) gave the title compound as a pale yellow solid (11.39 g, 75%), mp 56.2-57.8° C.;

R$_f$: 0.08 (ethyl acetate) c.f. 0.45 (TJA01072)

$^1$H NMR (270 MHz, CDCl$_3$) δ 2.34 (3H, s, ArCH$_3$), 3.79 (2H, s, ArCH$_2$CN), 3.89 (3H, s, ArCO$_2$CH$_3$), 7.34 (1H, s, ArH), 7.76 (1H, s, ArH) and 7.79 (1H, s, ArH);

$^{13}$C NMR (100.5 MHz, CDCl$_3$) δ 21.2 (CH$_3$), 23.4 (CH$_3$), 52.3 (CH$_2$), 117.6, 126.3, 130.0, 130.2, 131.0, 133.1, 139.5 and 166.7 (C=O);

HPLC (90% CH$_3$CN in H$_2$O) t$_r$=2.001 (100%);

LCMS (APCI), m/z 187.97 (M$^+$−H, 100%).

3-(Cyano-dimethyl-methyl)-5-methyl-benzoic acid methyl ester (TJA01077)

C$_{13}$H$_{15}$NO$_2$ MW 217.11

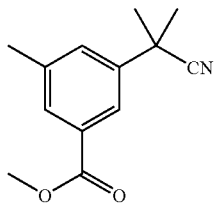

To a dry r.b. flask purged with N$_{2\,(g)}$ was added TJA01076 (7.00 g, 37.0 mmol) and dry THF (20 mL). With stirring this was cooled via an ice-water bath and NaH (2.22 g, 92.5 mmol) was added gradually and then left to stir at 0° C. under N$_{2\,(g)}$ for 15 min. Iodomethane (11.6 mL, 81.4 mmol) was then added dropwise. The resulting suspension was left to stir at room temperature for 16 h. Propan-2-ol (5 mL) was carefully added to the reaction mixture followed by dichloromethane (50 mL) and washed with distilled H$_2$O (50 mL×2) and brine (50 mL). Dried over MgSO$_4$ and solvent removed in vacuo to leave a red/orange oil. Column chromatography (hexane/ethyl acetate 90:10) eluted the title compound as a light yellow solid (6.29 g, 78%), mp 53.8-55.9° C.;

R$_f$: 0.26 (hexane/ethyl acetate 90:10);

$^1$H NMR (270 MHz, CDCl$_3$) δ 1.73 (6H, s, ArC(CH$_3$)$_2$CN), 2.41 (3H, s, ArCH$_3$), 3.91 (3H, s, ArCO$_2$CH$_3$), 7.51 (1H, s, ArH), 7.79 (1H, s, ArH) and 7.87 (1H, s, ArH);

$^{13}$C NMR (100.5 MHz, CDCl$_3$) δ 21.4, 29.1, 37.1, 52.3, 123.1, 124.3, 129.7, 130.7, 130.8, 139.2, 141.8 and 166.8 (C=O);

HPLC (90% CH$_3$CN in H$_2$O) t$_r$=4.293 (100%);

LCMS (APCI), m/z 217.99 (M$^+$+H, 83%), 191.99 ((M$^+$+H,)—CN, 100).

3-Bromomethyl-5-(cyano-dimethyl-methyl)-benzoic acid methyl ester (TJA01079)

C$_{13}$H$_{14}$BrNO$_2$ MW 296.17

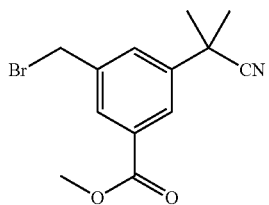

To a solution of sodium bromate (9.40 g, 62.2 mmol) in distilled H$_2$O (31 mL) was added TJA01077 (4.50 g, 20.8 mmol) in ethyl acetate (21 mL). To this clear mixture a solution of sodium hydrogen sulphate (7.47 g, 62.2 mmol) in distilled H$_2$O (124 mL) was added drop wise with vigorous stirring over 1 h. The reaction mixture was stirred for a further 4 h at room temperature. The ethyl acetate was separated and diethyl ether (100 mL) added. This was then washed with distilled water (50 ml×2) and brine (50 mL). Dried over MgSO$_4$ and solvent removed in vacuo to leave the title compound as a light yellow brown syrup (9.3 g, 75%—of which 33% starting material); R$_f$ 0.45 (hexane/ethyl acetate 85:15), c.f 0.52 (TJA01077), used without further purification.

HPLC (80% CH$_3$CN in H$_2$O) t$_r$=3.367 (85%);

LCMS (APCI), m/z 298.08 ($^{81}$BrM$^+$+H, 15%), 296.08 ($^{79}$BrM$^+$+), 15), 272.01 (($^{81}$BrM$^+$+H,)—CN, 100), 270.01 (($^{79}$BrM$^+$+H,)—CN, 100).

3-(Cyano-dimethyl-methyl)-5-[1,2,4]triazol-1-ylmethyl-benzoic acid methyl ester (TJA01080)

C$_{15}$H$_{16}$N$_4$O$_2$ MW 284.32

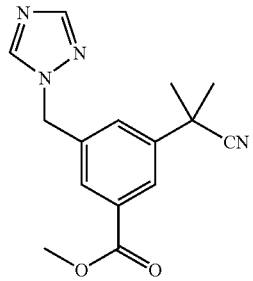

TJA01079 (9.30 g, 31.4 mmol), 1,2,4-triazole (3.25 g, 47.1 mmol), potassium carbonate (4.34 g, 31.4 mmol), potassium iodide (0.31 g, 1.85 mmol) and acetone (200 mL) were loaded to an r.b. flask. With vigorous stirring this mixture was set to reflux (60° C.) for 22 h. The reaction mixture was allowed to cool and acetone was removed in vacuo. The residues were taken up in ethyl acetate (50 mL) and washed with distilled water (50 mL×3) and brine (50 mL). Dried over MgSO$_4$ and solvent removed in vacuo to leave a dark brown syrup. Column chromatography (hexane/ethyl acetate 85:15 then ethyl acetate) eluted TJA01077 (1.25 g) and the title compound as a brown solid (3.70 g, 60%), mp 78.0-79.4° C.;

R$_f$ 0.18 (ethyl acetate).

$^1$H NMR (270 MHz, CDCl$_3$) δ 1.72 (6H, s, ArC(CH$_3$)$_2$CN), 3.90 (3H, s, ArCO$_2$CH$_3$), 5.40 (2H, s, ArCH$_2$Br), 7.60 (1H, s, ArH), 7.85 (1H, s, ArH), 7.98 (1H, s, C$_2$H$_2$N$_3$), 8.07 (1H, s, ArH) and 8.14 (1H, s, C$_2$H$_2$N$_3$);

$^{13}$C NMR (100.5 MHz, CDCl$_3$) δ 29.0, 37.2, 52.6, 52.9, 123.7, 126.4, 128.5, 129.3, 131.9, 136.2, 143.1, 153.0 and 165.9 (C=O) (one overlapping peak);

HPLC (80% CH$_3$CN in H$_2$O) t$_r$=1.901 (99.60%);

LCMS (APCI), m/z 285.11 (M$^+$+H, 100%), 215.98 ((M$^+$+H,)—C$_2$H$_2$N$_3$, 45).

2-(3-Hydroxymethyl-5-[1,2,4]triazol-1-ylmethyl-phenyl)-2-methyl-propionitrile (TJA01097)

$C_{14}H_{16}N_4O$ MW 256.13

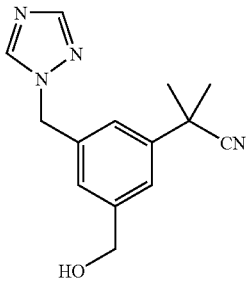

A 100 mL r.b. flask was loaded with TJA01080 (0.500 g, 1.76 mmol) and polyethylene glycol 400 (6.0 g). The mixture was heated to 80° C. with stirring until a solution had formed. Sodium borohydride (0.200 g, 5.28 mmol) was added carefully resulting in evolution of gas. The reaction mixture was stirred vigorously at 80° C. for 16 h. An extremely viscous glue formed that gradually dissolved in dichloromethane (50 mL) with heating (40° C.). This solution was washed with 1M $HCl_{(aq)}$ (10 mL) and then carefully neutralised with sodium bicarbonate. Washed with distilled water (50 mL×4) and brine (50 mL), separated and dried over $MgSO_4$. Solvent removed in vacuo to leave a viscous yellow oil. Flash chromatography (20 g column, Flashmaster II, method TJA01097) eluted the title compound as a white crystalline solid (0.351 g, 78%), mp 113.5-115.8° C.;

$R_f$: 0.12 (ethyl acetate), c.f. 0.24 (TJA01090b) and 0.24 (TJA01080);

$^1$H NMR (270 MHz, $CDCl_3$) δ 1.70 (6H, s, $ArC(CH_3)_2$ CN), 2.19-2.28 (1H, t, J=5.5 Hz, $ArCH_2OH$), 4.69-4.71 (2H, d, J=5.5 Hz, $ArCH_2OH$), 5.35 (2H, s, $ArCH_2N$), 7.17 (1H, s, ArH), 7.29 (1H, s, ArH), 7.44 (1H, s, ArH), 7.95 (1H, s, $C_2H_2N_3$) and 8.09 (1H, s, $C_2H_2N_3$);

$^{13}$C NMR (67.8 MHz, $CDCl_3$) δ 29.2 ($CH_3$), 37.2 (C), 53.4 ($CH_2$), 64.5 ($CH_2$), 123.9 (CH), 124.3 (C), 125.7 (CH), 135.9 (C), 142.7 (C), 143.1 (C), 143.2 (CH) and 152.4 (CH) (one overlapping peak);

HPLC (70% $CH_3CN$ in $H_2O$) $t_r$=2.253 (100%);

LCMS (APCI), m/z 257.23 ($M^+$+H, 100%), 188.12 (($M^+$+H,)—$C_2H_2N_3$, 88)

Cyanomethyl-trimethyl-phosphonium iodide (TJA01110)

$C_5H_{11}INP$ MW 243.03

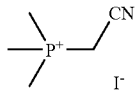

Trimethylphosphine in THF (1M, 20.0 mL, 20.0 mmol) at 0° C. under $N_{2(g)}$ was diluted with anhydrous toluene (40 mL). Iodoacetonitrile (1.40 mL, 19.4 mmol) was added dropwise with vigorous stirring forming a white ppt. The mixture was allowed to warm to r.t. and left to stir for 40 h. The mixture was filtered and washed with toluene to give a white solid which was dried under vacuum. Recrystallisation (acetonitrile) provided the title compound as a white crystalline solid (3.23 g, 66%), $^1$H NMR (300 MHz, DMSO-$d_6$) δ 2.01-2.06 (9H, d, J=15.3 Hz, $P(CH_3)_3$), 4.01-4.07 (2H, d, J=16.4 Hz, $PCH_2CN$);

$^{31}$P NMR (121.5 MHz, DMSO-$d_6$) δ 32.9.

Methanesulfonic acid 2-chloro-4-[3-(cyano-dimethyl-methyl)-5-[1,2,4]triazol-1-ylmethyl-benzylsulfanyl]-phenyl ester (TJA01121)

$C_{21}H_{21}ClN_4O_3S_2$ MW 477.00

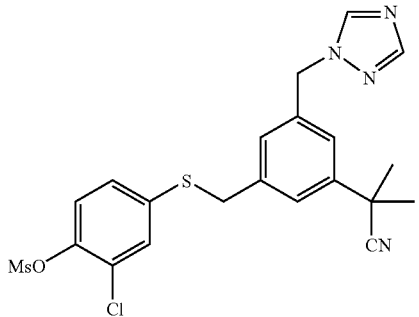

TJA01110 (0.114 g, 0.470 mmol) was added to a mixture of TJA01097 (0.100 g, 0.390 mmol), methanesulfonic acid-2-chloro-4-mercapto-phenyl ester (0.136 g, 0.570 mmol), diisopropylethylamine (88.0 μL, 0.510 mmol) and propionitrile (1.0 mL) in a dry 5 mL r.b. flask purged with $N_{2(g)}$. The mixture was then set to stir at 92° C. After 3 h a further 0.5 equivalents of TJA01110 (0.047 g, 0.195 mmol), diisopropylethylamine (33.9 μL, 0.195 mmol) and methanesulfonic acid-2-chloro-4-mercapto-phenyl ester (0.047 g, 0.195 mmol) was added. This was repeated after 5 h. After 17 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over $MgSO_4$ and solvent removed in vacuo to leave yellow residues. Flash chromatography (20 g column, Flashmaster II, method EtOAc) eluted the title compound as a yellow viscous oil (0.114 g, 61%), $R_f$: 0.27.

$^1$H NMR (300 MHz, $CDCl_3$) δ 1.60 (6H, s, $ArC(CH_3)_2$ CN), 3.19 (3H, s, $ArOSO_2CH_3$), 4.01 (2H, s, $ArCH_2S$), 5.26 (2H, s, $ArCH_2N$), 6.96 (1H, s, ArH), 7.07-7.12 (1H, dd, J=2.3 & 6.3 Hz, ArH), 7.19-7.26 (4H, m, ArH), 7.92 (1H, s, $C_2H_2N_3$) and 8.04(1H, s, $C_2H_2N_3$);

$^{13}$C NMR (100.5 MHz, $CDCl_3$) δ 29.1 ($CH_3$), 37.2 ($CH_2$), 38.9 ($CH_3$), 39.0 ($CH_2$), 53.1 ($CH_2$), 123.8 (CH), 124.0 (C), 124.9 (CH), 126.0 (CH), 127.7 (CH), 130.0 (CH), 132.1 (CH), 136.2 (C), 136.3 (C), 138.8 (C), 143.0 (C), 143.4 (CH) and 152.6 (CH) (two overlapping signals);

HPLC (90% $CH_3CN$ in $H_2O$) $t_r$=1.991 (100%);

LCMS (APCI), m/z 479.26 ($^{37}ClM^+$+H, 45%), 477.24 ($^{35}ClM^+$+H, 100).

2-[3-(3-Chloro-4-hydroxy-phenylsulfanylmethyl)-5-[1,2,4]triazol-1-ylmethyl-phenyl]-2-methyl-propionitrile (TJA01123)

$C_{20}H_{19}ClN_4OS$ MW 398.91

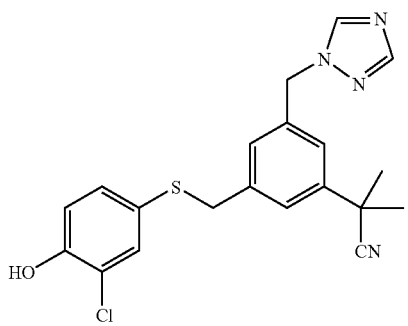

TJA01121 (0.100 g, 0.210 mmol) was dissolved in THF (2.5 mL) and methanol (1.5 mL) to which 2M $NaOH_{(aq)}$ (0.52 mL) was added. The mixture was set to stir at room temp. for 1 h. THF was removed under reduced pressure and the residues taken up in ethyl acetate (20 mL) and washed with 2M $KHSO_{4\ (aq)}$ (20 mL), distilled water (20 mL×2) and brine (20 mL). The organic layer was then dried over $MgSO_4$ and solvent removed under reduced pressure to leave a colourless viscous oil. Column chromatography (dichloromethane/acetone 80:20) eluted the title compound as a colourless viscous oil (0.071 g, 84%) that crystallised on standing to a white crystalline solid, mp 130.6-130.8° C.;

$R_f$: 0.31 (dichloromethane/acetone 80:20);

$^1$H NMR (400 MHz, DMSO-$d_6$) δ 1.59 (6H, s, ArC(CH$_3$)$_2$CN), 4.10 (2H, s, ArCH$_2$SAr), 5.43 (2H, s, ArCH$_2$N), 6.85-6.87 (1H, d, J=8.6 Hz, ArH), 7.07-7.10 (1H, dd, J=2.3 & 8.2 Hz, ArH), 7.14 (1H, s, ArH), 7.20 (1H, s, ArH), 7.26 (1H, s, ArH), 7.34 (1H, s, ArH), 8.00 (1H, s, C$_2$H$_2$N$_3$), 8.66 (1H, s, C$_2$H$_2$N$_3$) and 10.37 (1H, s, ArOH);

HPLC (90% CH$_3$CN in H$_2$O) $t_r$=2.199 (85.27%);

LCMS (APCI), m/z 401.38 ($^{37}$ClM$^+$+H, 30%), 399.43 ($^{35}$ClM$^+$+H, 100).

Sulfinamic acid 2-chloro-4-[3-(cyano-dimethyl-methyl)-5-[1,2,4]triazol-1-ylmethyl-benzylsulfanyl]-phenyl ester (TJA01124, STX1729)

$C_{20}H_{20}ClN_5O_3S_2$ MW 477.99

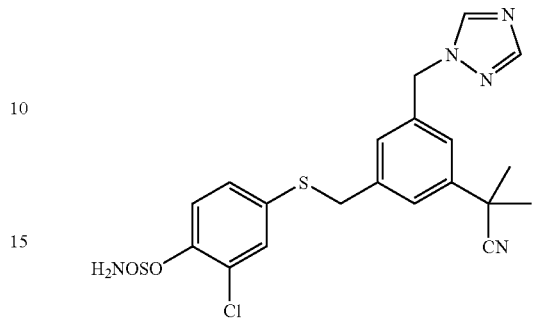

Sulfamoyl chloride in toluene (0.60 M, 1.05 mL) was transferred to an r.b. flask and the solvent removed under vacuum at 30° C. On cooling a white solid formed to which was added N,N-dimethylacetamide (1.5 mL) to form a colourless solution. TJA01123 (0.050 g, 0.125 mmol) was added and the solution left to stir at room temperature under $N_{2\ (g)}$ for 20 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over Na$_2$SO$_4$ and solvent removed in vacuo to leave off white residues. Column chromatography (dichloromethane/acetone 80:20) eluted the title compound as a colourless viscous oil (0.051 g, 85%), $R_f$: 0.55 (dichloromethane/acetone 80:20), c.f. 0.33 (TJA01123);

$^1$H NMR (270 MHz, DMSO-$d_6$) δ 1.62 (6H, s, ArC(CH$_3$)$_2$CN), 4.32 (2H, s, ArCH$_2$S), 5.44 (2H, s, ArCH$_2$N), 7.21 (1H, s, ArH), 7.34-7.39 (3H, m, ArH), 7.45 (1H, s, ArH), 7.53-7.54 (1H, d, J=1.5 Hz, ArH), 7.99 (1H, s, C$_2$H$_2$N$_3$), 8.27 (2H, s, ArOSO$_2$NH$_2$) and 8.66 (1H, s, C$_2$H$_2$N$_3$);

$^{13}$C NMR (100.5 MHz, DMSO-$d_6$) δ 28.3, 36.2, 36.5, 51.8, 123.7, 124.1, 124.3, 125.5, 127.0, 127.5, 128.3, 129.6, 135.5, 137.4, 138.5, 142.0, 144.2, 144.4 and 151.9;

HPLC (90% CH$_3$CN in H$_2$O) $t_r$=1.929 (99.51%);

LCMS (APCI), m/z 478.25 ($^{37}$ClM$^+$-H, 18%), 476.24 ($^{35}$ClM$^+$-H, 40), 399.35 (($^{37}$ClM$^+$-H)—C$_2$H$_2$N$_2$, 40), 397.35 (($^{35}$ClM$^+$-H)—C$_2$H$_2$N$_2$, 100).

Synthesis of STX1731

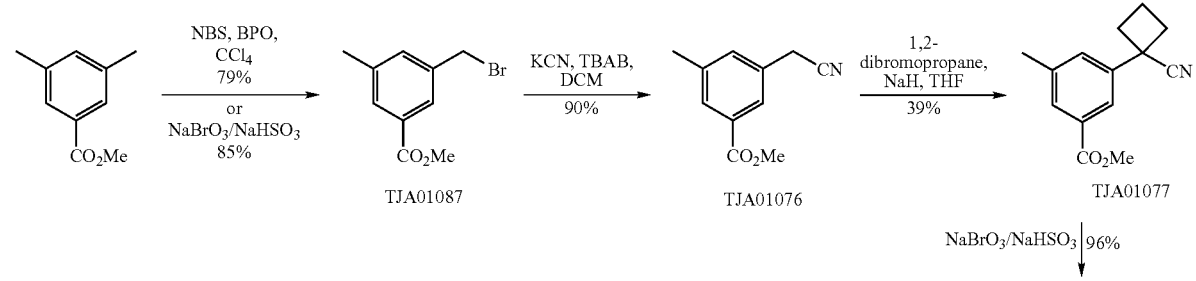

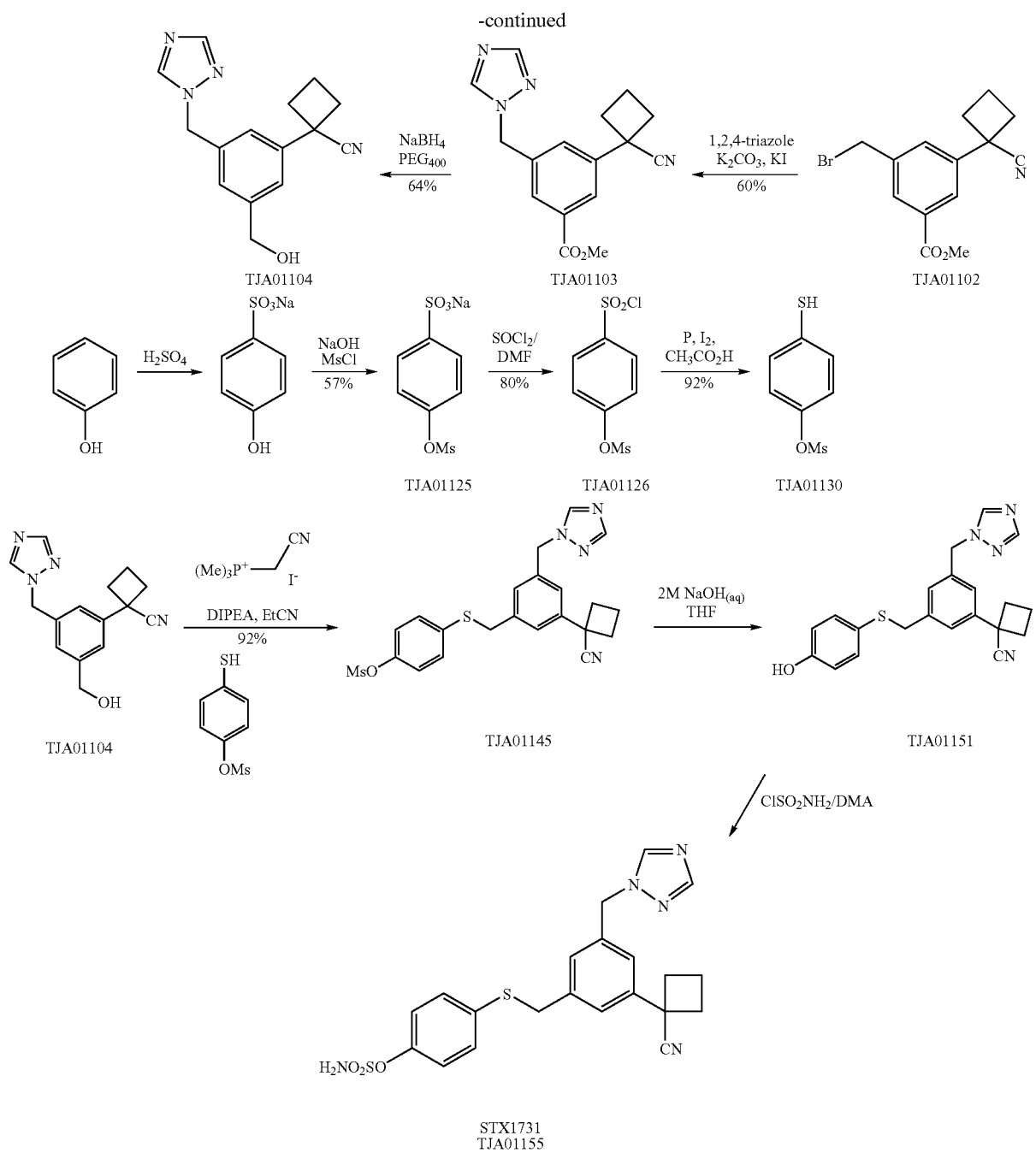

3-Bromomethyl-5-methyl-benzoic acid methyl ester (TJA01087)

$C_{10}H_{11}BrO_2$ MW 243.10

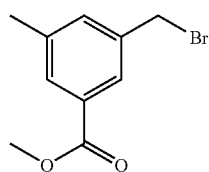

To a solution of sodium bromate (13.80 g, 91.5 mmol) in distilled $H_2O$ (45.8 mL) was added methyl 3,5-dimethylbenzoate (5.00 g, 30.5 mmol) in ethyl acetate (15.3 mL). To this mixture a solution of sodium hydrogen sulphate (10.99 g, 91.5 mmol) in distilled $H_2O$ (91.5 mL) was added drop wise with vigorous stirring over 1 h. The reaction mixture was stirred for a further 4 h at room temperature. The ethyl acetate was separated and diethyl ether (50 mL) added. This was then washed with saturated $Na_2SO_{3(aq)}$ (1×50 mL), distilled water (50 mL×2), and brine (50 mL×2). Dried over $Na_2SO_4$ and solvent removed in vacuo to leave a clear syrup. The syrup was dissolved with gentle heating in hexane (50 mL) and the resulting clear solution allowed to cool and then stand at 0° C. for 30 min. A white ppt (3,5-bis-bromomethyl-benzoic acid methyl ester) was removed via filtration. The filtrate was reduced to a clear syrup. Column chromatography (hexane/ethyl acetate 10:1) eluted the title compound as a clear oil (6.3 g, 85%—of which 14% is methyl 3,5-dimethylbenzoate); $R_f$ 0.45 (hexane), c.f 0.3 (3,5-bis-bromomethyl-benzoic acid methyl ester), 0.56 (methyl 3,5-dimethylbenzoate).

$^1$H NMR (270 MHz, CDCl$_3$) δ 2.37 (3H, s, ArCH$_3$, 3.89 (3H, s, ArCO$_2$CH$_3$), 4.47 (2H, s, ArCH$_2$Br), 7.38 (1H, s, ArH), 7.77 (1H, s, ArH) and 7.84 (1H, s, ArH);

$^{13}$C NMR (100.5 MHz, CDCl$_3$) δ 21.2 (CH$_3$), 32.7 (CH$_3$), 52.3 (CH$_2$), 127.3, 130.3, 130.7, 134.2, 138.1, 139.0 and 166.7 (C=O);

3-Cyanomethyl-5-methyl-benzoic acid methyl ester (TJA01076)

C$_{11}$H$_{11}$NO$_2$ MW 189.21

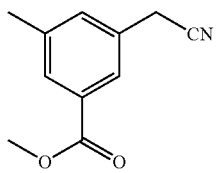

TJA01087 (19.5 g, 80.1 mmol), potassium cyanide (6.26 g, 96.1 mmol) and tetrabutylammonium bromide (1.33 g, 4.00 mmol) were loaded to an r.b. flask together with dichloromethane (100 mL) and distilled water (40 mL). With vigorous stirring the reaction mixture was set to reflux (45° C.) for 24 h. On cooling the organic fraction was separated and washed with distilled water (100 mL×2) and brine (100 mL) then dried over MgSO$_4$ and solvent removed in vacuo to leave a red/orange oil. Column chromatography initially eluting with hexane separated the dibromobenzylbromide impurity. Further elution with hexane/ethyl acetate (50:50) gave the title compound as a pale yellow solid (11.39 g, 75%), mp 56.2-57.8° C.;

$R_f$: 0.08 (ethyl acetate) c.f. 0.45 (TJA01072)

$^1$H NMR (270 MHz, CDCl$_3$) δ 2.34 (3H, s, ArCH$_3$), 3.79 (2H, s, ArCH$_2$CN), 3.89 (3H, s, ArCO$_2$CH$_3$), 7.34 (1H, s, ArH), 7.76 (1H, s, ArH) and 7.79 (1H, s, ArH);

$^{13}$C NMR (100.5 MHz, CDCl$_3$) δ 21.2 (CH$_3$), 23.4 (CH$_3$), 52.3 (CH$_2$), 117.6, 126.3, 130.0, 130.2, 131.0, 133.1, 139.5 and 166.7 (C=O);

HPLC (90% CH$_3$CN in H$_2$O) t$_r$=2.001 (100%);

LCMS (APCI), m/z 187.97 (M$^+$–H, 100%).

3-(1-Cyano-cyclobutyl)-5-methyl-benzoic acid methyl ester (TJA01098)

C$_{14}$H$_{15}$NO$_2$ MW 229.28

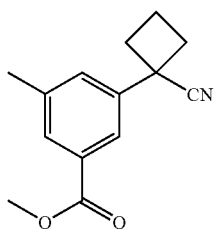

TJA01076 (1.50 g, 7.93 mmol) was loaded to a dry 25 mL r.b. flask which was subsequently purged with N$_{2\,(g)}$. To this was added dry DMF (10 mL) and the solution cooled with stirring to 0° C. Sodium hydride (0.476 g, 19.8 mmol) was carefully added resulting in a deep red coloration and evolution of gas. After 15 min at 0° C. 1,3-dibromopropane (0.960 mL, 9.48 mmol) was added dropwise over 5 min. The reaction was allowed to warm to room temp. and left to stir for 1 h. Ethyl acetate (50 mL) was added to the reaction mixture and this was washed with distilled water (50 mL×4) and brine (50 mL). The organic layer was separated and dried over MgSO$_4$, filtered and solvent removed in vacuo. Column chromatography (hexane/EtOAc 70:30) eluted the title compound as a colourless oil (0.783 g, 43%), $R_f$: 0.67 (hexane/EtOAc 70:30)

$^1$H NMR (270 MHz, CDCl$_3$) δ 2.00-2.23 (1H, m, CH$_2$), 2.35-2.52 (4H, m, ArCH$_3$ & CH$_2$), 2.55-2.69 (2H, m, CH$_2$), 2.77-2.89 (2H, m, CH$_2$), 3.91 (3H, s, ArCO$_2$CH$_3$), 7.39 (1H, s, ArH), 7.79 (1H, s, ArH) and 7.85 (1H, s, ArH);

$^{13}$C NMR (100.5 MHz, CDCl$_3$) δ 17.1, 21.3, 34.6, 40.0, 52.3, 126.8, 124.2, 129.8, 130.8, 131.1, 139.2, 140.2 and 166.7 (C=O);

HPLC (90% CH$_3$CN in H$_2$O) t$_r$=2.578 (99.99%);

LCMS (APCI), m/z 230.19 (M$^+$–H, 22%), 203.15 (M$^+$–CN, 100).

3-Bromomethyl-5-(1-cyano-cyclobutyl)-benzoic acid methyl ester (TJA01102)

C$_{14}$H$_{14}$BrNO$_2$ MW 308.17

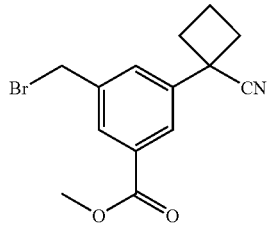

To a solution of sodium bromate (3.09 g, 20.5 mmol) in distilled H$_2$O (10 mL) was added TJA01098 (0.783 g, 3.42 mmol) in ethyl acetate (7 mL). To this clear mixture a solution of sodium hydrogen sulphate (2.46 g, 20.5 mmol) in distilled H$_2$O (20 mL) was added drop wise with vigorous stirring over 15 min. The reaction mixture was stirred for a further 4 h at room temperature. The ethyl acetate was separated and diethyl ether (100 mL) added. This was then washed with distilled water (25 ml×2) and brine (25 mL). Dried over MgSO$_4$ and solvent removed in vacuo. Column chromatography (hexane/ethyl acetate 75:25) eluted the title compound as a white crystalline solid (1.00 g, 96%), mp 93.9-94.6° C.;

$R_f$: 0.57 (hexane/ethyl acetate 75:25), c.f 0.74 (TJA01084);

$^1$H NMR (270 MHz, CDCl$_3$) δ 2.04-2.21 (1H, m, CH$_2$), 2.31-2.54 (1H, m, CH$_2$), 2.57-2.70 (2H, dd, J=2.0 & 9.7 Hz, CH$_2$), 2.81-2.90 (2H, m, CH$_2$), 3.93 (3H, s, ArCO$_2$CH$_3$), 4.50 (2H, s, ArCH$_2$Br), 7.61 (1H, s, ArH) and 8.00 (2H, s, ArH);

$^{13}$C NMR (100.5 MHz, CDCl$_3$) δ 17.1, 31.9, 34.7, 39.9, 52.5, 123.7, 126.7, 129.7, 130.7, 131.6, 139.2, 141.1 and 166.0 (C=O);

HPLC (80% CH$_3$CN in H$_2$O) t$_r$=3.486 (100%);

LRMS (EI$^+$), m/z 309.0 ($^{81}$BrM$^+$+H, 19%), 307.0 ($^{79}$BrM$^+$+H, 21%), 280.0 (($^{81}$BrM$^+$+H,)—CN, 53), 278.0 (($^{79}$BrM$^+$+H,)—CN, 54), 200.0 (((M$^+$+H,)—CN)—Br, 100).

3-(1-Cyano-cyclobutyl)-5-[1,2,4]triazol-1-ylmethyl-benzoic acid methyl ester (TJA01103)

$C_{16}H_{16}N_4O_2$ MW 296.13

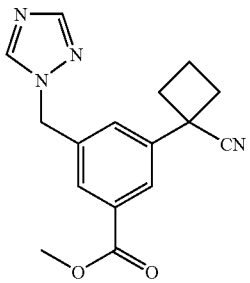

TJA01102 (1.00 g, 3.24 mmol), 1,2,4-triazole (0.336 g, 0.191 mmol), potassium carbonate (0.448 g, 3.24 mmol), potassium iodide (0.032 g, 0.191 mmol) and acetone (50 mL) were loaded to an r.b. flask. With vigorous stirring this mixture was set to reflux (60° C.) for 16 h. The reaction mixture was allowed to cool and acetone was removed in vacuo. The residues were taken up in ethyl acetate (50 mL) and washed with distilled water (50 mL×3) and brine (50 mL). Dried over MgSO₄ and solvent removed in vacuo to leave a dark brown syrup. Column chromatography (hexane/ethyl acetate 50:50 then ethyl acetate) eluted the title compound as a colourless viscous oil (0.410 g, 43%)

$R_f$: 0.26 (ethyl acetate);
¹H NMR (270 MHz, CDCl₃) δ 2.04-2.21 (1H, m, CH₂), 2.31-2.54 (1H, m, CH₂), 2.57-2.70 (2H, dd, J=2.0 & 9.7 Hz, CH₂), 2.81-2.90 (2H, m, CH₂), 3.93 (3H, s, ArCO₂CH₃), 4.50 (2H, s, ArCH₂Br), 7.61 (1H, s, ArH) and 8.00 (2H, s, ArH);
¹³C NMR (100.5 MHz, CDCl₃) δ 17.1, 31.9, 34.7, 39.9, 52.5, 123.7, 126.7, 129.7, 130.7, 131.6, 139.2, 141.1 and 166.0 (C=O);
HPLC (85% CH₃CN in H₂O) $t_r$=2.089 (99.47%);
LCMS (APCI), m/z 297.48 (M⁺+H, 100%), 214.33 ((M⁺+H)—CH₂C₂H₂N₃, 50).

1-(3-Hydroxymethyl-5-[1,2,4]triazol-1-ylmethyl-phenyl)-cyclobutanecarbonitrile (TJA01104)

$C_{15}H_{16}N_4O$ MW 268.31

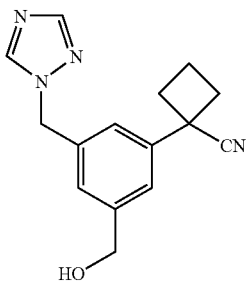

A 100 mL r.b. flask was loaded with TJA01103 (0.410 g, 1.38 mmol) and polyethylene glycol 400 (5.0 g). The mixture was heated to 80° C. with stirring until a solution had formed. Sodium borahydride (0.157 g, 4.15 mmol) was added carefully resulting in evolution of gas. The reaction mixture was stirred vigorously at 80° C. for 16 h. An extremely viscous glue formed that gradually dissolved in dichloromethane (50 mL) with heating (40° C.) This solution was washed with 1M HCl$_{(aq)}$ (10 mL) and then carefully neutralised with sodium bicarbonate. Washed with distilled water (50 mL×4) and brine (50 mL), separated and dried over MgSO₄. Solvent removed in vacuo to leave a colourless viscous oil. Flash chromatography (20 g column, Flashmaster II, method TJA01097) eluted the title compound as a colourless viscous oil (0.238 g, 64%), $R_f$: 0.14 (ethyl acetate), c.f. 0.28 (TJA01103);
¹H NMR (300 MHz, CDCl₃) δ 2.08-2.15 (1H, m, CH₂), 2.20-2.23 (1H, t, J=5.8 Hz, ArCH₂OH), 2.46-2.55 (1H, m, CH₂), 2.61-2.68 (2H, m, CH₂), 2.84-2.89 (2H, m, CH₂), 4.76-4.77 (2H, d, J=5.8 Hz, ArCH₂OH), 5.41 (2H, s, ArCH₂N), 7.25 (1H, s, ArH), 7.28 (1H, s, ArH), 7.45 (1H, s, ArH), 8.02 (1H, s, C₂H₂N₃), and 8.15 (1H, s, C₂H₂N₃);
¹³C NMR (69.5 MHz, CDCl₃) δ 17.2 (C), 34.6 (CH₂), 40.1 (CH₂), 53.3 (CH₂), 64.4 (CH₂), 124.3 (CH), 125.8 (CH), 135.9 (C), 141.1 (C), 143.3 (CH) and 152.3 (CH) (two overlapping signals);
HPLC (90% CH₃CN in H₂O) $t_r$=1.913 (100%);
LCMS (APCI), m/z 269.45 (M⁺+H, 100%).

4-Methanesulfonyloxy-benzenesulfonic acid sodium salt (TJA01125)

$C_7H_7NaO_6S_2$ MW 274.13

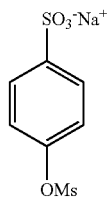

4-Hydroxybenzenesulfonic acid sodium salt dihydrate (11.6 g, 50.0 mmol) and sodium hydroxide (2.00 g, 50.0 mmol) were dissolved in distilled water (50 mL) and the solution cooled to 0° C. Methane sulfonyl chloride (4.25 mL, 55.0 mmol) was added dropwise with stirring and the mixture then allowed to warm to room temp. and left for 2 h. Brine (20 mL) was added and the solution left to stand for 1 h with the formation of white crystalline solid. The solids were filtered, recrystallised (brine), and dried under vacuum to give the title compound as a white crystalline solid (7.81 g, 57%), mp>250° C.;
¹H NMR (300 MHz, DMSO-d₆) δ 3.37 (3H, s, ArOSO₂CH₃) and 7.27-7.69 (4H, dd, J=8.7 & 17.5 Hz, AA'BB');
¹³C NMR (69.5 MHz, DMSO-d₆) δ 37.9 (CH₃), 122.2 (CH), 128.0 (CH), 147.7 (C) and 149.5 (C).

Methanesulfonic acid 4-chlorosulfonyl-phenyl ester (TJA01126)

$C_7H_7ClO_5S_2$ MW 270.71

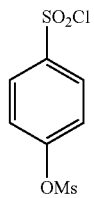

Thionyl chloride (30 mL) was cooled to 0° C. Cautiously, with stirring, TJA01125 (7.80 g, 28.0 mmol) was added followed by DMF (0.5 mL). The reaction mixture was subsequently heated to reflux (79° C.) for 1 h (or until evolution of gas has ceased) and then cooled. Thionyl chloride was removed in vacuo and the resulting yellow residues were taken up in dichloromethane (50 mL) and distilled water (50 mL) carefully added. The organic layer was separated and washed with distilled water (50 mL×2) and brine (50 mL), dried over MgSO$_4$ and solvent removed in vacuo to leave yellow residues. Recystallisation (dichloromethane/hexane) gave the title compound as a white crystalline solid (6.17 g, 80%), $^1$H NMR (300 MHz, CDCl$_3$) δ 3.21 (3H, s, ArOSO$_2$CH$_3$) and 7.47-8.08 (4H, dd, J=8.8 & 34.1 Hz, AA'BB');

$^{13}$C NMR (69.5 MHz, CDCl$_3$) δ 38.5 (CH$_3$), 123.3 (CH), 129.6 (CH), 142.6 (C) and 153.6 (C);

HPLC (90% CH$_3$CN in H$_2$O) t$_r$=2.489 (99.63%).

Methanesulfonic acid 4-mercapto-phenyl ester (TJA01130)

C$_7$H$_8$O$_3$S$_2$ MW 204.27

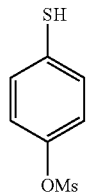

A 50 mL r.b. flask was loaded with red phosphorus powder (0.715 g, 23.1 mmol), iodine (0.039 g, 0.154 mmol) and acetic acid (7 mL). Cautiously TJA01126 (2.50 g, 9.23 mmol) was added and the reaction mixture then set to reflux (118° C.) for 2 h. Distilled water (1.5 mL) was added and the mixture left to reflux for a further 1 h. Reaction allowed to cool. Chloroform (30 mL) and distilled water (30 mL) were added. The organic layer was separated and washed with distilled water (30 mL×3) and brine (30 mL). Dried over MgSO$_4$, filtered and solvent removed in vacuo to provide the title compound as a white crystalline solid (1.74 g, 92%), R$_f$: 0.79 (ethyl acetate);

$^1$H NMR (270 MHz, CDCl$_3$) δ 3.10 (3H, s, ArOSO$_2$CH$_3$), 3.51 (1H, s, ArSH) and 7.13-7.30 (4H, dd, J=8.9 & 39.8 Hz, AA'BB');

$^{13}$C NMR (69.5 MHz, CDCl$_3$) δ 37.4 (CH$_3$), 122.9 (CH), 130.7 (C), 130.9 (CH), and 147.3 (C);

HPLC (70% CH$_3$CN in H$_2$O) t$_r$=2.152 (96.26%);

LCMS (APCI), nm/z 203.11 (M$^+$-H, 30%), 124.01 (M$^+$-SO$_2$CH$_3$, 100).

Methanesulfonic acid 4-[3-(1-cyano-cyclobutyl)-5-[1,2,4]triazol-1-ylmethyl-benzylsulfanyl]-phenyl ester (TJA01145)

C$_{22}$H$_{22}$N$_4$O$_3$S$_2$ MW 454.57

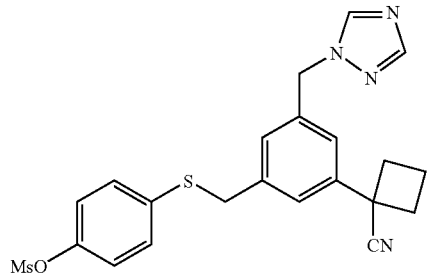

A dry 5 mL r.b. flask purged with N$_{2\ (g)}$ was loaded with TJA01110 (0.107 g, 0.447 mmol), TJA01104 (0.100 g, 0.373 mmol), TJA01130 (0.114, 0.539 mmol), diisopropylethylamine (84.5 μL, 0.485 mmol) and propionitrile (1.0 mL). The mixture was then set to stir at 93° C. After 2 h a further 1 equivalent of TJA01110 (0.091 g, 0.373 mmol) and diisopropylethylamine (65.0 μL, 0.373 mmol) were added. After 5 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over MgSO$_4$ and solvent removed in vacuo to leave yellow residues. Column chromatography (ethyl acetate) eluted the title compound as a yellow viscous oil (0.151 g, 92%), R$_f$: 0.35 (ethyl acetate);

$^1$H NMR (270 MHz, CDCl$_3$) δ 1.99-2.03 (1H, m, CH$_2$), 2.32-2.58 (3H, m, CH$_2$), 2.71-2.85 (2H, m, CH$_2$), 3.15 (3H, s, ArOSO$_2$CH$_3$), 4.06 (2H, s, ArCH$_2$S), 5.29 (2H, s, ArCH$_2$N), 6.97 (1H, s, ArH), 7.08-7.35 (6H, m, ArH), 7.97 (1H, s, C$_2$H$_2$N$_3$) and 8.08 (1H, s, C$_2$H$_2$N$_3$);

$^{13}$C NMR (69.5 MHz, CDCl$_3$) δ 17.1 (C), 34.5 (CH$_2$), 37.7 (CH$_3$), 39.2 (CH$_2$), 39.8 (CH$_2$), 53.1 (CH$_2$), 122.7 (CH), 124.0 (C), 124.2 (CH), 126.4 (CH), 127.7 (CH), 132.5 (CH), 134.6 (C), 136.1 (C), 139.3 (C), 141.2 (C), 143.4 (CH), 148.0 (C) and 152.4 (CH);

HPLC (90% CH$_3$CN in H$_2$O) t$_r$=1.859 (100%);

LCMS (APCI), m/z 455.40 (M$^+$+H, 100%).

1-(3-((1H-1,2,4-triazol-1-yl)methyl)-5-((4-hydroxyphenylthio)methyl)phenyl)cyclobutanecarbonitrile (TJA01151)

C$_{21}$H$_{20}$N$_4$OS MW 376.47

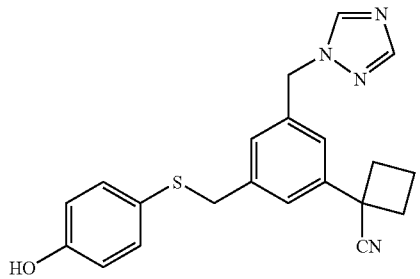

TJA01145 (0.133 g, 0.293 mmol) was dissolved in THF (4 mL) and methanol (2 mL) to which 2M NaOH$_{(aq)}$ (0.73 mL) was added. The mixture was set to stir at room temp. for 12 h. THF was removed under reduced pressure and the residues taken up in ethyl acetate (20 mL) and washed with 2M KHSO$_{4\ (aq)}$ (20 mL), distilled water (20 mL×2) and brine (20 mL). The organic layer was then dried over MgSO$_4$ and solvent removed under reduced pressure to leave a colourless viscous oil. Column chromatography (dichloromethane/acetone 80:20) eluted the title compound as a colourless viscous oil (0.091 g, 82%), R$_f$: 0.25 (dichloromethane/acetone 80:20);

$^1$H NMR (270 MHz, CDCl$_3$) δ 1.93-2.03 (1H, m, CH$_2$), 2.31-2.58 (3H, m, CH$_2$), 2.70-2.82 (2H, m, CH$_2$), 3.86 (2H, s, ArCH$_2$S), 5.23 (2H, s, ArCH$_2$N), 6.66-6.72 (3H, m, ArH), 7.01-7.08 (2H, dd, J=2.2 & 6.7 Hz, ArH), 7.15 (2H, s, ArH), 7.92 (1H, s, C$_2$H$_2$N$_3$), 7.99 (1H, s, C$_2$H$_2$N$_3$) and 8.18 (1H, bs, ArOH);

$^{13}$C NMR (69.5 MHz, CDCl$_3$) δ 17.2 (C), 34.5 (CH$_2$), 39.9 (CH$_2$), 41.1 (CH$_2$), 53.4 (CH$_2$), 116.3 (CH), 123.5 (C), 123.9 (CH), 126.8 (CH), 128.2 (CH), 134.9 (C), 135.7 (CH), 140.7

(C), 141.0 (C), 143.0 (CH), 151.7 (CH) and 156.8 (C); HPLC (90% CH$_3$CN in H$_2$O) t$_r$=1.876 (94.36%);
LCMS (APCI), m/z 377.33 (M$^+$+H, 100%).

4-((3-((1H-1,2,4-triazol-1-yl)methyl)-5-(1-cyanocyclobutyl)benzyl)sulfanyl)phenyl sulfamate (TJA01155, STX1731)

C$_{21}$H$_{21}$N$_5$O$_3$S$_2$ MW 455.55

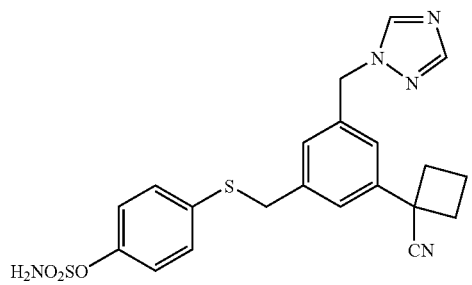

Sulfamoyl chloride in toluene (0.60 M, 2.86 mL) was transferred to an r.b. flask and the solvent removed under vacuum at 30° C. On cooling a white solid formed to which was added N,N-dimethylacetamide (1.5 mL) to form a colourless solution. TJA01151 (0.089 g, 0.236 mmol) was added and the solution left to stir at room temperature under N$_{2\,(g)}$ for 72 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over Na$_2$SO$_4$ and solvent removed in vacuo to leave off white residues. Column chromatography (dichloromethane/acetone 80:20) eluted the title compound as a colourless viscous oil (0.058 g, 55%), R$_f$: 0.40 (dichloromethane/acetone 80:20);
$^1$H NMR (270 MHz, CDCl$_3$) δ 2.03-2.10 (1H, m, CH$_2$), 2.42-2.61 (3H, m, CH$_2$), 2.77-2.82 (2H, m, CH$_2$), 4.03 (2H, s, ArCH$_2$SAr), 5.27 (2H, s, ArCH$_2$N), 6.59 (1H, s, ArH), 6.88 (2H, s, ArOSO$_2$NH$_2$), 7.11-7.33 (6H, m, ArH), 7.59 (1H, s, C$_2$H$_2$N$_3$) and 7.92 (1H, s, C$_2$H$_2$N$_3$);
$^{13}$C NMR (69.5 MHz, CDCl$_3$) δ 17.2 (C), 34.6 (CH$_2$), 38.2 (CH$_2$), 40.0 (CH$_2$), 53.2 (CH$_2$), 123.4 (CH), 124.0 (CH), 126.5 (CH), 126.8 (CH), 132.5 (CH), 132.7 (C), 135.6 (C), 140.1 (C), 141.2 (C), 143.9 (CH), 149.3 (C) and 151.2 (CH) (one overlapping signal);
HPLC (90% CH$_3$CN in H$_2$O) t$_r$=1.827 (100%);
LCMS (APCI), m/z 456.34 (M$^+$+H, 100%), 377.39 (M$^+$−SO$_2$NH$_2$, 20%).

Synthesis of STX1732

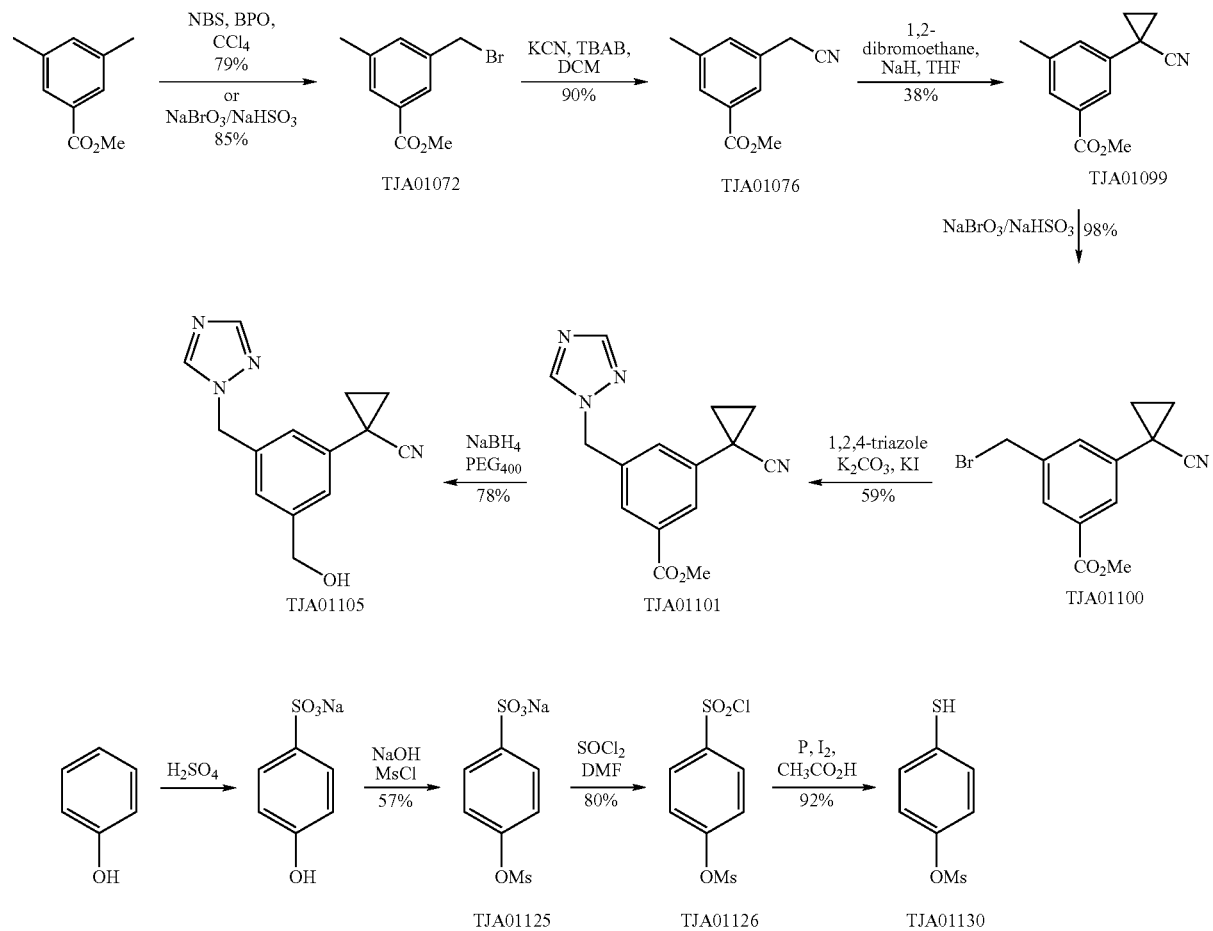

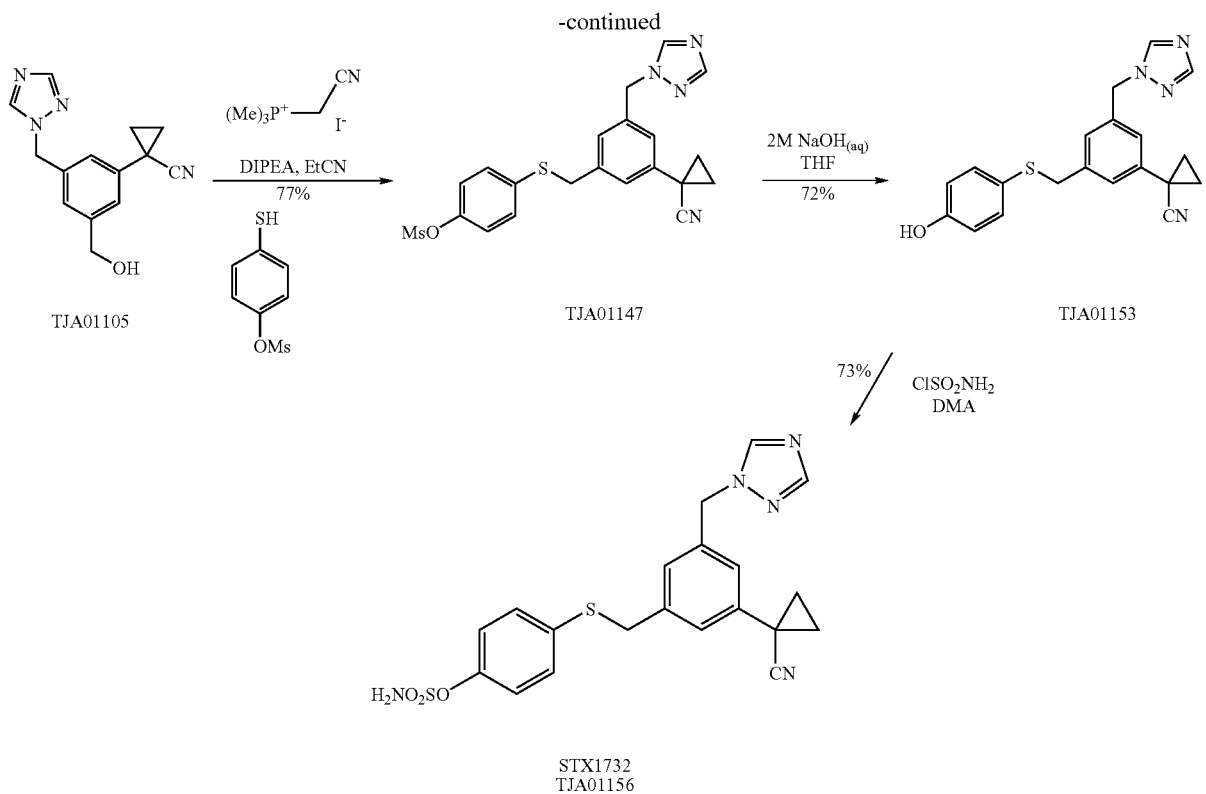

3-(1-Cyano-cyclopropyl)-5-methyl-benzoic acid methyl ester (TJA01099)

$C_{13}H_{13}NO_2$ MW 215.09

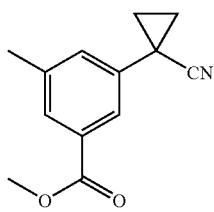

TJA01076 (1.50 g, 7.93 mmol) was loaded to a dry 50 mL r.b. flask which was subsequently purged with $N_{2\ (g)}$. To this was added dry DMF (10 mL) and the solution cooled with stirring to 0° C. Sodium hydride (0.476 g, 19.8 mmol) was carefully added resulting in a deep red coloration and evolution of gas. After 15 min at 0° C. 1,2-dibromoethane (0.820 mL, 9.48 mmol) was added dropwise over 5 min. The reaction was allowed to warm to room temp. and left to stir for 1 h. Ethyl acetate (50 mL) was added to the reaction mixture and this was washed with distilled water (50 mL×4) and brine (50 mL). The organic layer was separated and dried over $MgSO_4$, filtered and solvent removed in vacuo. Column chromatography (hexane/EtOAc 70:30) eluted the title compound as a colourless oil (0.600 g, 35%), $R_f$: 0.52 (hexane/EtOAc 75:25)

$^1$H NMR (270 MHz, CDCl$_3$) δ 1.40-1.45 (2H, dd, J=3.0 & 5.0 Hz, CH$_2$), 1.71-1.76 (2H, dd, J=3.7 & 5.0 Hz, CH$_2$), 2.39 (3H, s, ArCH$_3$), 3.89 (3H, s, ArCO$_2$CH$_3$), 7.39 (1H, s, ArH), 7.62 (1H, s, ArH) and 7.75 (1H, s, ArH);

$^{13}$C NMR (67.8 MHz, CDCl$_3$) δ 13.7 (CH$_2$), 18.4 (C), 21.4 (CH$_3$), 52.4 (CH$_3$), 122.4 (C), 123.4 (CH), 129.6 (CH), 130.9 (C), 131.7 (CH), 136.5 (C), 139.2 (C) and 166.7 (C=O);

HPLC (80% CH$_3$CN in H$_2$O) t$_r$=3.220 (98.85%);

LCMS (APCI), m/z 216.09 (M$^+$+H, 100%), 157.92 ((M$^+$+H)—CO$_2$CH$_3$, 92); Anal. Calcd. for C$_{13}$H$_{13}$NO$_2$: C 72.54, H 6.09, N 6.51. Found: C 72.30, H 6.04, N 6.38%.

3-Bromomethyl-5-(1-cyano-cyclopropyl)-benzoic acid methyl ester (TJA01100)

$C_{13}H_{12}BrNO_2$ MW 294.15

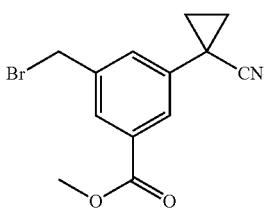

To a solution of sodium bromate (2.53 g, 16.8 mmol) in distilled H$_2$O (12 mL) was added TJA01099 (0.600 g, 2.79 mmol) in ethyl acetate (6 mL). To this clear mixture a solution of sodium hydrogen sulphate (2.02 g, 16.8 mmol) in distilled H$_2$O (24 mL) was added drop wise with vigorous stirring over 15 min. The reaction mixture was stirred for a further 4 h at room temperature. The ethyl acetate was separated and diethyl ether (50 mL) added. This was then washed with saturated Na2SO$_{3(aq)}$ (50 mL) distilled water (50 ml×2) and brine (50 mL). Dried over MgSO$_4$ and solvent removed in vacuo. Column chromatography (hexane/ethyl acetate 75:25) eluted the title compound as a white crystalline solid (0.760 g, 96%), mp 78.3-79.8° C.;

R$_f$: 0.35 (hexane/ethyl acetate 75:25), c.f 0.47 (TJA01091);

$^1$H NMR (270 MHz, CDCl$_3$) δ 1.44-1.49 (2H, dd, J=2.7 & 5.2 Hz, CH$_2$), 1.76-1.79 (2H, dd, J=2.7 & 4.9 Hz, CH$_2$), 3.91 (3H, s, ArCO$_2$CH$_3$), 4.48 (2H, s, ArCH$_2$Br), 7.59 (1H, s, ArH), 7.76 (1H, s, ArH) and 7.97 (2H, s, ArH);

$^{13}$C NMR (69.5 MHz, CDCl$_3$) δ 13.7 (CH$_2$), 18.7 (C), 31.9 (CH$_2$), 52.6 (CH$_3$), 121.9 (C), 126.1 (CH), 129.5 (CH), 131.3 (CH), 131.7 (C), 137.5 (C), 139.2 (C) and 165.9 (C=O);

HPLC (80% CH$_3$CN in H$_2$O) t$_r$=3.138 (100%);

LCMS (APCI), m/z 296.14 ($^{81}$BrM$^+$+H, 65%), ($^{79}$BrM$^+$+H, 70), 214.07 ((M$^+$+H)−Br, 100).

3-(1-Cyano-cyclopropyl)-5-[1,2,4]triazol-1-ylmethyl-benzoic acid methyl ester (TJA01101)

C$_{15}$H$_{14}$N$_4$O$_2$ MW 282.11

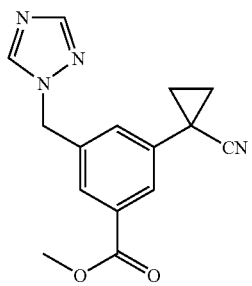

TJA01100 (0.790 g, 2.69 mmol), 1,2,4-triazole (0.278 g, 0.403 mmol), potassium carbonate (0.372 g, 2.69 mmol), potassium iodide (0.026 g, 0.158 mmol) and acetone (50 mL) were loaded to an r.b. flask. With vigorous stirring this mixture was set to reflux (60° C.) for 16 h. The reaction mixture was allowed to cool and acetone was removed in vacuo. The residues were taken up in ethyl acetate (50 mL) and washed with distilled water (50 mL×3) and brine (50 mL). Dried over MgSO$_4$ and solvent removed in vacuo to leave a dark brown syrup. Column chromatography (hexane/ethyl acetate 75:25 then ethyl acetate) eluted the title compound as a colourless viscous oil (0.444 g, 59%)

R$_f$: 0.15 (ethyl acetate);

$^1$H NMR (300 MHz, CDCl$_3$) δ 1.39-1.45 (2H, dd, J=2.8 & 5.8 Hz, CH$_2$), 1.76-1.80 (2H, dd, J=3.1 & 5.6 Hz, CH$_2$), 3.89 (3H, s, ArCO$_2$CH$_3$), 5.38 (2H, s, ArCH$_2$N), 7.49 (1H, s, ArH), 7.80 (1H, s, ArH), 7.82 (1H, s, ArH), 7.98 (1H, s, C$_2$H$_2$N$_3$), and 8.12 (1H, s, C$_2$H$_2$N$_3$);

$^{13}$C NMR (69.5 MHz, CDCl$_3$) δ (13.8 (CH$_2$), 18.8 (C), 52.7 (CH$_3$), 52.9 (CH$_2$), 121.8 (C), 126.5 (CH), 128.3 (CH), 130.3 (CH), 131.9 (C), 136.2 (C), 137.9 (C), 143.4 (CH), 152.7 (CH) and 165.8 (C=O);

HPLC (90% CH$_3$CN in H$_2$O) t$_r$=1.935 (100%);

LCMS (APCI), m/z 283.43 (M$^+$+H, 100%), 214.33 ((M$^+$+H)—C$_2$H$_2$N$_3$, 75);

Anal. Calcd. for C$_{15}$H$_{14}$N$_4$O$_2$: C 63.82, H 5.00, N 19.85 Found: C 63.50, H 5.01, N 19.80%.

1-(3-Hydroxymethyl-5-[1,2,4]triazol-1-ylmethyl-phenyl)-cyclopropanecarbonitrile (TJA01105)

C$_{14}$H$_{14}$N$_4$O MW 254.29

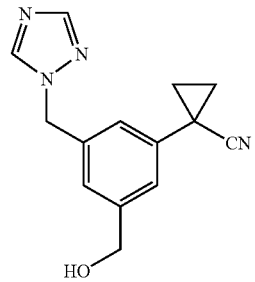

A 25 mL r.b. flask was loaded with TJA01101 (0.391 g, 1.39 mmol) and polyethylene glycol 400 (5.0 g). The mixture was heated to 80° C. with stirring until a solution had formed. Sodium borahydride (0.157 g, 4.15 mmol) was added carefully resulting in evolution of gas. The reaction mixture was stirred vigorously at 80° C. for 16 h. An extremely viscous glue formed that gradually dissolved in dichloromethane (50 mL) with heating (40° C.). This solution was washed with 1M HCl$_{(aq)}$ (10 mL) and then carefully neutralised with sodium bicarbonate. Washed with distilled water (50 mL×4) and brine (50 mL), separated and dried over MgSO$_4$. Solvent removed in vacuo to leave a colourless viscous oil. Flash chromatography (20 g column, Flashmaster II, method TJA01097) eluted the title compound as a colourless viscous oil (0.274 g, 78%), R$_f$: 0.10 (ethyl acetate);

$^1$H NMR (300 MHz, CDCl$_3$) δ 1.36-1.40 (2H, dd, J=2.5 & 5.3 Hz, CH$_2$), 1.70-1.75 (2H, dd, J=2.6 & 5.4 Hz, CH$_2$), 1.89-1.94 (1H, t, J=5.8 Hz, ArCH$_2$OH), 4.66-4.68 (2H, d, J=5.7 Hz, ArCH$_2$OH), 5.31 (2H, s, ArCH$_2$N), 7.12 (1H, s, ArH), 7.14 (1H, s, ArH), 7.24 (1H, s, ArH), 7.95 (1H, s, NCHN), and 8.08 (1H, s, NCHN);

$^{13}$C NMR (69.5 MHz, CDCl$_3$) δ 13.8 (CH$_2$), 18.5 (CH$_2$), 53.3 (CH$_2$), 64.2 (CH$_2$), 122.3 (C), 124.2 (CH), 124.6 (CH), 125.5 (CH), 135.8 (C), 137.4 (C), 143.3 (CH), 143.3 (C) and 152.3 (CH);

HPLC (90% CH$_3$CN in H$_2$O) t$_r$=1.791 (100%);

LCMS (APCI), m/z 255.09 (M$^+$+H, 100%).

Methanesulfonic acid 4-[3-(1-cyano-cyclopropyl)-5-[1,2,4]triazol-1-ylmethyl-benzylsulfanyl]-phenyl ester (TJA01147)

C$_{21}$H$_{20}$N$_4$O$_3$S$_2$ MW 440.54

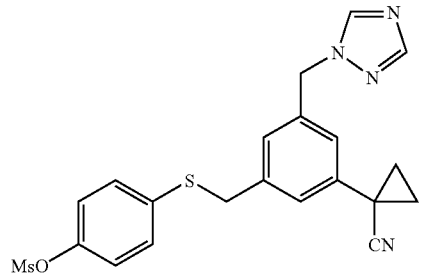

A dry 5 mL r.b. flask purged with N$_{2\ (g)}$ was loaded with TJA01110 (0.115 g, 0.472 mmol), TJA01105 (0.100 g, 0.393 mmol), TJA01130 (0.120, 0.590 mmol), diisopropylethylamine (89.0 µL, 0.511 mmol) and propionitrile (1.0 mL). The mixture was then set to stir at 93° C. After 2 h a further 1 equivalent of TJA01110 (0.096 g, 0.393 mmol) and diisopropylethylamine (68.4 µL, 0.393 mmol) were added. After 5 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over MgSO$_4$ and solvent removed in vacuo to leave yellow residues. Column chromatography (ethyl acetate) eluted the title compound as a yellow viscous oil (0.134 g, 77%), R$_f$: 0.32 (ethyl acetate);

$^1$H NMR (270 MHz, CDCl$_3$) δ 1.29-1.34 (2H, dd, J=5.0 & 7.9 Hz, CH$_2$), 1.69-1.74 (2H, dd, J=5.0 & 7.6 Hz, CH$_2$), 3.16 (3H, s, ArOSO$_2$CH$_3$), 4.01 (2H, s, ArCH$_2$S), 5.27 (2H, s, ArCH$_2$N), 6.94 (1H, s, ArH), 7.05 (1H, s, ArH), 7.08 (1H, s, ArH), 7.14-7.28 (4H, dd, J=8.6 & 27.9 Hz, ArH), 7.96 (1H, s, C$_2$H$_2$N$_3$) and 8.07 (1H, s, C$_2$H$_2$N$_3$);

$^{13}$C NMR (69.5 MHz, CDCl$_3$) δ 13.6 (CH$_2$), 18.6 (C), 37.7 (CH$_3$), 39.2 (CH$_2$), 52.9 (CH$_2$), 122.2 (C), 122.8 (CH), 124.1 (CH), 126.4 (CH), 127.5 (CH), 132.5 (CH), 134.6 (C), 136.1 (C), 137.5 (C), 139.3 (C), 143.3 (CH), 147.9 (C) and 152.6 (CH);

HPLC (90% CH$_3$CN in H$_2$O) t$_r$=1.853 (100%);

LCMS (APCI), m/z 441.23 (M$^+$+H, %).

1-(3-((1H-1,2,4-triazol-1-yl)methyl)-5-((4-hydroxyphenylthio)methyl)phenyl)cyclopropanecarbonitrile (TJA01153)

C$_{20}$H$_{18}$N$_4$OS MW 362.45

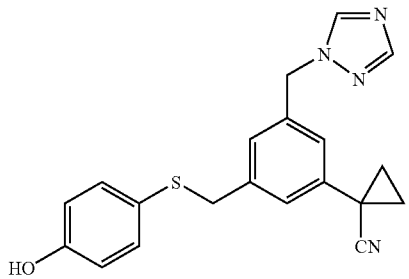

TJA01147 (0.129 g, 0.293 mmol) was dissolved in THF (3 mL) and methanol (2 mL) to which 2M NaOH$_{(aq)}$ (0.73 mL) was added. The mixture was set to stir at room temp. for 12 h. THF was removed under reduced pressure and the residues taken up in ethyl acetate (20 mL) and washed with 2M KHSO$_{4\ (aq)}$ (20 mL), distilled water (20 mL×2) and brine (20 mL). The organic layer was then dried over MgSO$_4$ and solvent removed under reduced pressure to leave a colourless viscous oil. Column chromatography (dichloromethane/acetone 80:20) eluted the title compound as a white solid (0.076 g, 72%), R$_f$: 0.25 (dichloromethane/acetone 80:20);

$^1$H NMR (270 MHz, CDCl$_3$) δ 1.31-1.35 (2H, dd, J=5.3 & 8.2 Hz, CH$_2$), 1.68-1.73 (2H, dd, J=5.2 & 7.6 Hz, CH$_2$), 3.83 (2H, s, ArCH$_2$S), 5.21 (2H, s, ArCH$_2$N), 6.65-6.70 (3H, m, ArH), 6.99-7.04 (3H, m, ArH), 7.11 (1H, s, ArH), 7.91 (1H, s, C$_2$H$_2$N$_3$), 7.99 (1H, s, C$_2$H$_2$N$_3$) and 8.12 (1H, s, ArOH);

$^{13}$C NMR (69.5 MHz, CDCl$_3$) δ 13.6 (CH$_2$), 18.4 (C), 41.1 (CH$_2$), 53.3 (CH$_2$), 116.5 (CH), 122.2 (C), 123.6 (C), 124.5 (CH), 126.5 (CH), 127.8 (CH), 134.9 (C), 135.8 (CH), 137.4 (C), 140.7 (C), 143.0 (CH), 151.7 (CH) and 156.7 (C);

HPLC (90% CH$_3$CN in H$_2$O) t$_r$=1.843 (93.71%);

LCMS (APCI), m/z 363.35 (M$^+$+H, %).

4-((3-((1H-1,2,4-triazol-1-yl)methyl)-5-(1-cyanocyclopropyl)benzyl)sulfanyl)phenyl sulfamate (TJA01156, STX1732)

C$_{20}$H$_{19}$N$_5$O$_3$S$_2$ MW 441.53

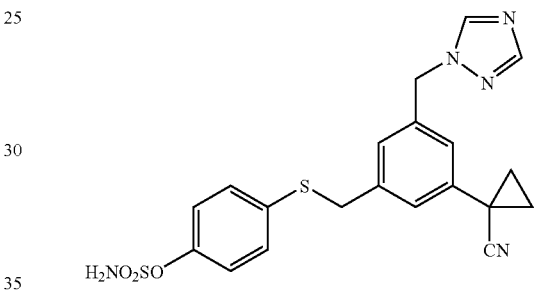

Sulfamoyl chloride in toluene (0.60 M, 1.42 mL) was transferred to a 10 mL r.b. flask and the solvent removed under vacuum at 30° C. On cooling a white solid formed to which was added N,N-dimethylacetamide (1.5 mL) to form a colourless solution. TJA01153 (0.062 g, 0.171 mmol) was added and the solution left to stir at room temperature under N$_{2\ (g)}$ for 72 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over MgSO$_4$ and solvent removed in vacuo to leave off white residues. Column chromatography (dichloromethane/acetone 80:20) eluted the title compound as a colourless viscous oil (0.055 g, 73%), R$_f$: 0.22 (dichloromethane/acetone 80:20);

$^1$H NMR (270 MHz, CDCl$_3$) δ 1.39-1.44 (2H, dd, J=5.0 & 7.9 Hz, CH$_2$), 1.74-1.79 (2H, dd, J=5.1 & 7.8 Hz, CH$_2$), 4.01 (2H, s, ArCH$_2$SAr), 5.21 (2H, s, ArCH$_2$N), 6.55 (1H, s, ArH), 6.88 (2H, s, ArOSO$_2$NH$_2$), 7.03 (1H, s, ArH), 7.11-7.21 (5H, m, ArH), 7.54 (1H, s, C$_2$H$_2$N$_3$) and 7.85 (1H, s, C$_2$H$_2$N$_3$);

$^{13}$C NMR (69.5 MHz, CDCl$_3$) δ 13.7 (CH$_2$), 18.7 (C), 38.3 (CH$_2$), 53.2 (CH$_2$), 122.2 (C), 123.4 (CH), 123.9 (CH), 126.5 (CH), 126.6 (CH), 132.4 (CH), 132.9 (C), 135.6 (C), 137.6 (C), 140.1 (C), 142.9 (CH), 149.3 (C) and 151.1 (CH);

HPLC (90% CH$_3$CN in H$_2$O) t$_r$=1.791 (100%);

LCMS (APCI), m/z 442.30 (M$^+$+H, 100%), 363.41 (M$^+$−SO$_2$NH$_2$, 35%).

Synthesis of STX1761

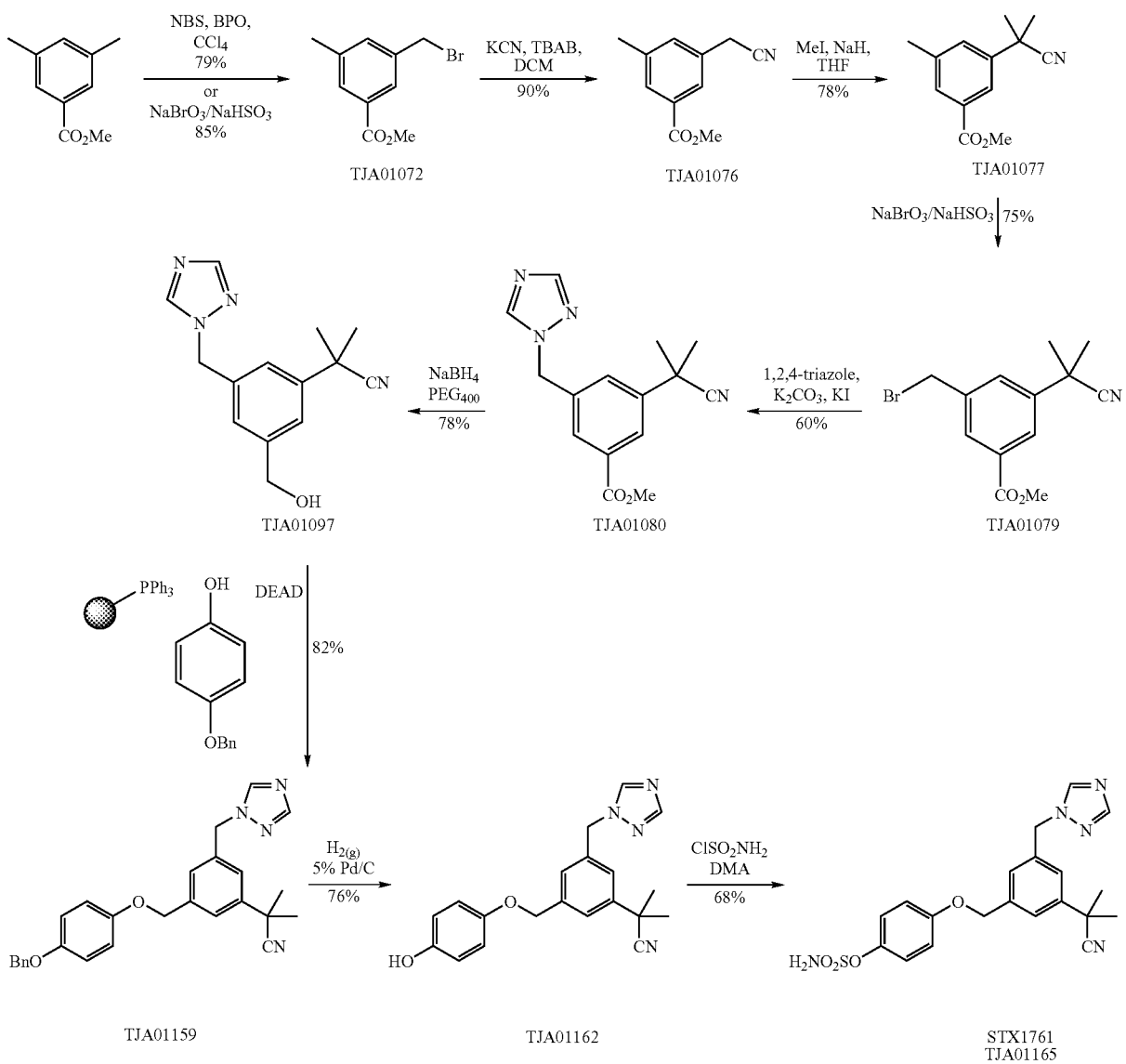

2-(3-((1H-1,2,4-triazol-1-yl)methyl)-5-((4-(benzyloxy)phenoxy)methyl)phenyl)-2-methylpropanenitrile (TJA01159)

$C_{27}H_{26}N_4O_2$ MW 438.52

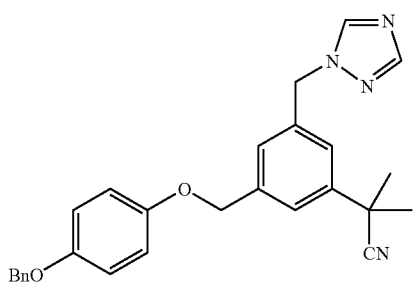

A dry 25 mL flask was loaded with TJA01097 (0.150 g, 0.586 mmol) and 4-(benzyloxy)phenol (0.098 g, 0.488 mmol) and purged with $N_{2\,(g)}$. Anhydrous dichloromethane (3 mL) was added to form a clear solution and to this was added triphenylphosphine polystyrene (0.586 g, 0.586 mmol) and the mixture cooled to 0° C. Diethylazodicarboxylate (92.3 µL, 0.586 mmol) was added dropwise and the reaction allowed to warm to room temperature and left to stir under $N_{2\,(g)}$ for 16 h. The reaction mixture was then filtered to remove the polystyrene which was washed with dichloromethane (6×25 mL). These washings were combined with the filtrate and washed with distilled $H_2O$ (2×25 mL) and brine (25 mL) then dried over $MgSO_4$ and solvent removed in vacuo. Column chromatography (ethyl acetate) eluted the title compound as a light yellow solid (0.175 g, 82%), $R_f$: 0.39 (ethyl acetate);

$^1H$ NMR (270 MHz, $CDCl_3$) δ 1.70 (6H, s, $ArC(CH_3)_2$ CN), 4.98 (2H, s, $ArCH_2O$), 5.01 (2H, s, $ArCH_2O$), 5.37 (2H, s, ArCH$_2$N), 6.84-6.92 (4H, m, ArH), 7.29-7.49 (8H, m, ArH), 7.99 (1H, s, C$_2$H$_2$N$_3$) and 8.10 (1H, s, C$_2$H$_2$N$_3$);

$^{13}$C NMR (69.5 MHz, CDCl$_3$) δ 29.2 (CH$_3$), 37.2 (C), 53.3 (CH$_2$), 70.1 (CH$_2$), 70.7 (CH$_2$), 115.8 (CH), 115.9 (CH), 124.1 (C), 124.3 (CH), 124.5 CH), 126.4 (CH), 127.6 (CH), 128.0 (CH), 128.7 (CH), 136.1 (C), 137.2 (C), 139.4 (C), 142.9 (C), 143.3 (CH), 152.5 (CH), 152.8 (C) and 153.5 (C);

HPLC (90% CH$_3$CN in H$_2$O) t$_r$=2.406 (94.36%);
LCMS (APCI), m/z 439.47 (M$^+$+H, 100%).

2-(3-((1H-1,2,4-triazol-1-yl)methyl)-5-((4-hydroxyphenoxy)methyl)phenyl)-2-methylpropanenitrile (TJA01162)

C$_{20}$H$_{20}$N$_4$O$_2$ MW 348.40

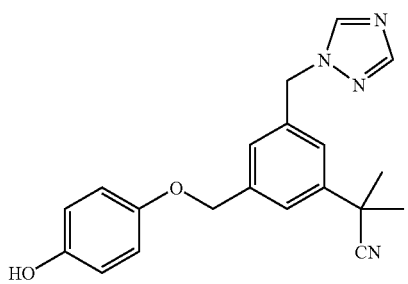

TJA01159 (0.100 g, 0.228 mmol) was dissolved in THF (2.5 mL) and MeOH (2.5 mL) in an r.b. flask to which was added 5% Pd/C (0.010 g) to form a black suspension on vigorous stirring. The flask was evacuated and back filled with H$_2$ $_{(g)}$ via a balloon (×3) and then left to stir for 8 h when more 5% Pd/C (0.010 g) was added. The reaction was then left to stir for a further 16 h. The reaction mixture was filtered through celite which was subsequently washed with THF (30 mL×2). Solvent was removed in vacuo to leave a brown residue. Column chromatography (ethyl acetate) eluted the title compound as a colourless viscous oil (0.060 g, 76%), R$_f$: 0.30 (ethyl acetate);

$^1$H NMR (270 MHz, CDCl$_3$) δ 1.70 (6H, s, ArC(CH$_3$)$_2$CN), 4.97 (2H, s, ArCH$_2$O), 5.17 (1H, s, ArOH), 5.37 (2H, s, ArCH$_2$N), 6.73-6.82 (4H, m, ArH), 7.22 (1H, s, ArH), 7.33 (1H, s, ArH), 7.49 (1H, s, ArH), 7.99 (1H, s, C$_2$H$_2$N$_2$) and 8.10 (1H, s, C$_2$H$_2$N$_2$);

HPLC (90% CH$_3$CN in H$_2$O) t$_r$=1.870 (97.88%);
LCMS (APCI), m/z 349.43 (M$^+$+H, 100%).

4-(3-((1H-1,2,4-triazol-1-yl)methyl)-5-(2-cyanopropan-2-yl)benzyl)phenoxy sulfamate (TJA01165, STX1761)

C$_{20}$H$_{21}$N$_5$O$_4$S MW 427.48

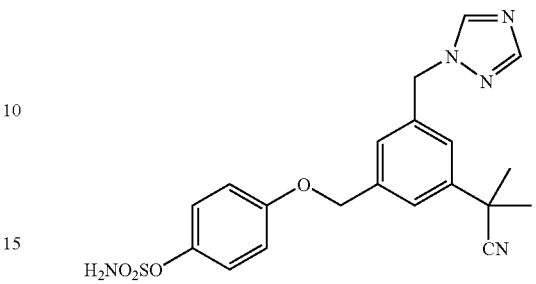

Sulfamoyl chloride in toluene (0.60 M, 1.41 mL) was transferred to a 10 mL r.b. flask and the solvent removed under vacuum at 30° C. On cooling a white solid formed to which was added N,N-dimethylacetamide (1.5 mL) to form a colourless solution. TJA01162 (0.059 g, 0.169 mmol) was added and the solution left to stir at room temperature under N$_2$ $_{(g)}$ for 16 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over MgSO$_4$ and solvent removed in vacuo to leave off white residues. Column chromatography (dichloromethane/acetone 80:20) eluted the title compound as a white solid (0.049 g, 68%), R$_f$: 0.51 (dichloromethane/acetone 80:20);

$^1$H NMR (400 MHz, DMSO-d$_6$) δ 1.68 (6H, s, ArC(CH$_3$)$_2$CN), 5.11 (2H, s, ArCH$_2$OAr), 5.48 (2H, s, ArCH$_2$N), 7.05-7.21 (4H, dd, J=8.8 & 53.2 Hz, AA'BB'), 7.30 (1H, s, ArH), 7.46 (1H, s, ArH), 7.57 (1H, s, ArH), 7.91 (2H, s, ArOSO$_2$NH$_2$), 8.00 (1H, s, C$_2$H$_2$N$_2$) and 8.69 (1H, s, C$_2$H$_2$N$_2$);

$^{13}$C NMR (100.5 MHz, DMSO-d$_6$) δ 18.3, 26.6, 41.8, 59.3, 105.6, 113.4, 114.2, 114.4, 116.5, 127.4, 128.2, 132.2, 133.8, 134.4, 141.9 and 146.6 (one overlapping signal);

HPLC (70% CH$_3$CN in H$_2$O) t$_r$=2.441 (100%);
LCMS (APCI), m/z 428.39 (M$^+$+H, 100%).

Synthesis of STX1794

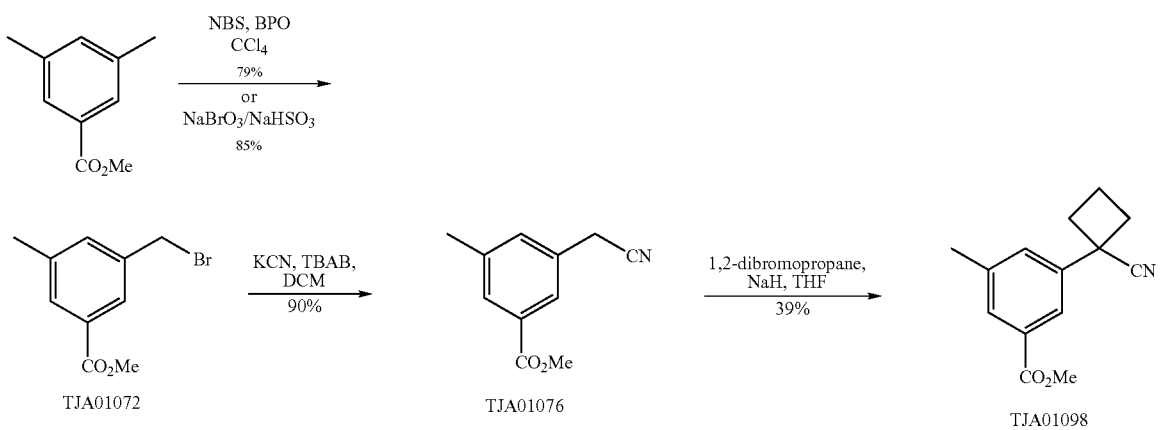

-continued
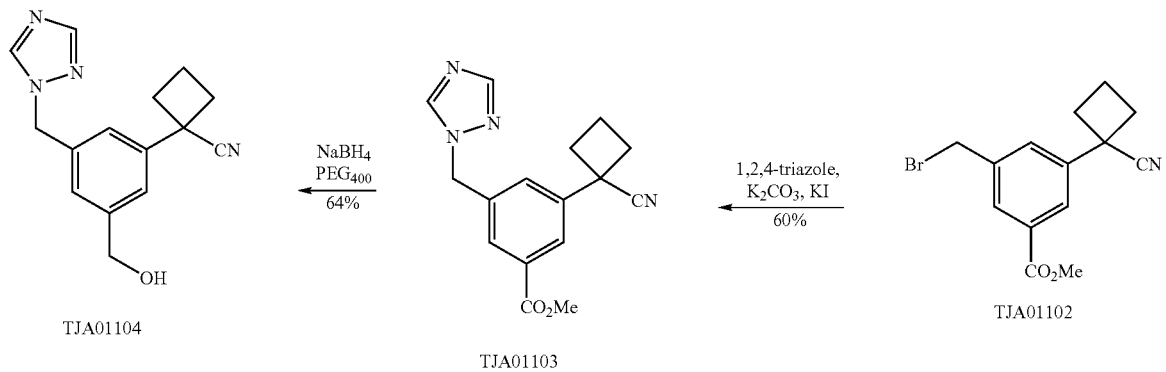
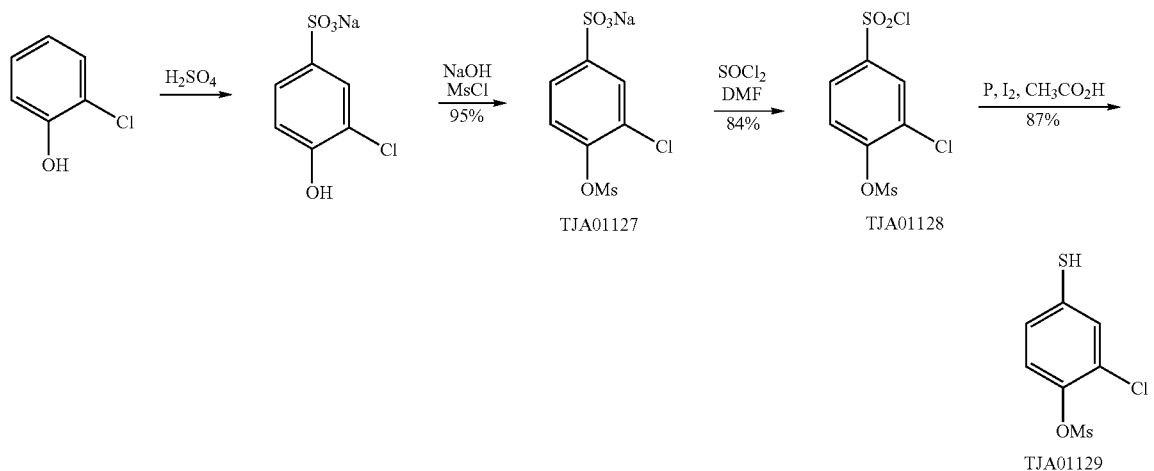
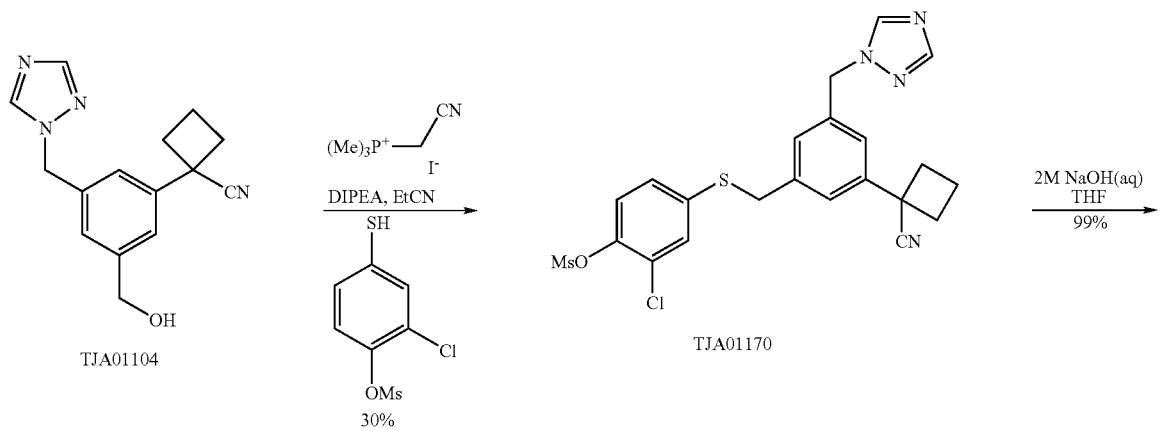
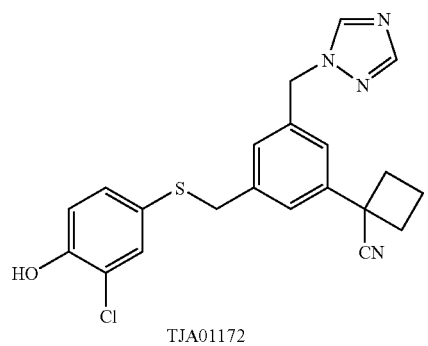

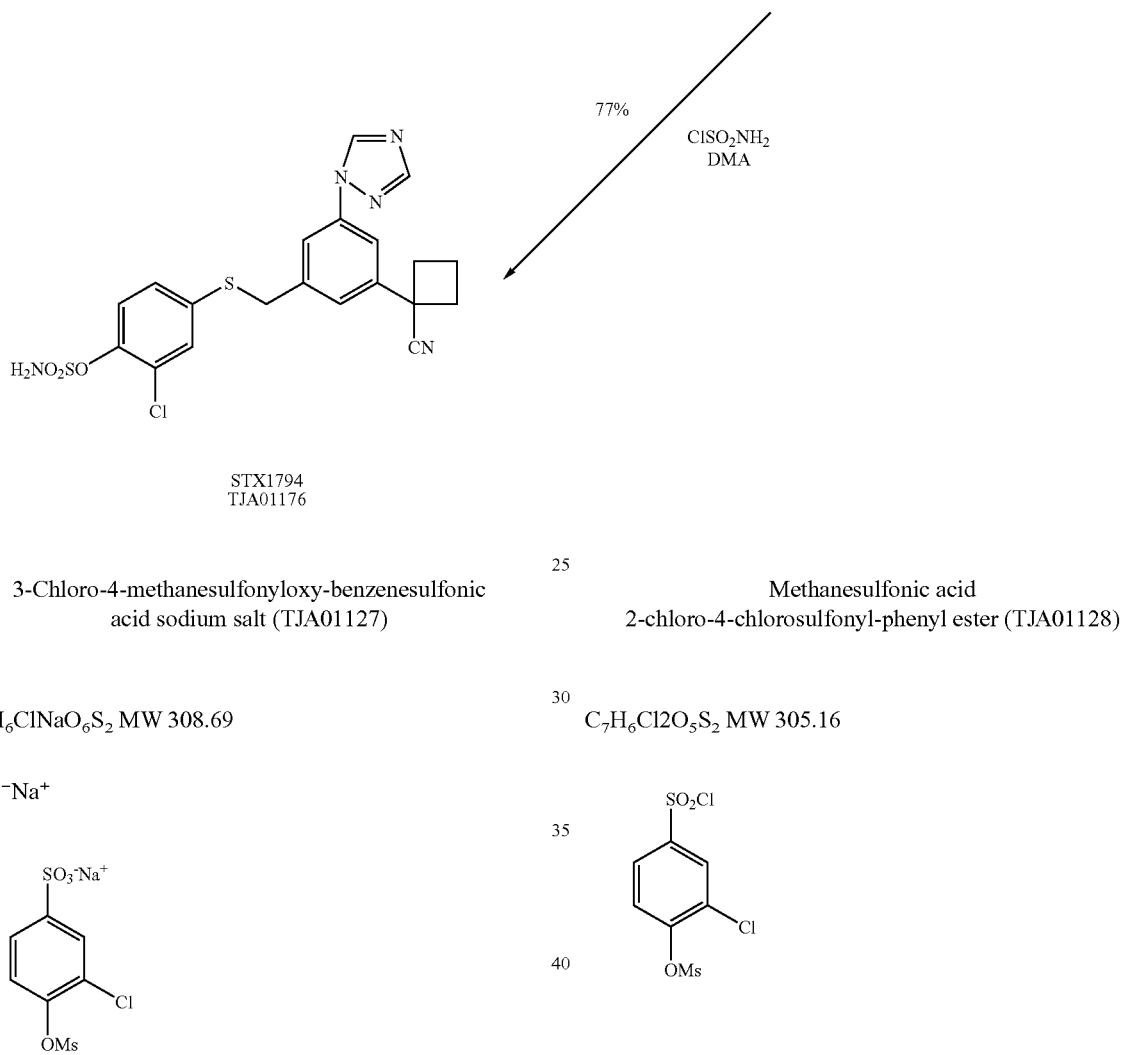

STX1794
TJA01176

3-Chloro-4-methanesulfonyloxy-benzenesulfonic acid sodium salt (TJA01127)

$C_7H_6ClNaO_6S_2$ MW 308.69

SO$_3^-$Na$^+$

Methanesulfonic acid 2-chloro-4-chlorosulfonyl-phenyl ester (TJA01128)

$C_7H_6Cl2O_5S_2$ MW 305.16

4-hydroxy-3-chlorobenzenesulfonic acid sodium salt (11.53 g, 50.0 mmol) and sodium hydroxide (2.00 g, 50.0 mmol) were dissolved in distilled water (50 mL) and the solution cooled to 0° C. Methane sulfonyl chloride (4.25 mL, 55.0 mmol) was added dropwise with stirring and the mixture then allowed to warm to room temp. and left for 2 h. Brine (20 mL) was added and the solution left to stand for 1 h with the formation of white crystalline solid. The solids were filtered, recrystallised (brine), and dried under vacuum to give the title compound as a white crystalline solid (9.40 g, 61%), mp>250° C.;

$^1$H NMR (300 MHz, DMSO-d$_6$) δ 3.31 (3H, s, ArOSO$_2$CH$_3$), 7.48-7.51 (1H, d, J=8.4 Hz, ArH), 7.59-7.62 (1H, dd, J=2.2 & 8.4 Hz, ArH) and 7.69-7.72 (1H, d, J=2.2 Hz, ArH);

$^{13}$C NMR (69.5 MHz, DMSO-d$_6$) δ 39.1 (CH$_3$), 124.4 (CH), 126.3 (C), 126.5 (CH), 128.3 (CH), 145.3 (C) and 148.8 (C).

Thionyl chloride (30 mL) was cooled to 0° C. Cautiously, with stirring, TJA01127 (8.60 g, 28.0 mmol) was added followed by DMF (0.5 mL). The reaction mixture was subsequently heated to reflux (79° C.) for 1 h (or until evolution of gas has ceased) and then cooled. Thionyl chloride was removed in vacuo and the resulting yellow residues were taken up in dichloromethane (50 mL) and distilled water (50 mL) carefully added. The organic layer was separated and washed with distilled water (50 mL×2) and brine (50 mL), dried over MgSO$_4$ and solvent removed in vacuo to leave yellow residues. Recrystallisation (dichloromethane/hexane) gave the title compound as a white crystalline solid (7.10 g, 84%), $^1$H NMR (300 MHz, CDCl$_3$) δ 3.37 (3H, s, ArOSO$_2$CH$_3$), 7.70-7.73 (1H, d, J=8.8 Hz, ArH), 7.99-8.03 (1H, dd, J=2.4 & 8.8 Hz, ArH) and 8.19-8.20 (1H, d, J=2.4 Hz, ArH);

$^{13}$C NMR (69.5 MHz, CDCl$_3$) δ 39.6 (CH$_3$), 125.6 (CH), 127.2 (CH), 128.8 (C), 129.9 (CH), 143.1 (C) and 149.9 (C);

HPLC (90% CH$_3$CN in H$_2$O) t$_r$=2.489 (99.62%);.

Methanesulfonic acid 2-chloro-4-mercapto-phenyl ester (TJA01129)

$C_7H_7ClO_3S_2$ MW 238.71

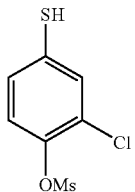

A 50 mL r.b. flask was loaded with red phosphorus powder (0.630 g, 20.5 mmol), iodine (0.035 g, 0.137 mmol) and acetic acid (7 mL). Cautiously TJA01128 (2.50 g, 8.19 mmol) was added and the reaction mixture then set to reflux (118° C.) for 2 h. Distilled water (1.5 mL) was added and the mixture left to reflux for a further 1 h. Reaction allowed to cool. Chloroform (30 mL) and distilled water (30 mL) were added. The organic layer was separated and washed with distilled water (30 mL×3) and brine (30 mL). Dried over $MgSO_4$, filtered and solvent removed in vacuo. Column chromatography (ethyl acetate/hexane 50:50) eluted the title compound as a colourless viscous oil (1.68 g, 87%), $R_f$: 0.71 (ethyl acetate);
$^1$H NMR (300 MHz, $CDCl_3$) δ 3.24 (3H, s, $ArOSO_2CH_3$), 3.56 (1H, s, ArSH), 7.18-7.22 (1H, dd, J=2.3 & 8.5 Hz, ArH), 7.30-7.33 (1H, d, J=8.1 Hz, ArH) and 7.39-7.40 (1H, d, J=2.2 Hz, ArH);
$^{13}$C NMR (69.5 MHz, $CDCl_3$) δ 38.7 ($CH_3$), 125.1 (CH), 127.4 (C), 128.9 (CH), 130.9 (CH), 132.1 (C) and 143.2 (C);
HPLC (90% $CH_3CN$ in $H_2O$) $t_r$=1.811 (92.46%);
LCMS (APCI), m/z 239.01 ($^{37}ClM^+$–H, 10%), 239.01 ($^{35}ClM^+$–H, 30).

4-((3-((1H-1,2,4-triazol-1-yl)methyl)-5-(1-cyanocyclobutyl)benzyl)sulfanyl)-2-chlorophenyl methanesulfonate (TJA01170)

$C_{22}H_{21}ClN_4O_3S_2$ MW 489.01

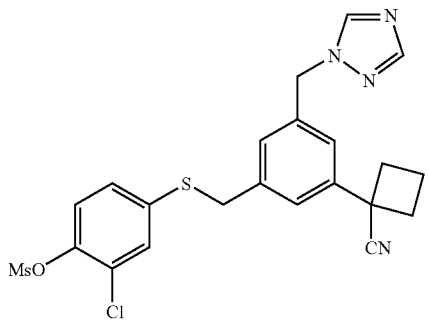

A dry 5 mL r.b. flask purged with $N_{2\,(g)}$ was loaded with TJA01110 (0.107 g, 0.447 mmol), TJA01104 (0.100 g, 0.373 mmol), TJA01129 (0.133, 0.559 mmol), diisopropylethylamine (84.5 µL, 0.485 mmol) and propionitrile (1.0 mL). The mixture was then set to stir at 93° C. under $N_{2\,(g)}$. After 3 h a further 1 equivalent of TJA01110 (0.091 g, 0.373 mmol), TJA01129 (0.087, 0.373) and diisopropylethylamine (65.0 µL, 0.373 mmol) were added. After 20 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over $MgSO_4$ and solvent removed in vacuo to leave yellow residues. Column chromatography (ethyl acetate) eluted the title compound as a yellow viscous oil (0.054 g, 30%), $R_f$: 0.43 (ethyl acetate);
$^1$H NMR (270 MHz, $CDCl_3$) δ 1.96-2.08 (1H, m, $CH_2$), 2.31-2.58 (3H, m, $CH_2$), 2.70-2.83 (2H, m, $CH_2$), 3.24 (3H, s, $ArOSO_2CH_3$), 4.05 (2H, s, $ArCH_2S$), 5.31 (2H, s, $ArCH_2N$), 7.00 (1H, s, ArH), 7.08-7.32 (5H, m, ArH), 7.96 (1H, s, $C_2H_2N_3$) and 8.10 (1H, s, $C_2H_2N_3$);
$^{13}$C NMR (69.5 MHz, $CDCl_3$) δ 17.2 (C), 34.7 ($CH_2$), 38.8 ($CH_2$), 38.9 ($CH_3$), 40.0 ($CH_2$), 53.0 ($CH_2$), 123.9 (C), 124.4 (CH), 124.9 (CH), 126.4 (CH), 127.3 (C), 127.7 (CH), 129.9 (CH), 132.0 (CH), 136.2 (C), 136.3 (C), 138.7 (C), 141.3 (C), 143.4 (CH), 143.9 (C) and 152.5 (CH);
HPLC (90% $CH_3CN$ in $H_2O$) $t_r$=3.086 (99.60%);
LCMS (APCI), m/z 489.27 ($M^+$+H, 100%).

1-(3-((1H-1,2,4-triazol-1-yl)methyl)-5-((3-chloro-4-hydroxyphenylthio)methyl)phenyl)cyclobutanecarbonitrile (TJA01172)

$C_{21}H_{19}ClN_4OS$ MW 410.92

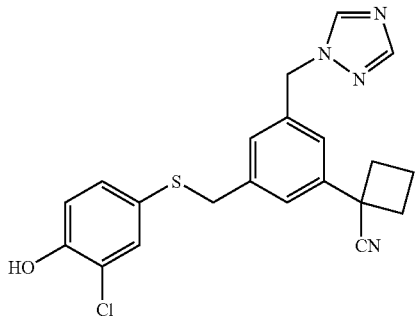

TJA01170 (0.050 g, 0.102 mmol) was dissolved in THF (2 mL) and methanol (2 mL) to which 2M $NaOH_{(aq)}$ (0.260 mL) was added. The mixture was set to stir at room temp. for 3 h. THF was removed under reduced pressure and the residues taken up in ethyl acetate (20 mL) and washed with 2M $KHSO_{4\,(aq)}$ (20 mL), distilled water (20 mL×2) and brine (20 mL). The organic layer was then dried over $MgSO_4$ and solvent removed under reduced pressure to leave the title compound as a light yellow viscous oil (0.039 g, 99%), $R_f$: 0.25 (dichloromethane/acetone 80:20);
$^1$H NMR (270 MHz, $CDCl_3$) δ 1.92-2.12 (1H, m, $CH_2$), 2.31-2.62 (3H, m, $CH_2$), 2.65-2.88 (2H, m, $CH_2$), 3.89 (2H, s, $ArCH_2SAr$), 5.28 (2H, s, $ArCH_2N$), 6.81-7.28 (6H, m, ArH), 7.99 (1H, s, $C_2H_2N_3$), 7.99 (1H, s, $C_2H_2N_3$) and 8.06 (1H, bs, ArOH);
$^{13}$C NMR (69.5 MHz, $CDCl_3$) δ 17.2 (C), 34.6 ($CH_2$), 39.9 ($CH_2$), 40.9 ($CH_2$), 53.3 ($CH_2$), 117.1 (CH), 120.6 (C), 124.0 (C), 124.1 (CH), 125.2 (C), 126.6 (CH), 127.9 (CH), 133.8 (CH), 134.6 (CH), 135.5 (C), 140.1 (C), 141.0 (C), 143.1 (CH), 151.9 (CH) and 152.3 (C);
HPLC (70% $CH_3CN$ in $H_2O$) $t_r$=2.902 (85.05%);
LCMS (APCI), m/z 411.45 ($M^+$+H, 100%).

4-((3-((1H-1,2,4-triazol-1-yl)methyl)-5-(1-cyanocyclobutyl)benzyl)sulfanyl)-2-chlorophenyl sulfamate (TJA01176, STX1794)

$C_{21}H_{20}ClN_5O_3S_2$ MW 490.00

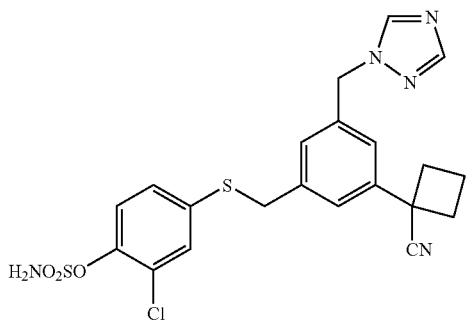

Sulfamoyl chloride in toluene (0.60 M, 2.86 mL) was transferred to an 10 mL r.b. flask and the solvent removed under vacuum at 30° C. On cooling a white solid formed to which was added N,N-dimethylacetamide (1.5 mL) to form a colourless solution. TJA01172 (0.039 g, 0.100 mmol) was added and the solution left to stir at room temperature under $N_{2\ (g)}$ for 60 h. The reaction mixture was then poured into distilled $H_2O$ (30 mL) and extracted with ethyl acetate (25 mL×2). The organic layers were combined and washed with distilled $H_2O$ (25 mL×4) and brine (25 mL×2). Dried over $MgSO_4$ and solvent removed in vacuo to leave off white residues. Column chromatography (dichloromethane/acetone 80:20) eluted the title compound as a white amorphous solid (0.037 g, 77%), $R_f$: 0.28 (dichloromethane/acetone 80:20);

$^1H$ NMR (270 MHz, $CDCl_3$) δ 2.04-2.13 (1H, m, $CH_2$), 2.44-2.67 (3H, m, $CH_2$), 2.80-2.87 (2H, m, $CH_2$), 4.06 (2H, s, $ArCH_2SAr$), 5.28 (2H, s, $ArCH_2N$), 6.56 (1H, s, ArH), 6.89-6.97 (1H, dd, J=2.2 & 8.6 Hz, ArH), 7.10 (2H, bs, $ArOSO_2NH_2$), 7.23-7.30 (4H, m, ArH), 7.62 (1H, s, $C_2H_2N_3$) and 7.86 (1H, s, $C_2H_2N_3$);

HPLC (70% $CH_3CN$ in $H_2O$) $t_r$=2.557 (99.59%);

LCMS (APCI), m/z 492.29 ($^{37}ClN^++H$, 40%), 490.27 ($^{35}ClM^++H$, 100).

Synthesis of STX1795

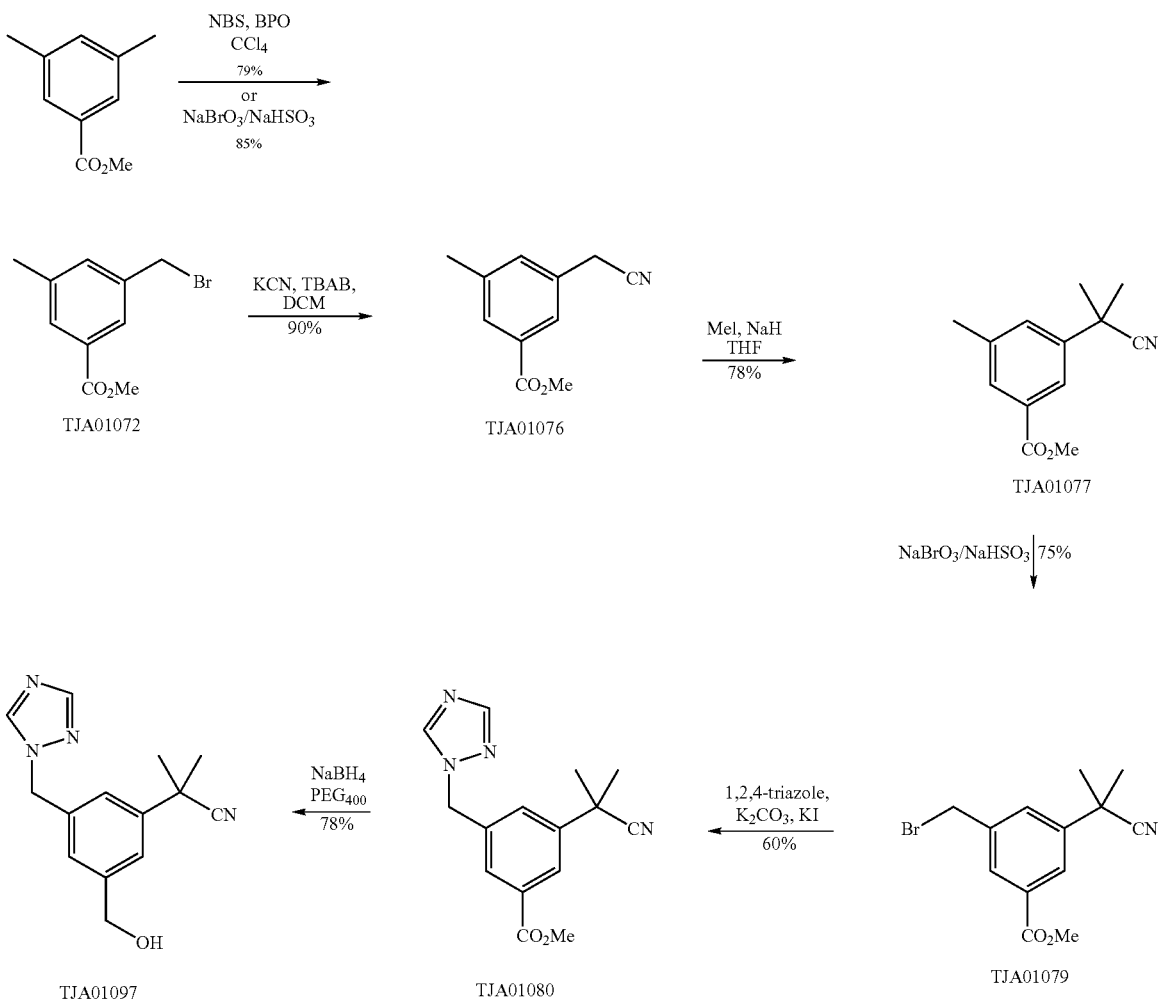

-continued
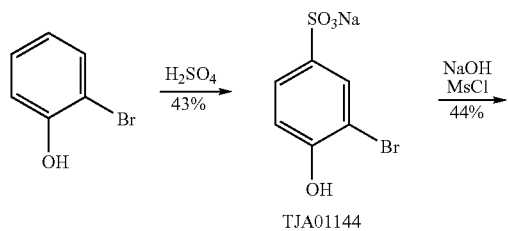
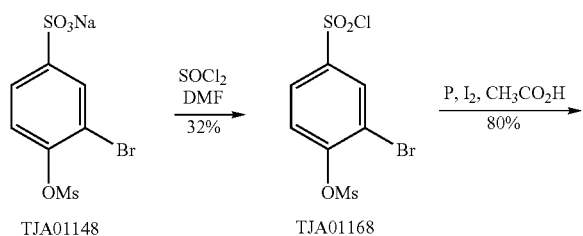
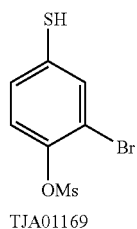
TJA01169
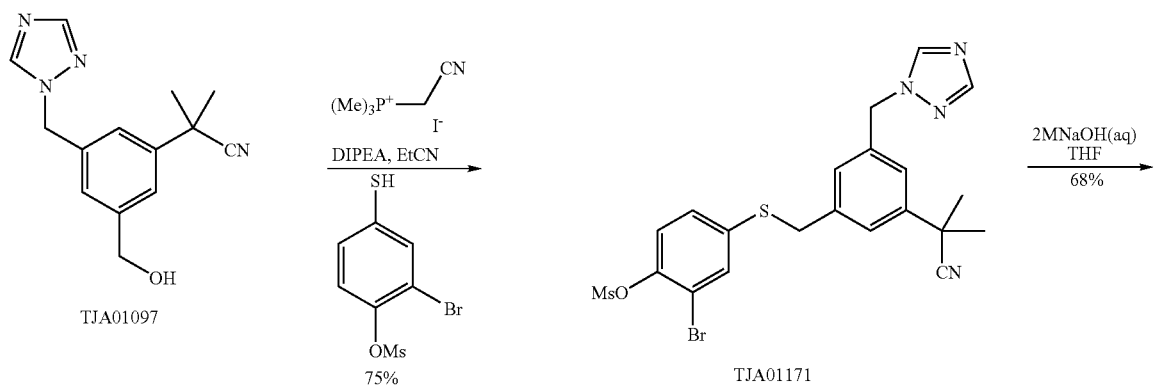
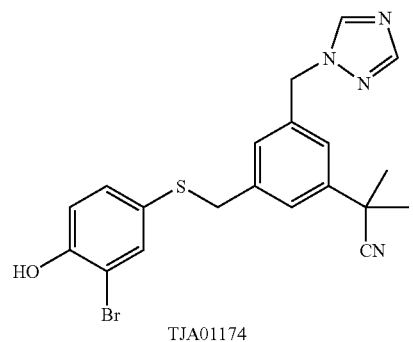
TJA01174

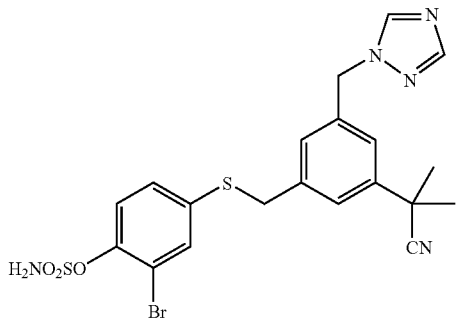

STX1795
TJA01179

3-Bromo-4-hydroxy-benzenesulfonic acid sodium salt (TJA01144)

$C_6H_4BrNaO_4S$ MW 275.05

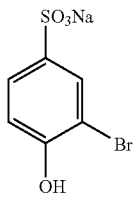

2-Bromophenol (20.0 g, 116 mmol) was added with stirring to a 250 mL r.b. flask containing sulphuric acid, 98%, (50 mL) and the mixture left to stir at 100° C. for 2 h. The reaction mixture was allowed to cool and then poured into brine (100 mL) and left to stand for 1 h. White solids formed and were collected via filtration, recrystallised (brine) and dried under reduced pressure to give the title compound as a white crystalline solid (13.7 g, 43%), mp>250° C.;

$^1$H NMR (270 MHz, DMSO-$d_6$) δ 6.92-6.95 (1H, d, J=8.4 Hz, ArH), 7.38-7.42 (1H, dd, J=2.0 & 8.4 Hz, ArH), 7.64-7.65 (1H, d, J=2.0 Hz, ArH) and 10.40-10.74 (1H, bs, ArOH);

$^{13}$C NMR (69.5 MHz, DMSO-$d_6$) δ 108.5 (C), 115.9 (CH), 126.7 (CH), 130.8 (CH), 141.1 (C) and 154.9 (C).

Sodium 3-bromo-4-methanesulfonoylbenzenesulfonate (TJA01148)

$C_7H_6BrNaO_6S_2$ MW 353.14

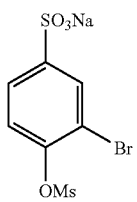

TJA01144 (13.8 g, 50.0 mmol) and sodium hydroxide (2.00 g, 50.0 mmol) were dissolved in distilled water (50 mL) and the solution cooled to 0° C. Methane sulfonyl chloride (4.25 mL, 55.0 mmol) was added dropwise with stirring and the mixture then allowed to warm to room temp. and left for 2 h. Brine (20 mL) was added and the solution left to stand for 1 h with the formation of white crystalline solid. The solids were filtered, recrystallised (brine), and dried under vacuum to give the title compound as a white crystalline solid (7.74 g, 44%), mp>250° C.;

$^1$H NMR (270 MHz, DMSO-$d_6$) δ 3.56 (3H, s, ArOSO$_2$CH$_3$), 7.49-7.53 (1H, d, J=12.3 Hz, ArH), 7.64-7.68 (1H, dd, J=2.2 & 8.4 Hz, ArH) and 7.85-7.88 (1H, d, J=6.2 Hz, ArH);

$^{13}$C NMR (69.5 MHz, DMSO-$d_6$) δ 39.4 (CH$_3$), 115.8 (C), 124.1 (CH), 127.1 (CH), 131.3 (CH), 146.5 (C) and 148.9 (C).

Methanesulfonic acid 2-bromo-4-chlorosulfonyl-phenyl ester (TJA01168)

$C_7H_6BrClO_5S_2$ MW 349.61

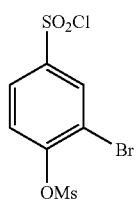

Thionyl chloride (30 mL) was cooled to 0° C. Cautiously, with stirring, TJA01148 (7.70 g, 21.8 mmol) was added followed by DMF (0.5 mL). The reaction mixture was subsequently heated to reflux (79° C.) for 1 h (or until evolution of gas has ceased) and then cooled. Thionyl chloride was removed in vacuo and the resulting yellow residues were taken up in dichloromethane (50 mL) and distilled water (50 mL) carefully added. The organic layer was separated and washed with distilled water (50 mL×2) and brine (50 mL), dried over MgSO$_4$ and solvent removed in vacuo to leave yellow residues. Recrystallisation (dichloromethane/hexane) gave the title compound as a white crystalline solid (2.47 g, 32%), ¹H NMR (270 MHz, CDCl₃) δ 3.36 (3H, s, ArOSO₂CH₃), 7.67-7.71 (1H, d, J=8.7 Hz, ArH), 8.02-8.06 (1H, dd, J=2.5 & 8.7 Hz, ArH) and 8.31-8.32 (1H, d, J=2.2 Hz, ArH);

¹³C NMR (69.5 MHz, CDCl₃) δ 39.8 (CH₃), 117.4 (C), 125.1 (CH), 127.8 (CH), 132.8 (CH), 143.2 (C) and 151.2 (C);

HPLC (90% CH₃CN in H₂O) t$_r$=2.108 (93.16%).

2-Bromo-4-mercaptophenyl methanesulfonate (TJA01169)

$C_7H_7BrO_3S_2$ MW 283.16

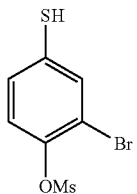

A 50 mL r.b. flask was loaded with red phosphorus powder (0.500 g, 16.1 mmol), iodine (0.027 g, 0.107 mmol) and acetic acid (7 mL). Cautiously TJA01168 (2.25 g, 6.44 mmol) was added and the reaction mixture then set to reflux (118° C.) for 2 h. Distilled water (1.5 mL) was added and the mixture left to reflux for a further 1 h. Reaction allowed to cool. Chloroform (30 mL) and distilled water (30 mL) were added. The organic layer was separated and washed with distilled water (30 mL×3) and brine (30 mL). Dried over MgSO₄, filtered and solvent removed in vacuo. Column chromatography (ethyl acetate/hexane 50:50) eluted the title compound as a yellow viscous oil (1.45 g, 80%), R$_f$: 0.41 (ethyl acetate);

¹H NMR (270 MHz, CDCl₃) δ 3.23 (3H, s, ArOSO₂CH₃), 3.54 (1H, s, ArSH), 7.18-7.24 (1H, dd, is J=2.2 & 8.6 Hz, ArH), 7.28-7.31 (1H, d, J=8.4 Hz, ArH) and 7.52-7.53 (1H, d, J=2.2 Hz, ArH);

¹³C NMR (69.5 MHz, CDCl₃) δ 38.9 (CH₃), 116.3 (C), 124.7 (CH), 129.7 (CH), 132.3 (C), 133.8 (CH) and 144.5 (C);

HPLC (90% CH₃CN in H₂O) t$_r$=2.604 (77.34%);

LCMS (APCI), m/z 283.10 (⁸¹BrM⁺-H, 50%), 281.10 (⁷⁹BrM⁺-H, 65).

Methanesulfonic acid 2-bromo-4-[3-(cyano-dimethyl-methyl)-5-[1,2,4]triazol-1-ylmethyl-benzylsulfanyl]-phenyl ester (TJA01171)

$C_{21}H_{21}BrN_4O_3S_2$ MW 521.45

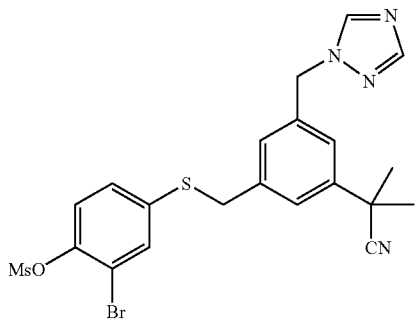

TJA01110 (0.114 g, 0.470 mmol) was added to a mixture of TJA01097 (0.100 g, 0.390 mmol), TJA01169 (0.161 g, 0.570 mmol), diisopropylethylamine (88.0 µL, 0.510 mmol) and propionitrile (1.0 mL) in a dry 5 mL r.b. flask purged with N₂ (g). The mixture was then set to stir at 92° C. After 2 h a further 1 equivalent of TJA01110 (0.094 g, 0.390 mmol), diisopropylethylamine (67.8 µL, 0.390 mmol) and TJA01169 (0.107 g, 0.380 mmol) was added. After 6 h this addition was repeated. After 20 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over MgSO₄ and solvent removed in vacuo to leave yellow residues. Column chromatography (ethyl acetate) eluted the title compound as a yellow viscous oil (0.152 g, 75%), R$_f$: 0.45 (dichloromethane/acetone 80:20).

¹H NMR (270 MHz, CDCl₃) δ 1.62 (6H, s, ArC(CH₃)₂CN), 3.25 (3H, s, ArOSO₂CH₃), 4.04 (2H, s, ArCH₂SAr), 5.31 (2H, s, ArCH₂N), 7.00 (1H, s, ArH), 7.16-7.31 (4H, m, ArH), 7.45-7.46 (1H, d, J=2.2 Hz, ArH), 7.24 (1H, s, ArH), 7.97 (1H, s, C₂H₂N₃) and 8.10 (1H, s, C₂H₂N₃);

¹³C NMR (69.5 MHz, CDCl₃) δ 29.1 (CH₃), 37.1 (C), 39.0 (CH₂), 39.1 (CH₃), 52.1 (CH₂), 116.3 (C), 123.8 (CH), 124.0 (C), 124.6 (CH), 126.0 (CH), 127.7 (CH), 130.8 (CH), 135.2 (CH), 136.3 (C), 138.8 (C), 143.0 (C), 143.4 (CH), 145.2 (C) and 152.2 (CH) (one overlapping signal);

HPLC (90% CH₃CN in H₂O) t$_r$=1.985 (99.16%);

LCMS (APCI), m/z 523.32 (⁸¹BrM⁺+H, 100%), 521.31 (⁷⁹BrM⁺+H, 85).

2-(3-((1H-1,2,4-triazol-1-yl)methyl)-5-((3-bromo-4-hydroxyphenylthio)methyl)phenyl)-2-methylpropanenitrile (TJA01174)

$C_{20}H_{19}BrN_4OS$ MW 443.36

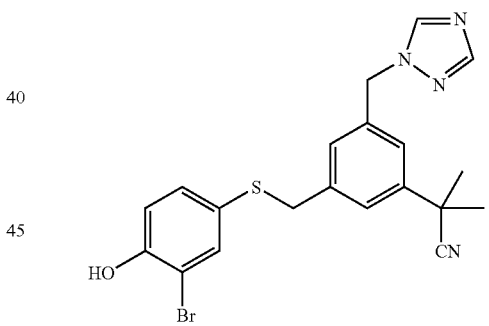

TJA01171 (0.150 g, 0.288 mmol) was dissolved in THF (3 mL) and methanol (2 mL) to which 2M NaOH$_{(aq)}$ (0.719 mL) was added. The mixture was set to stir at room temp. for 4 h. THF was removed under reduced pressure and the residues taken up in ethyl acetate (20 mL) and washed with 2M KHSO₄ $_{(aq)}$ (20 mL), distilled water (20 mL×2) and brine (20 mL). The organic layer was then dried over MgSO₄ and solvent removed under reduced pressure. Column chromatography (dichloromethane/acetone 80:20) eluted the title compound as a colourless viscous oil (0.087 g, 68%), R$_f$: 0.41 (dichloromethane/acetone 80:20).

¹H NMR (270 MHz, CDCl₃) δ 1.63 (6H, s, ArC(CH₃)₂CN), 3.90 (2H, s, ArCH₂SAr), 5.29 (2H, s, ArCH₂N), 6.75 (1H, bs, ArOH), 6.83-6.87 (2H, m, ArH), 7.06-7.09 (1H, dd, J=2.2 & 8.4 Hz, ArH), 7.14 (1H, s, ArH), 7.24 (1H, s, ArH), 7.30-7.31 (1H, d, J=2.2 Hz, ArH), 7.99 (1H, s, C₂H₂N₃) and 8.04 (1H, s, C₂H₂N₃);

$^{13}$C NMR (69.5 MHz, CDCl$_3$) δ 29.1 (CH$_3$), 37.1 (C), 41.0 (CH$_2$), 53.3 (CH$_2$), 110.3 (C), 116.8 (C), 123.6 (CH), 124.1 (C), 126.1 (CH), 127.9 (CH), 134.6 (CH), 135.7 (C), 137.2 (CH), 140.0 (C), 142.7 (C), 143.2 (CH), 152.2 (CH) and 152.9 (C) (one overlapping signal);

HPLC (90% CH$_3$CN in H$_2$O) t$_r$=2.063 (78.41%);

LCMS (APCI), m/z 445.32 ($^{81}$BrM$^+$+H, 89%), 443.31 ($^{79}$BrM$^+$+H, 100).

4-((3-((1H-1,2,4-triazol-1-yl)methyl)-5-(2-cyanopropan-2-yl)benzyl)sulfanyl)-2-bromophenyl sulfamate (TJA01179, STX1795)

C$_{20}$H$_{20}$BrN$_5$O$_3$S$_2$ MW 522.44

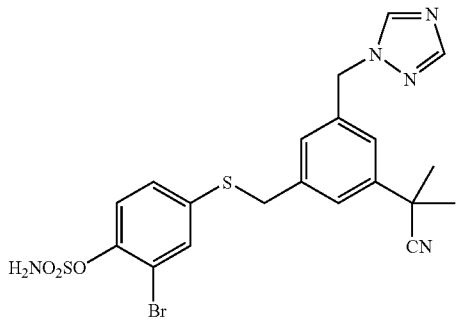

Sulfamoyl chloride in toluene (0.60 M, 1.35 mL) was transferred to an 10 mL r.b. flask and the solvent removed under vacuum at 30° C. On cooling a white solid formed to which was added N,N-dimethylacetamide (1.5 mL) to form a colourless solution. TJA01174 (0.072 g, 0.162 mmol) was added and the solution left to stir at room temperature under N$_{2\ (g)}$ for 14 h. The reaction mixture was then poured into distilled H$_2$O (30 mL) and extracted with ethyl acetate (25 mL×2). The organic layers were combined and washed with distilled H$_2$O (25 mL×4) and brine (25 mL×2). Dried over MgSO$_4$ and solvent removed in vacuo to leave off white residues. Column chromatography (dichloromethane/acetone 80:20) eluted the title compound as a white solid (0.082 g, 96%), R$_f$: 0.39 (dichloromethane/acetone 80:20).

$^1$H NMR (270 MHz, CDCl$_3$) δ 1.63 (6H, s, ArC(CH$_3$)$_2$CN), 4.06 (2H, s, ArCH$_2$SAr), 5.28 (2H, s, ArCH$_2$N), 6.54 (1H, s, ArH), 6.97-7.01 (1H, dd, J=2.2 & 8.6 Hz, ArH), 7.09 (2H, bs, ArOSO$_2$NH$_2$), 7.25-7.31 (2H, m, ArH), 7.35 (1H, s, ArH), 7.40-7.41 (1H, d, J=2.2 Hz, ArH), 7.63 (1H, s, C$_2$H$_2$N$_3$) and 7.87 (1H, s, C$_2$H$_2$N$_3$);

HPLC (70% CH$_3$CN in H$_2$O) t$_r$=2.402 (100%);

LCMS (APCI), m/z 524.27 ($^{81}$BrM$^+$+H, 100%), 522.25 ($^{79}$BrM$^+$+H, 80).

Synthesis of STX1833

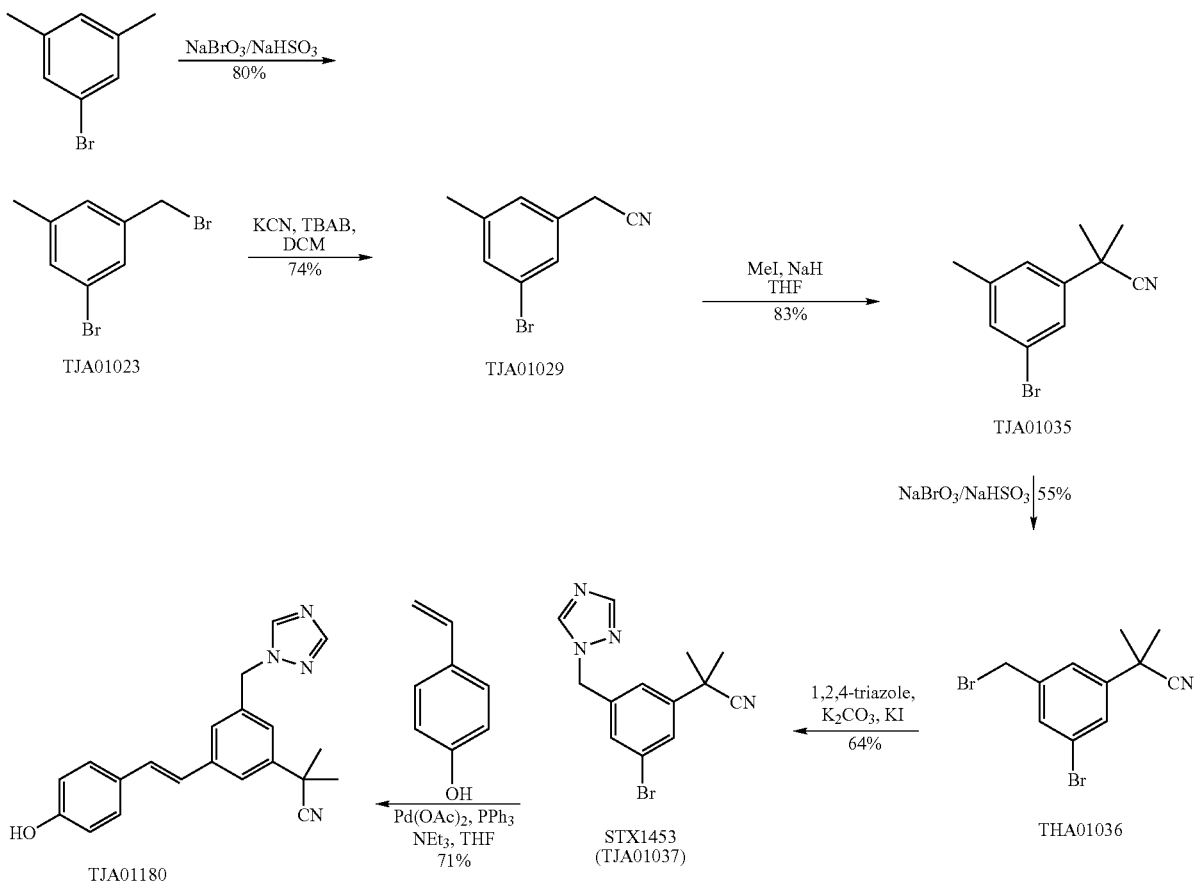

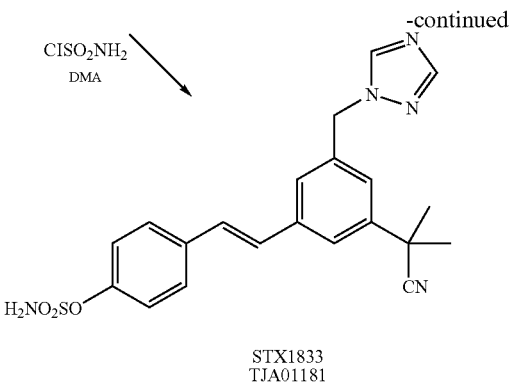

STX1833
TJA01181

1-Bromo-3-bromomethyl-5-methylbenzene (TJA01023)

C$_8$H$_8$Br$_2$ MW 263.96

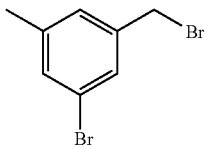

To a solution of sodium bromate (24.4 g, 162 mmol) in distilled H$_2$O (40 mL) was added 5-bromo-m-xylene (10.0 g, 54.0 mmol) in cyclohexane (108 mL). To this clear mixture a solution of sodium hydrogen sulphate (30.8 g, 162 mmol) in distilled H$_2$O (81 mL) was added drop wise with vigorous stirring over 60 min. The reaction mixture was stirred for a further 3 h at room temperature. The ethyl acetate was separated and diethyl ether (100 mL) added. This was then washed with saturated Na2SO$_{3(aq)}$ (100 mL), distilled water (100 ml×2) and brine (100 mL). Dried over Na$_2$SO$_4$ and solvent removed in vacuo to leave a clear syrup. Column chromatography (hexane) eluted the title compound as a clear oil that crystallised on standing to give a white crystalline solid that was used without further purification (8.45 g, 60%);

R$_f$ 0.52 (hexane), c.f 0.52 (dibromobenzylbromide), 0.45 (1,5-dibenzylbromide), 0.6 (5-bromo-m-xylene).

$^1$H NMR (270 MHz, CDCl$_3$) δ 2.31 (3H, s, ArCH$_3$), 4.38 (2H, s, ArCH$_2$Br), 7.11 (1H, s, ArH), 7.25 (1H, s, ArH) and 7.32 (1H, s, ArH);

HPLC (60% CH$_3$CN in H$_2$O) t$_r$=3.877 (67%), 4.644 (31%, dibromobenzylbromide).

(3-Bromo-5-methyl-phenyl)acetonitrile (TJA01029)

C$_9$H$_8$BrN MW 210.07

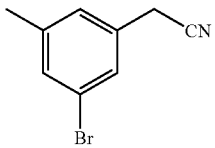

TJA01023 (11.3 g, 42.7 mmol), potassium cyanide (3.34 g, 51.2 mmol) and tetrabutylammonium bromide (0.700 g, 2.10 mmol) were loaded to an r.b. flask together with dichloromethane (60 mL) and distilled water (15 mL). With vigorous stirring the reaction mixture was set to reflux (45° C.) for 24 h. On cooling the organic fraction was separated and washed with distilled water (50 mL×2) and brine (50 mL×2) then dried over Na$_2$SO$_4$ and solvent removed in vacuo to leave a red/orange oil. Column chromatography initially eluting with hexane separated the dibromobenzylbromide impurity. Further elution with hexane/dichloromethane (50:50) gave the title compound as a clear yellow oil (6.63 g, 74%), R$_f$ 0.54 (hexane/dichloromethane 50:50)

$^1$H NMR (270 MHz, CDCl$_3$) δ 2.31 (3H, s, ArCH$_3$), 3.66 (2H, s, ArCH$_2$CN), 7.06 (1H, s, ArH), 7.25 (1H, s, ArH) and 7.27 (1H, s, ArH);

$^{13}$C NMR (100.5 MHz, CDCl$_3$) δ 21.1, 23.2, 117.4, 122.8, 127.4, 128.1, 131.7, 131.9 and 141.1;

HPLC (80% CH$_3$CN in H$_2$O) t$_r$=2.278 (72.5%);

LCMS (APCI), m/z 211.78 ($^{81}$BrM$^+$, 53%), 209.78 ($^{79}$BrM$^+$, 55), 184.83 ($^{81}$BrM$^+$–CN, 80), 182.83 ($^{79}$BrM$^+$–CN, 76).

2-(3-Bromo-5-methylphenyl)-2-methyl-propionitrile (TJA01035)

C$_{11}$H$_{12}$BrN MW 238.13

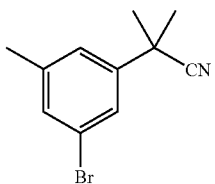

To a dry r.b. flask purged with N$_2$ $_{(g)}$ was added TJA01029 (6.00 g, 28.6 mmol) and dry THF (20 mL). With stirring this was cooled via an ice-water bath and NaH (1.71 g, 71.4 mmol) was added gradually and then left to stir at 0° C. under N$_2$ $_{(g)}$ for 15 min. Iodomethane (3.91 mL, 62.8 mmol) was then added dropwise. The resulting suspension was left to stir at room temperature for 16 h. Propan-2-ol (5 mL) was carefully added to the reaction mixture followed by dichloromethane (50 mL) and washed with distilled H$_2$O (50 mL×2) and brine (50 mL×2). Dried over Na$_2$SO$_4$ and solvent removed in vacuo to leave a red/orange oil. Column chromatography (hexane/dichloromethane 50:50) eluted the title compound as a light yellow oil (5.65 g, 83%);

$R_f$ 0.38 (hexane/dichloromethane 50:50), c.f. 0.26 (3-Bromo-5-methyl-phenyl)acetonitrile;

¹H NMR (270 MHz, CDCl₃) δ 1.68 (6H, s, ArC(CH₃)₂CN), 2.33 (3H, s, ArCH₃), 7.20 (1H, s, ArH), 7.26 (1H, s, ArH) and 7.34 (1H, s, ArH);

¹³C NMR (100.5 MHz, CDCl₃) δ 21.3 (CH₃), 29.0 (CH₃), 36.9 (C), 122.8, 124.1, 124.9, 125.2, 131.6, 140.9 and 143.4;

HPLC (80% CH₃CN in H₂O) $t_r$=2.600 (89.65%);

LCMS (APCI), m/z 239.93 (⁸¹BrM⁺, 3%), 237.93 (⁷⁹BrM⁺, 4), 212.92 (⁸¹BrM⁺-CN, 100), 210.92 (⁷⁹BrM⁺-CN, 96), 157.89 (M⁺-Br, 18).

2-(3-Bromo-5-bromomethyl-phenyl)-2-methylpropionitrile (TJA01036)

C₁₁H₁₁Br₂N MW 317.03

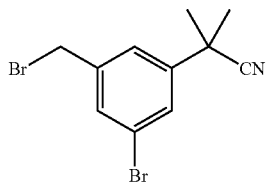

To a solution of sodium bromate (9.51 g, 63.0 mmol) in distilled H₂O (32 mL) was added TJA01035 (5.00 g, 21.0 mmol) in cyclohexane (42 mL). To this clear mixture a solution of sodium hydrogen sulphate (7.56 g, 63.0 mmol) in distilled H₂O (63 mL) was added drop wise with vigorous stirring over 1 h. The reaction mixture was stirred for a further 4 h at room temperature. The cyclohexane was separated and diethyl ether (100 mL) added. This was then washed with saturated Na2SO₃₍aq₎ (50 mL), distilled water (50 ml×2) and brine (50 mL×2). Dried over Na₂SO₄ and solvent removed in vacuo to leave viscous orange oil. Column chromatography (hexane/dichloromethane 50:50) eluted starting material and the title compound as a clear viscous oil (3.64 g, 54%), $R_f$ 0.55 (hexane/dichloromethane 50:50), c.f. 0.38 (2-(3-bromo-5-methylphenyl)-2-methyl-propionitrile);

¹H NMR (270 MHz, CDCl₃) δ 1.71 (6H, s, ArC(CH₃)₂CN), 4.41 (2H, s, ArCH₂Br), 7.40-7.41 (1H, t, J=1.7, ArH) and 7.48-7.51 (2H, m, ArH); HPLC (80% CH₃CN in H₂O) $t_r$=2.508 (83.05%);

LRMS (FAB⁺), m/z 319.1 (⁸¹BrM⁺, 100%), 317.1 (⁷⁹BrM⁺, 100).

2-(3-Bromo-5-[1,2,4-triazole-1-yl-methylphenyl)-2-methylpropionitrile (TJA01038, STX1453)

C₁₃H₁₃BrN₄ MW 305.18

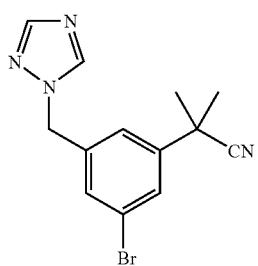

TJA01036 (3.20 g, 10.1 mmol), 1,2,4-triazole (1.05 g, 15.2 mmol), potassium carbonate (1.40 g, 10.1 mmol), potassium iodide (0.10 g, 0.600 mmol) and acetone (150 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2), 1M NaOH (50 mL×1) and brine (50 mL×2). Dried over Na₂SO₄ and solvent removed in vacuo to leave a yellow oil. Column chromatography (ethyl acetate) eluted the title compound as a clear viscous oil that crystallised on standing to give a colourless crystalline solid (1.97 g, 64%), mp 70.9-71.8° C.;

$R_f$ 0.24 (ethyl acetate).

¹H NMR (270 MHz, CDCl₃) δ 1.68 (6H, s, ArC(CH₃)₂CN), 5.33 (2H, s, ArCH₂N), 7.40-7.41 (2H, t, J=1.7, ArH), 7.54-7.55 (1H, t, J=1.7, ArH), 7.99 (1H, s, C₂H₂N₃) and 8.12 (1H, s, C₂H₂N₃);

¹³C NMR (100.5 MHz, CDCl₃) δ 29.0 (CH₃), 37.0 (C), 52.6 (CH₂), 123.5, 123.7, 128.6, 130.4, 137.7, 143.4, 144.5 and 152.6 (one overlapping peak);

HPLC (60% CH₃CN in H₂O increasing to 95% over 10 min) $t_r$=2.293 (98.87%); MS (EI), m/z 307.09 (⁸¹BrM⁺, 100%), 305.09 (⁷⁹BrM⁺, 99), 238.01 ((⁸¹BrM-(C₂H₂N₃)⁺, 22), 236.01 ((⁷⁹BrM-(C₂H₂N₃)⁺, 24).

2-(3-((1H-1,2,4-triazol-1-yl)methyl)-5-(4-hydroxystyryl)phenyl)-2-methylpropanenitrile (TJA01180)

C₂₁H₂₀N₄O MW 344.41

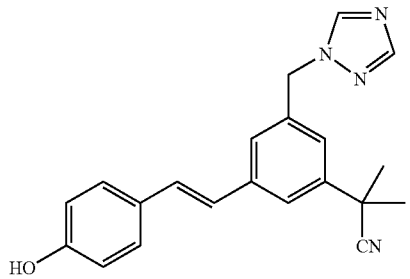

TJA01037 (0.100 g, 0.328 mmol), 4-vinylphenol [10% wt in propylene glycol] (0.787 g, 0.655 mmol), triethylamine (91.0 μL, 0.655 mmol) and triphenylphosphine (0.029 g, 0.112 mmol) were loaded to a dry 10 mL r.b. flask purged with N₂ ₍g₎. Anhydrous THF (1.5 mL) was added via a syringe and the resulting clear solution degassed via bubbling N₂ ₍g₎ for 30 min. Pd (OAc)₂ (0.012 g, 0.056 mmol) was added, a condenser attached and the reaction mixture heated to 85° C. for 22 h with constant stirring (4-vinylphenol (0.394 g, 0.328 mmol) added after 6 h). After the reaction had been allowed to cool THF was removed in vacuo and the residues dissolved in dichloromethane (20 mL), washed with 2M KHSO₄ ₍aq₎ (20 mL), distilled H₂O (20 mL×3) and brine (20 mL). The organic portion was dried over MgSO₄ and solvent removed in vacuo. Column chromatography (ethyl acetate) eluted a colourless viscous oil (0.080 g, 71%) which was used without further purification.

4-(3-((1H-1,2,4-triazol-1-yl)methyl)-5-(2-cyanopropan-2-yl)styryl)phenyl sulfamate (TJA01181, STX1833)

$C_{21}H_{21}N_5O_3S$ MW 423.49

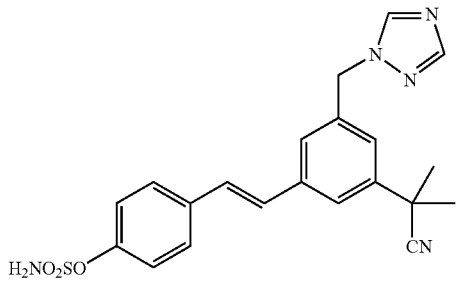

Sulfamoyl chloride in toluene (0.60 M, 1.93 mL) was transferred to a 10 mL r.b. flask and the solvent removed under vacuum at 30° C. On cooling a white solid formed to which was added N,N-dimethylacetamide (1.5 mL) to form a colourless solution. TJA01180 (0.080 g, 0.232 mmol) was added and the solution left to stir at room temperature under $N_{2\ (g)}$ for 60 h. The reaction mixture was then poured into distilled $H_2O$ (25 mL) and extracted with ethyl acetate (25 mL×2). The organic layers were combined and washed with distilled $H_2O$ (25 mL×4) and brine (25 mL). Dried over $MgSO_4$ and solvent removed in vacuo to leave off white residues. Column chromatography (dichloromethane/acetone 80:20) eluted the title compound as a white solid (0.035 g, 36%), mp 151.4-152.1° C.;

$R_f$: 0.30 (dichloromethane/acetone 75:25);

$^1H$ NMR (600 MHz, DMSO-$d_6$) δ 1.73 (6H, s, ArC($CH_3$)$_2$)CN), 5.50 (2H, s, ArCH$_2$N), 7.30-7.33 (3H, m, ArH & vinyl), 7.35-7.38 (1H, d, J=16.6 Hz, trans vinyl), 7.31-7.33, 7.42 (1H, s, ArH), 7.51 (1H, s, ArH), 7.71 (1H, s, ArH), 7.72-7.74 (2H, d, J=8.4 Hz, AA'BB'), 8.04 (1H, s, $C_2H_2N_3$), 8.06 (2H, bs, ArOSO$_2$NH$_2$) and 8.73 (1H, s, $C_2H_2N_3$);

HPLC (90% CH$_3$CN in H$_2$O) $t_r$=1.784 (99.10%);

LCMS (APCI), m/z 424.42 (M$^+$+H, 100%), 345.47 ((M$^+$+H)—OSO$_2$NH$_2$, 27).

Biological Data

A number of compounds (including anastrozole, STX1022 and STX1023, the structures of which are shown below) were tested for aromatase and steroid sulphatase inhibition in accordance with the above Protocols.

In vivo data were recorded using the above described aromatase and STS animals assays. The relevant compounds were administered and for each animal both aromatase and STS activities were determined.

| STX CODE | STRUCTURE | % AROMATASE INHIBITION (10 μM) | % STS INHIBITION (10 μM) |
|---|---|---|---|
| STX1522 | 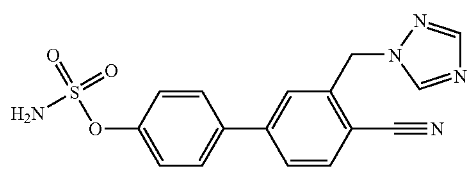 | 98.0 ± 0.3% | 96.1 ± 0.3% |
| STX1523 | 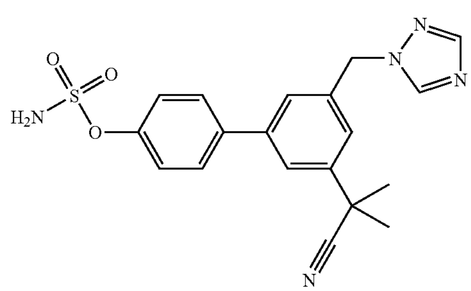 | 99.7 ± 0.2% | 24.4 ± 3.1% |
| STX1528 | 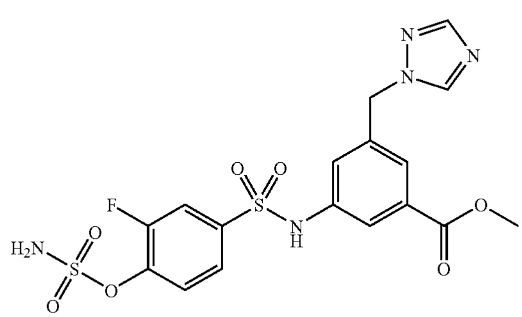 | 83.4 ± 1.3% | <10% |

-continued
| STX CODE | STRUCTURE | % AROMATASE INHIBITION (10 μM) | % STS INHIBITION (10 μM) |
|---|---|---|---|
| STX1729 | 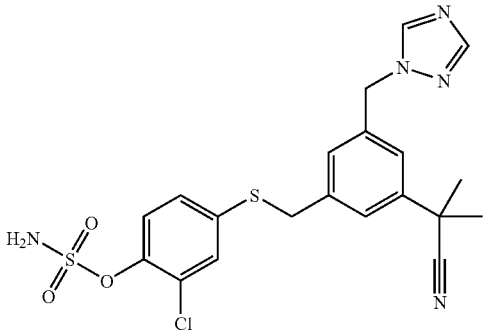 | 99.9 ± 0.2% | 82.3 ± 0.8% |
| STX1731 | 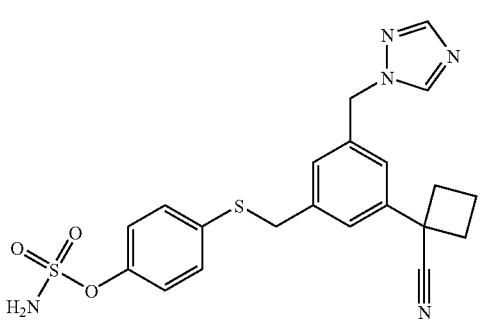 | 99.5 ± 0.2% | 21.4 ± 7.9% |
| STX1732 | 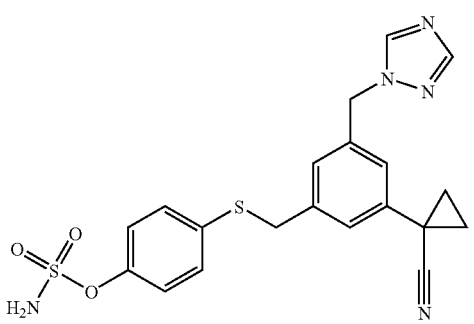 | 99.8 ± 0.1% | <10% |
| STX1761 | 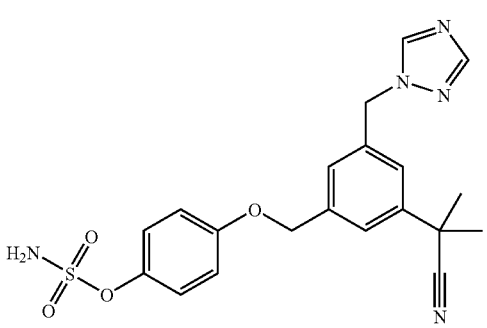 | 99.8 ± 0.2% | <10% |

| STX CODE | STRUCTURE | % AROMATASE INHIBITION (10 μM) | % STS INHIBITION (10 μM) |
|---|---|---|---|
| STX1794 | 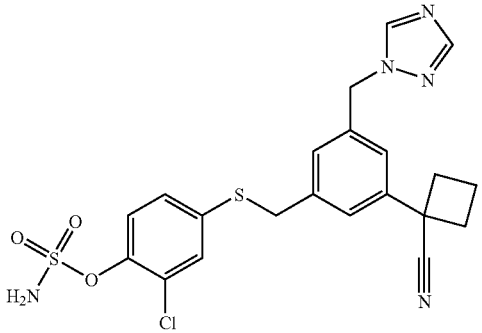 | 99.7 ± 0.1% | 75.3 ± 0.6% |
| STX1795 | 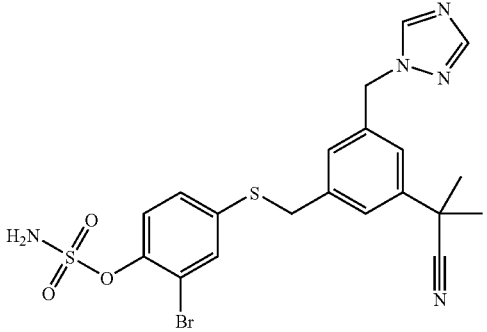 | 100 ± 0.0% | 73.6 ± 0.1% |
| STX1829 | 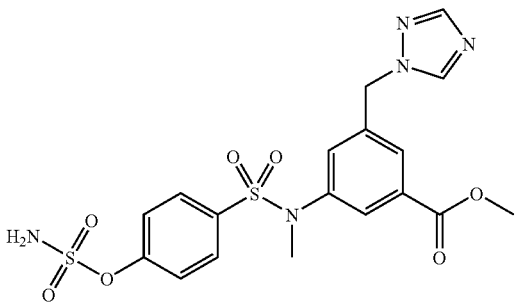 | 99.5 ± 0.2% | 17.6 ± 4.0% |
| STX1830 | 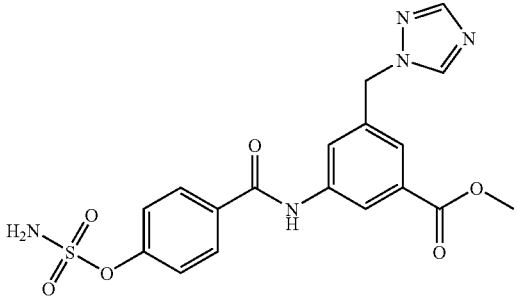 | 52.7 ± 6.7% | 33.4 ± 5.3% |

-continued

| STX CODE | STRUCTURE | % AROMATASE INHIBITION (10 μM) | % STS INHIBITION (10 μM) |
|---|---|---|---|
| STX1833 | 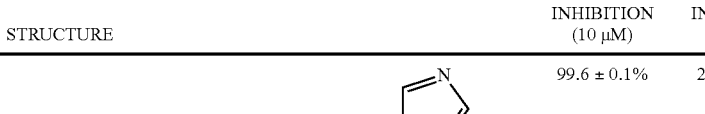 | 99.6 ± 0.1% | 21.5 ± 4.7% |

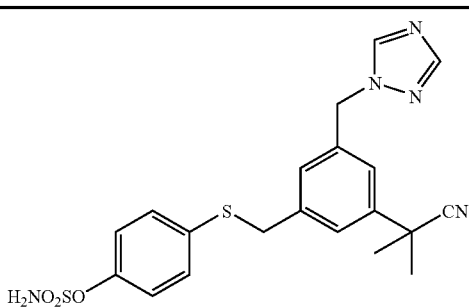
STX1023

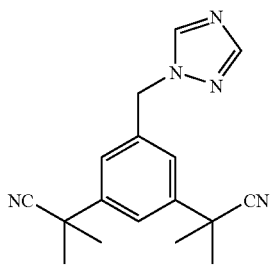
Anastrozole

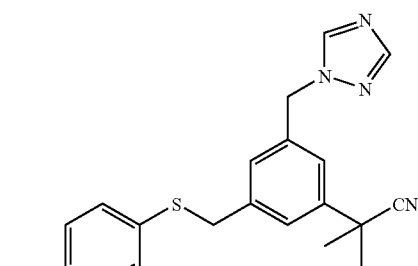
STX1022

| Compound | JEG3 cells IC50 (nM) | | In vivo % Inhibition (10 mg/kg) | |
|---|---|---|---|---|
| | Aromatase | STS | Aromatase (after 3 h) | STS |
| STX1023 | 3.5 | >10,000 | ND | 87 |
| Anastrozole | 1.5 | ND | ND | ND |
| STX1022 | 1 | — | — | — |

The invention will now be further described by the following numbered paragraphs:

1. A compound of Formula I

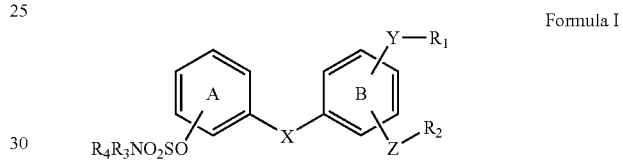

Formula I wherein

X, Y and Z are each independently of each other an optional linker group;

$R_1$ is a ring system;

$R_2$ is selected from hydrocarbyl groups, oxyhydrocarbyl groups, cyano (—CN), nitro (—NO$_2$) and halogens;

$R_3$ and $R_4$ are independently selected from H and hydrocarbyl ring A and B are independently optionally further substituted.

2. A compound according to paragraph 1 of Formula II

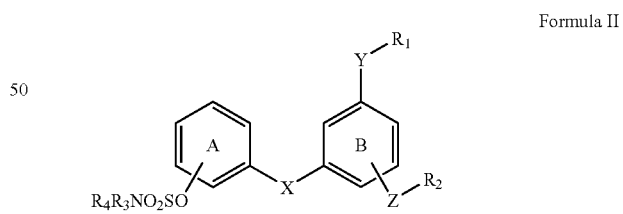

Formula II

3. A compound according to paragraph 1 of Formula III

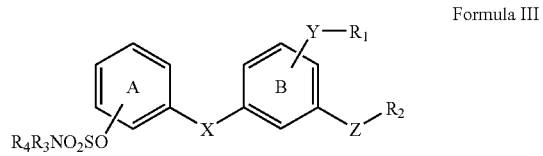

Formula III

4. A compound according to paragraph 1 of Formula IV

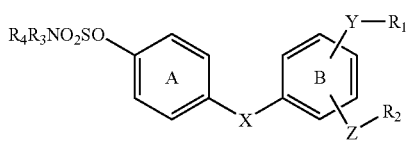
Formula IV

5. A compound according to paragraph 1 of Formula V

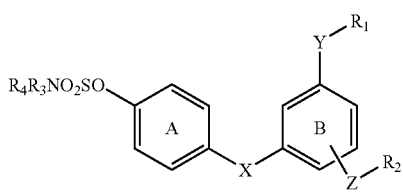
Formula V

6. A compound according to paragraph 1 of Formula VI

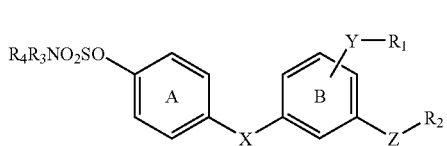
Formula VI

7. A compound according to paragraph 1 of Formula VII

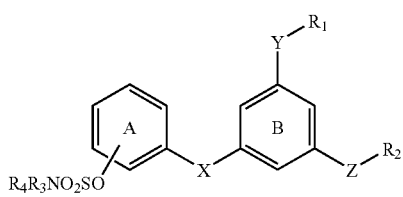
Formula VII

8. A compound according to paragraph 1 of Formula VIII or Formula VIIIa

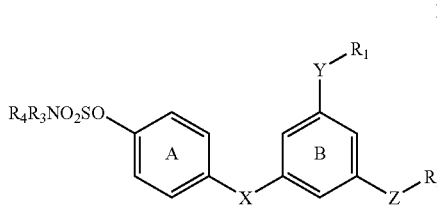
Formula VIII

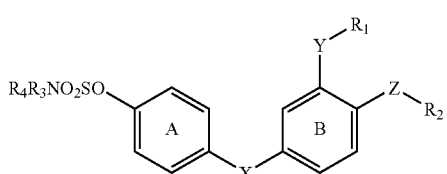
Formula VIIIa

9. A compound according to paragraph 1 of Formula VIII

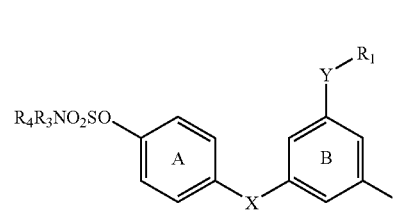
Formula VIII

10. A compound according to any one of the preceding paragraphs wherein at least one of the optional linker groups is present.

11. A compound according to any one of the preceding paragraphs wherein at least two of the optional linker groups are present.

12. A compound according to any one of the preceding paragraphs wherein each of X, Y and Z are present.

13. A compound according to any one of the preceding paragraphs wherein X is selected from hydrocarbyl, oxyhydrocarbyl, COO, CO, S, O, SO, $SO_2$, NR, and $SO_2NR$, wherein R is selected from H and hydrocarbyl groups.

14. A compound according to paragraph 13 wherein the hydrocarbyl group is a straight of branched alkyl group.

15. A compound according to paragraph 13 wherein the hydrocarbyl group is a straight chain alkyl group.

16. A compound according to paragraph 13 wherein the oxyhydrocarbyl group is —O-alkyl-, wherein alkyl is a straight of branched alkyl group.

17. A compound according to paragraph 13 wherein the oxyhydrocarbyl group is —O-alkyl-, wherein alkyl is a straight chain alkyl group 18. A compound according to any one of the preceding paragraphs wherein X is selected from $(CH_2)n$, CH=CH (preferably trans configuration), $O(CH_2)n$, $(CH_2)nO$, $S(CH_2)n$, $(CH_2)nS$, $CO(CH_2)n$, $(CH_2)nCO$, $CONH(CH_2)n$, $(CH_2)nCONH$, $COO(CH_2)n$, $(CH_2)nCOO$, $SO(CH_2)n$, $(CH_2)nSO$, $SO_2(CH_2)n$, $(CH_2)nSO_2$, $SO_2NMe(CH_2)n$, $(CH_2)nSO_2NMe$; $SO_2NH(CH_2)n$, and $(CH_2)nSO_2NH$; wherein n is independently an integer from 0 to 6.

19. A compound according to paragraph 18 wherein n is independently an integer from 1 to 6.

20. A compound according to any one of the preceding paragraphs wherein X is selected from $SO_2NH$, $SO_2NMe$, CONH, $OCH_2$, $SCH_2$, and CH=CH.

21. A compound according to any one of the preceding paragraphs wherein Y is selected from hydrocarbyl, oxyhydrocarbyl, COO, CO, S, O, SO, $SO_2$, NR, and $SO_2NR$, wherein R is selected from H and hydrocarbyl groups.

22. A compound according to any one of the preceding paragraphs wherein Y is selected from hydrocarbyl, CO, and $SO_2$.

23. A compound according to paragraph 21 or 22 wherein the hydrocarbyl group is a straight of branched alkyl group.

24. A compound according to paragraph 21 or 22 wherein the hydrocarbyl group is a straight chain alkyl group.

25. A compound according to any one of the preceding paragraphs wherein Y is selected is from groups selected from $(CH_2)m$, $CO(CH_2)m$, $(CH_2)mCO$, $SO_2(CH_2)m$ and wherein m is independently an integer from 0 to 6.

26. A compound according to paragraph 25 wherein m is independently an integer from 1 to 6.

27. A compound according to any one of the preceding paragraphs wherein Y is (CH$_2$)m, wherein m is an integer from 1 to 6.

28. A compound according to paragraph 27 wherein Y is —CH$_2$—.

29. A compound according to any one of the preceding paragraphs wherein Z is selected from hydrocarbyl, oxyhydrocarbyl, COO, CO, S, O, SO, SO$_2$, NR, and SO$_2$NR, wherein R is selected from H and hydrocarbyl groups.

30. A compound according to any one of the preceding paragraphs wherein Z is a hydrocarbyl group.

31. A compound according to paragraph 30 wherein the hydrocarbyl group is a straight of branched alkyl group.

32. A compound according to paragraph 30 wherein the hydrocarbyl group is a branched alkyl group.

33. A compound according to any one of the preceding paragraphs wherein Z is C$_p$H$_2$p, wherein p is an integer from 1 to 6.

34. A compound according to paragraph 33 wherein p is independently an integer from 1 to 3.

35. A compound according to any one of the preceding paragraphs wherein Z is selected from —C(CH$_3$)$_2$—, —C(O)O—,

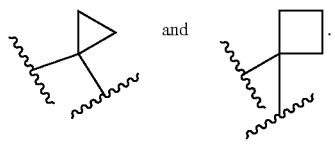

and

36. A compound according to any one of the preceding paragraphs wherein R$_1$ is or comprises an aromatic ring.

37. A compound according to any one of the preceding paragraphs wherein R$_1$ is selected from substituted and unsubstituted aromatic rings.

38. A compound according to any one of the preceding paragraphs wherein R$_1$ is selected from ring systems comprising from 3 to 10 members.

39. A compound according to any one of the preceding paragraphs wherein R$_1$ is selected from ring systems comprising from 5, 6 or 7 members.

40. A compound according to any one of the preceding paragraphs wherein R$_1$ is selected from ring systems comprising carbon and optionally one or more hetero atoms.

41. A compound according to any one of the preceding paragraphs wherein R$_1$ is selected from ring systems comprising carbon and optionally one, two or three hetero atoms.

42. A compound according to any one of the preceding paragraphs wherein R$_1$ is selected from ring systems comprising carbon and one or more hetero atoms.

43. A compound according to any one of the preceding paragraphs wherein R$_1$ is selected from ring systems comprising carbon and one or more hetero atoms selected from Nitrogen, Sulphur and Oxygen.

44. A compound according to any one of the preceding paragraphs wherein R$_1$ is selected from heterocyclic ring systems, wherein the ring comprises carbon and nitrogen.

45. A compound according to any one of the preceding paragraphs wherein R$_1$ is selected from 4H-1,2,4-triazole, 1H-1,2,4-triazole and 1H-1,2,3-triazole.

46. A compound according to any one of the preceding paragraphs wherein R$_1$ is 1H-1,2,4-triazole.

47. A compound according to any one of the preceding paragraphs wherein R$_1$ is

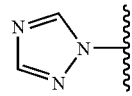

48. A compound according to any one of the preceding paragraphs wherein R$_2$ is selected from hydrocarbyl groups, oxyhydrocarbyl groups, cyano (—CN), nitro (—NO$_2$) and halogens, wherein the hydrocarbyl group is a straight of branched alkyl group.

49. A compound according to paragraph 48 wherein the hydrocarbyl group is a straight chain alkyl group.

50. A compound according to paragraph 48 wherein the hydrocarbyl group is (CH$_2$)qCH$_3$, wherein q is an integer from 0 to 6.

51. A compound according to any one of the preceding paragraphs wherein R$_2$ is selected from hydrocarbyl groups, oxyhydrocarbyl groups, cyano (—CN), nitro (—NO$_2$) and halogens, wherein the oxyhydrocarbyl group is —O-alkyl-, wherein alkyl is a straight or branched alkyl group.

52. A compound according to paragraph 51 wherein the oxyhydrocarbyl group is —O-alkyl-, wherein alkyl is a straight chain alkyl group 53. A compound according to paragraph 52 wherein the oxyhydrocarbyl group is —O(CH$_2$)rCH$_3$, wherein r is an integer from 0 to 6.

54. A compound according to any one of the preceding paragraphs wherein R$_2$ is selected from —CH$_3$, —OCH$_3$, cyano (—CN), nitro (—NO$_2$) and halogens.

55. A compound according to any one of the preceding paragraphs wherein R$_3$ and R$_4$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

56. A compound according to any one of the preceding paragraphs wherein at least one of R$_3$ and R$_4$ is H.

57. A compound according to any one of the preceding paragraphs wherein R$_3$ is H and R$_4$ is H.

58. A compound according to any one of the preceding paragraphs wherein rings A and B are independently not further substituted.

59. A compound according to any one of the preceding paragraphs wherein neither ring A nor ring B is further substituted.

60. A compound according to any one paragraphs 1 to 57 wherein rings A and B are independently further substituted by groups selected from hydrocarbyl groups, oxyhydrocarbyl groups, cyano (—CN), nitro (—NO$_2$) and halogens.

61. A compound according to any one paragraphs 1 to 57 wherein rings A and B are independently further substituted by groups selected from C1-6 alkyl groups, C1-6 alkoxy groups, cyano (—CN), nitro (—NO$_2$) and halogens.

62. A compound according to any one paragraphs 1 to 57 wherein rings A and B are independently further substituted by groups selected from —CH$_3$, —CH$_2$CH$_3$, —OCH$_3$, cyano (—CN), nitro (—NO$_2$) and halogens.

63. A compound according to paragraph 1 selected from compounds of the formulae

137
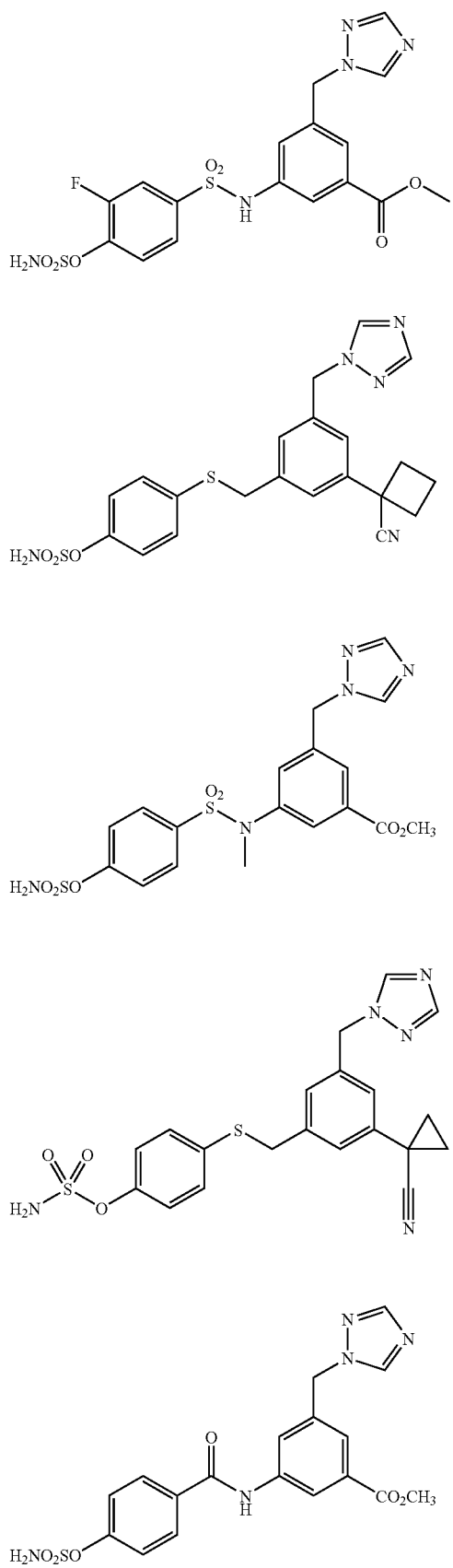
138
-continued
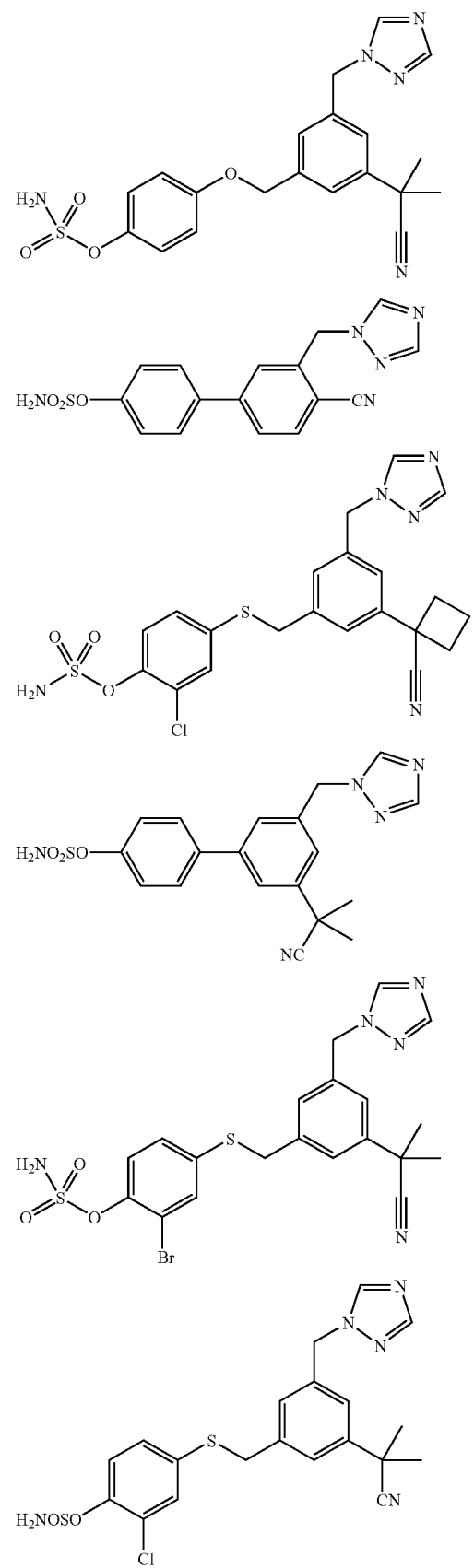

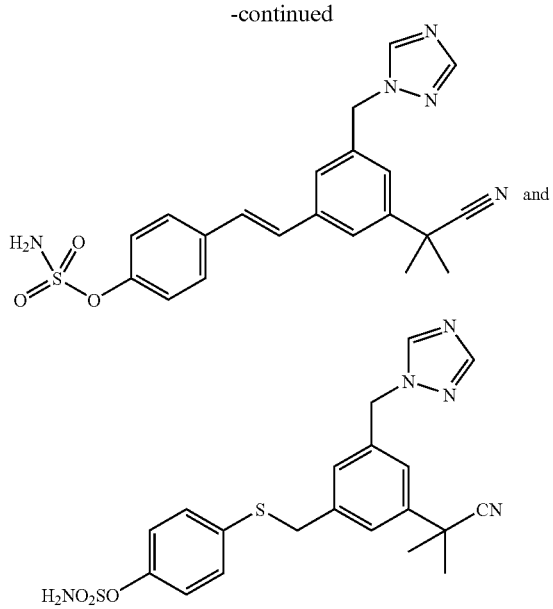

64. A compound according to any one of paragraphs 1 to 63 for use in medicine.

65. A pharmaceutical composition comprising the compound according to any one of paragraphs 1 to 63 optionally admixed with a pharmaceutically acceptable carrier, diluent, excipient or adjuvant.

66. Use of a compound according to any one of paragraphs 1 to 63 in the manufacture of a medicament for use in the therapy of a condition or disease associated with STS and/or aromatase and/or cell cycling and/or apoptosis and/or cell growth.

67. Use of a compound according to any one of paragraphs 1 to 63 in the manufacture of a medicament for use in the therapy of a condition or disease associated with STS and aromatase.

68. Use of a compound according to any one of paragraphs 1 to 63 in the manufacture of a medicament for use in the therapy of a condition or disease associated with adverse STS levels and/or adverse aromatase levels and/or cell cycling and/or apoptosis and/or cell growth.

69. Use of a compound according to any one of paragraphs 1 to 63 in the manufacture of a medicament for use in the therapy of a condition or disease associated with adverse STS levels and adverse aromatase levels.

70. Use of a compound according to any one of paragraphs 1 to 63 in the manufacture of a medicament for inhibiting STS activity and/or inhibiting aromatase activity.

71. Use of a compound according to any one of paragraphs 1 to 63 in the manufacture of a medicament for inhibiting STS activity and inhibiting aromatase activity.

72. A compound as substantially hereinbefore described with reference to the Examples.

73. A composition as substantially hereinbefore described with reference to the Examples.

74. A method or use as substantially hereinbefore described with reference to the Examples.

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A compound of Formula I

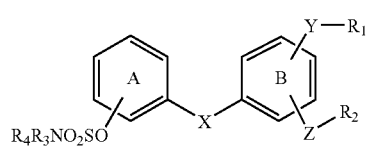

Formula I wherein
X and Z are each independently of each other an optional linker group selected from an alkyl group, an alkenyl group, an alkynl group, an aryl group, an alkoxy group, and oxyalkenyl group, an oxyalkynyl group, and oxyaryl group, COO, CO, S, o, SO, $SO_2$, NR, and $SO_2$NR, wherein R is selected from H, an alkyl group, an alkenyl group, an alkynyl group, an aryl group;

Y is a linker group selected from an alkyl group, an alkenyl group, an alkynl group, and CO;

$R_1$ is an optionally substituted 5- or 6-membered heterocyclic group containing 1 to 3 hetero atoms each selected from N, O and S;

$R_2$ is selected from any one of an alkyl group, an alkenyl group, an alkynyl group, an aryl group, cyano (—CN), nitro (—$NO_2$) and halogens;

$R_3$ and $R_4$ are independently selected from H and an alkyl group, an alkenyl group, an alkynyl group, or an aryl group;

ring A and B are independently optionally further substituted by groups selected from —$CH_3$, —$CH_2CH_3$, —$OCH_3$, cyano (—CN), nitro (—$NO_2$) and halogens.

2. A compound according to claim 1 of Formula II

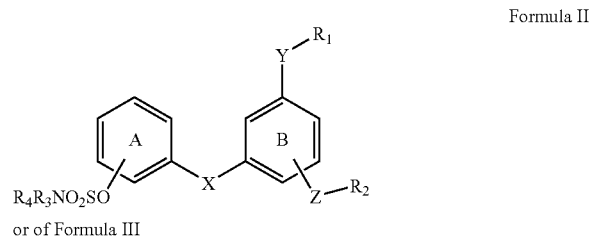

Formula II or of Formula III

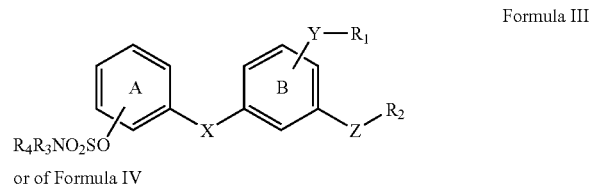

Formula III or of Formula IV

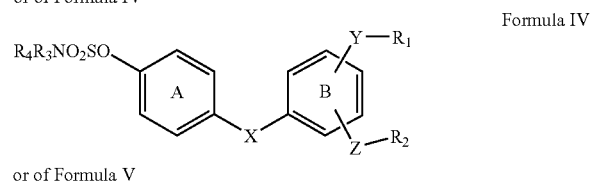

Formula IV or of Formula V

-continued

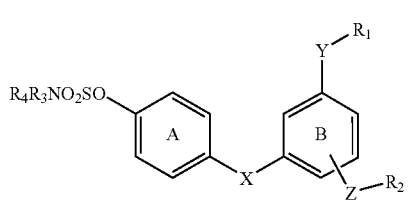

or of Formula VI

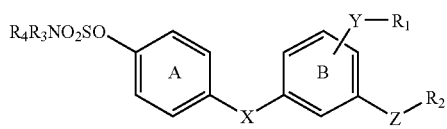

or of Formula VII

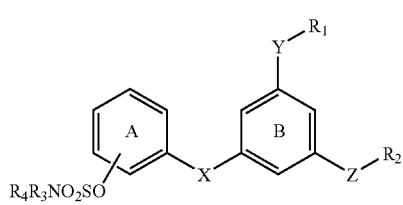

or of Formula VIII or Formula VIIIa

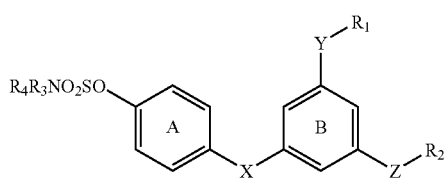

or of Formula VIII

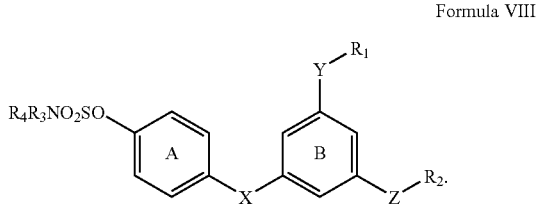

3. A compound according to claim 1 wherein at least one of the optional linker groups is present.

4. A compound according to claim 1 wherein each of X and Z are present.

5. A compound according to claim 1 wherein X is selected from an alkyl group, an alkenyl group, and alkynyl group, an aryl group, an alkoxy group, an oxyalkenyl group, an oxyalkynyl group, an oxyaryl group, COO, CO, S, O, SO, SO2, NR, and SO$_2$NR, wherein R is selected from H, an alkyl group, an alkenyl group, an alkynyl group, and an aryl group.

6. A compound according to claim 5 wherein the alkyl group is a straight or branched alkyl group.

7. A compound according to claim 5 wherein the alkyl group is a straight chain alkyl group.

8. A compound according to claim 5 wherein the alkoxy group is —O-alkyl-, wherein alkyl is a straight or branched alkyl group.

9. A compound according to claim 5 wherein the alkoxy group is —O-alkyl-, wherein alkyl is a straight chain alkyl group.

10. A compound of Formula I

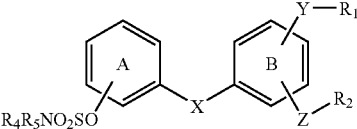

wherein

X is an optical linker group selected from (CH$_2$)n, CH=CH, O(CH$_2$)n, (CH$_2$)nO, S(CH$_2$)n, (CH$_2$)nS, CO(CH$_2$)n, (CH$_2$)nCO, CONH(CH$_2$)n, (CH$_2$)nCONH, COO(CH$_2$)n, (CH$_2$)nCOO, SO(CH$_2$)n, (CH$_2$)nSO, SO$_2$(CH$_2$)n, (CH$_2$)nSO$_2$, SO$_2$NMe(CH$_2$)n, (CH$_2$)nSO$_2$NMe; SO$_2$NH(CH$_2$)n, and (CH$_2$)nSO$_2$NH; wherein n is independently an integer from 0 to 6;

Z is an optional linker group selected from an alkyl group, an alkenyl group, an alkynl group, an aryl group, an alkoxy group, and oxyalkenyl group, an oxyalkynyl group, and oxyaryl group, COO, CO, S, O, SO, SO$_2$, NR, and SO$_2$NR, wherein R is selected from H, an alkyl group, an alkenyl group, an alkynyl group, an aryl group;

Y is a linker group selected from an alkyl group, an alkenyl group, an alkynl group, and CO;

R$_1$ is an optionally substituted 5- or 6-membered heterocyclic group containing 1 to 3 hetero atoms each selected from N, O and S;

R$_2$ is selected from any one of an alkyl group, an alkenyl group, an alkynyl group, an aryl group, cyano (-CN), nitro (-NO$_2$) and halogens;

R$_3$ and R$_4$ are independently selected from H and an alkyl group, an alkenyl group, an alkynyl group, or an aryl group;

ring A and B are independently optionally further substituted by groups selected from -CH$_3$, -CH$_2$CH$_3$, -OCH$_3$, cyano (-CN), nitro (-NO$_2$) and halogens.

11. A compound according to claim 10 wherein n is independently an integer from 1 to 6.

12. A compound according to claim 1 wherein X is selected from SO$_2$NH, SO$_2$NMe, CONH, OCH$_2$, SCH$_2$, and CH=CH.

13. A compound according to claim 1 wherein Y is selected from an alkyl group, an alkenyl group and an alkynyl group.

14. A compound according to claim 13 wherein the alkyl group is a straight or branched alkyl group.

15. A compound according to claim 13 wherein the alkyl group is a straight chain alkyl group.

16. A compound according to claim 1 wherein Y is (CH$_2$)m, wherein m is an integer from 1 to 6.

17. A compound according to claim 16 wherein Y is —CH$_2$—.

18. A compound according to claim 1 wherein Z is selected from an alkyl group, an alkenyl group, an alkynyl group, an aryl group, an alkoxy group, an oxyalkenyl group, an oxyalkynyl group, an oxyaryl group, COO, CO, S, o, SO, SO$_2$, NR and SO$_2$NR, wherein R is selected from H, an alkyl group, an alkenyl group, an alkynyl group, and an aryl group.

19. A compound according to claim 1 wherein Z is a group selected from an alkyl group, an alkenyl group, an alkynyl group, or an aryl group.

20. A compound according to claim 19 wherein the alkyl group is a straight or branched alkyl group.

21. A compound according to claim 19 wherein the alkyl group is a branched alkyl group.

22. A compound according to claim 1 wherein Z is $C_pH_{2p}$, wherein p is an integer from 1 to 6.

23. A compound according to claim 22 wherein p is independently an integer from 1 to 3.

24. A compound according to claim 1 wherein Z is selected from —C(CH$_3$)$_2$—, —C(O)O—,

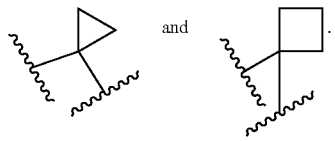

and

25. A compound according to claim 1 wherein R$_1$ is an aromatic ring.

26. A compound according to claim 1 wherein R$_1$ is selected from substituted and unsubstituted aromatic rings.

27. A compound according to claim 1 wherein R$_1$ is selected from the group consisting of imidazole, tetrazole, pyrazole, triazole, pyridazine, pyrimidine and triazine.

28. A compound according to claim 1 wherein R$_1$ is selected from 4H-1,2,4-triazole, 1H-1,2,4-triazole and 1H-1,2,3-triazole.

29. A compound according to claim 1 wherein R$_1$ is 1H-1,2,4-triazole.

30. A compound according to claim 1 wherein R$_1$ is

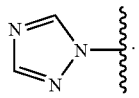

31. A compound according to claim 1 wherein R$_2$ is selected from alkyl group, an alkenyl group, an alkynyl group, an aryl group, an alkoxy group, an oxyalkenyl group, an oxyalkynyl group, an oxyaryl group, cyano (—CN), nitro (—NO$_2$) and halogens, wherein the alkyl group is a straight or branched alkyl group.

32. A compound according to claim 31 wherein the alkyl group is a straight chain alkyl group.

33. A compound according to claim 31 wherein the alkyl group is (CH$_2$)$_q$CH$_3$, wherein q is an integer from 0 to 6.

34. A compound according to claim 1 wherein R$_2$ is selected from an alkyl group, an alkenyl group, an alkynyl group, an aryl group, an alkoxy group, an oxyalkenyl group, an oxyalkynyl group, an oxyaryl group, cyano (—CN), nitro (—NO$_2$) and halogens, wherein the alkoxy group is —O-alkyl-, wherein alkyl is a straight or branched alkyl group.

35. A compound according to claim 34 wherein the alkoxy group is —O-alkyl-, wherein alkyl is a straight chain alkyl group.

36. A compound according to claim 35 wherein the alkoxy group is —O(CH$_2$)$_r$CH$_3$, wherein r is an integer from 0 to 6.

37. A compound according to claim 1 wherein R$_2$ is selected from —CH$_3$, —OCH$_3$, cyano (—CN), nitro (—NO$_2$) and halogens.

38. A compound according to claim 1 wherein R$_3$ and R$_4$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

39. A compound according to claim 1 wherein at least one of R$_3$ and R$_4$ is H.

40. A compound according to claim 1 wherein R$_3$ is H and R$_4$ is H.

41. A compound according to claim 1 wherein rings A and B are independently not further substituted.

42. A compound according to claim 1 wherein neither ring A nor ring B is further substituted.

43. A compound selected from compounds of the formulae

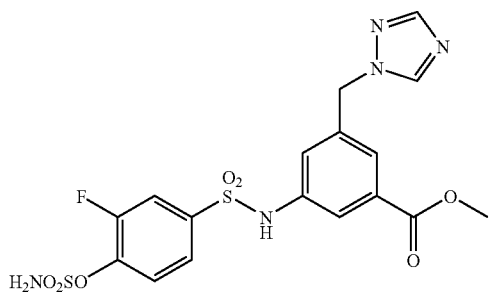

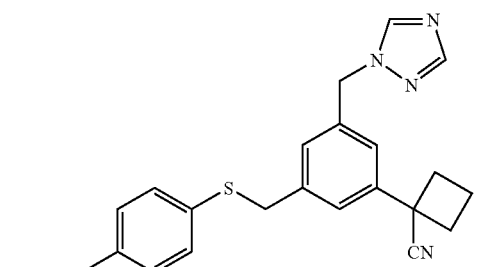

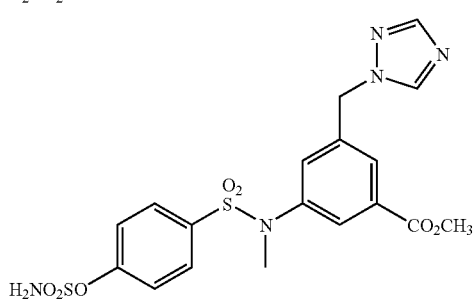

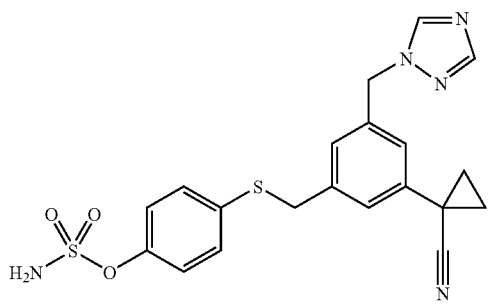

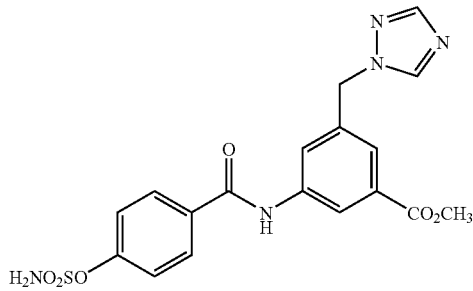

-continued
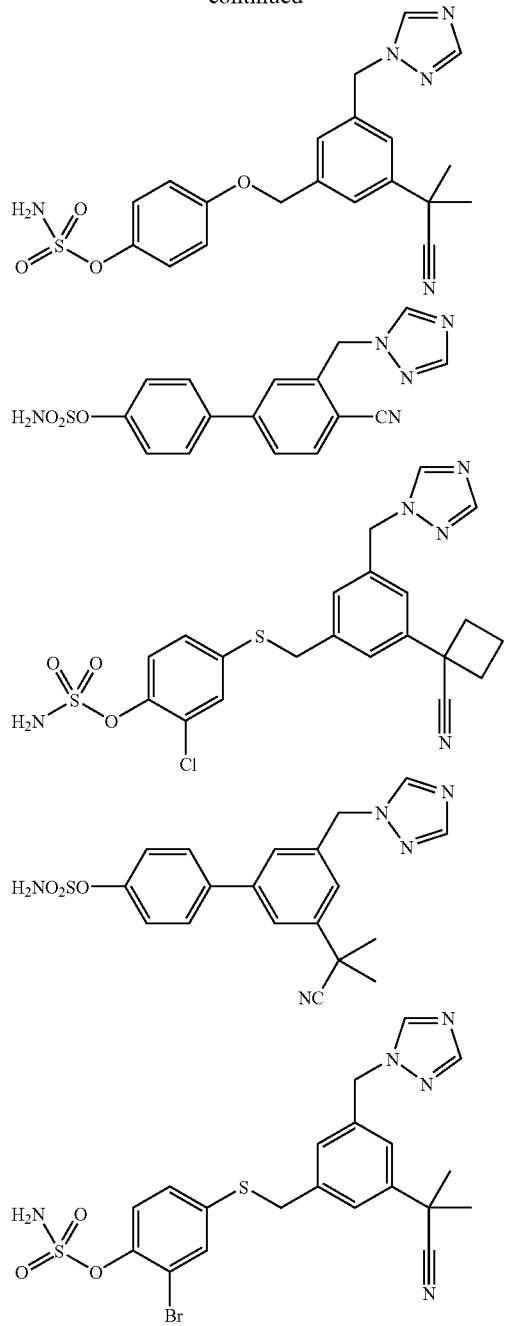
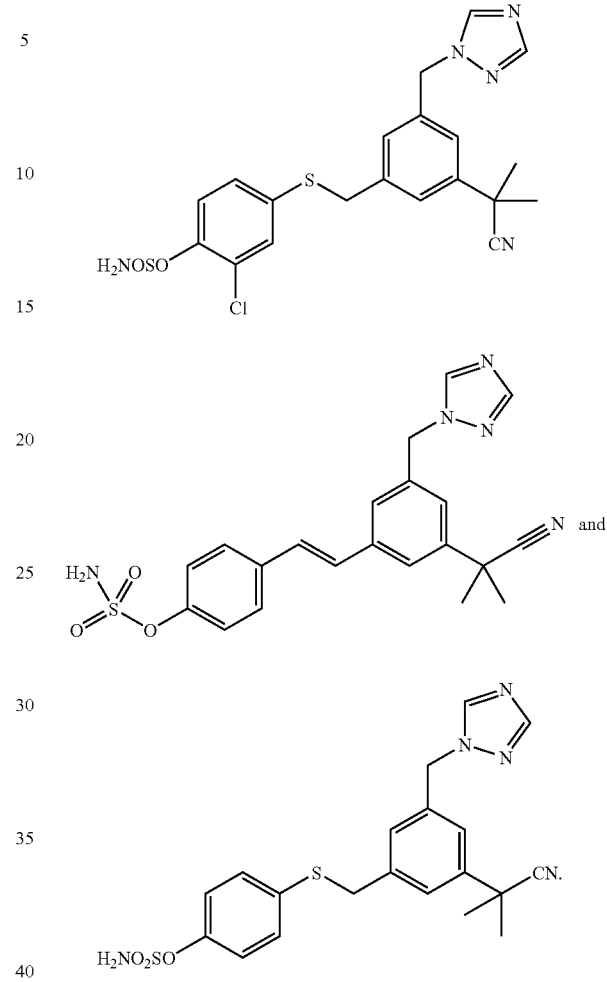
44. A pharmaceutical composition comprising the compound according to claim 1 optionally admixed with a pharmaceutically acceptable carrier, diluent, excipient or adjuvant.
45. A compound according to claim 1 wherein Z is not present and $R_2$ is selected from $CH_3$ and —CN.
46. A compound according to claim 1 wherein X is not present.
* * * * *